US007163800B2

(12) United States Patent
Oakley et al.

(10) Patent No.: US 7,163,800 B2
(45) Date of Patent: Jan. 16, 2007

(54) METHODS OF SCREENING COMPOSITIONS FOR G PROTEIN-COUPLED RECEPTOR DESENSITIZATION INHIBITORY ACTIVITY

(75) Inventors: Robert H. Oakley, Durham, NC (US); Lawrence S. Barak, Durham, NC (US); Stephane A. Laporte, Outremont (CA); Marc G. Caron, Hillsborough, NC (US)

(73) Assignee: Molecular Devices Corporation, Sunnyvale, CA (US)

( * ) Notice: Subject to any disclaimer, the term of this patent is extended or adjusted under 35 U.S.C. 154(b) by 183 days.

(21) Appl. No.: 10/633,438

(22) Filed: Aug. 1, 2003

(65) Prior Publication Data

US 2004/0091946 A1 May 13, 2004

Related U.S. Application Data

(63) Continuation-in-part of application No. 09/993,844, filed on Nov. 5, 2001, now Pat. No. 7,018,812.

(60) Provisional application No. 60/245,772, filed on Nov. 3, 2000, provisional application No. 60/260,363, filed on Jan. 8, 2001.

(51) Int. Cl.
*G01N 33/566* (2006.01)

(52) U.S. Cl. ................ 435/7.21; 435/7.1; 435/7.2; 436/501

(58) Field of Classification Search ............. 435/7.1, 435/7.2, 7.21; 436/501
See application file for complete search history.

(56) References Cited

U.S. PATENT DOCUMENTS

| | | | |
|---|---|---|---|
| 3,654,090 A | 4/1972 | Schuurs et al. | |
| 3,850,752 A | 11/1974 | Schuurs et al. | |
| 4,016,043 A | 4/1977 | Schuurs et al. | |
| 4,341,761 A | 7/1982 | Ganfield et al. | |
| RE31,006 E | 8/1982 | Schuurs et al. | |
| 4,342,566 A | 8/1982 | Theofilopoulos et al. | |
| 4,399,121 A | 8/1983 | Albarella et al. | |
| 4,427,783 A | 1/1984 | Newman et al. | |
| 4,444,887 A | 4/1984 | Hoffmann | |
| 4,451,570 A | 5/1984 | Royston et al. | |
| 4,466,917 A | 8/1984 | Nussenzweig et al. | |
| 4,472,500 A | 9/1984 | Milstein et al. | |
| 4,491,632 A | 1/1985 | Wands et al. | |
| 4,493,890 A | 1/1985 | Morris | |
| 4,816,397 A | 3/1989 | Boss et al. | |
| 4,816,567 A | 3/1989 | Cabilly et al. | |
| 4,981,784 A | 1/1991 | Evans et al. | |
| 5,284,746 A | 2/1994 | Sledziewski et al. | |
| 5,366,889 A | 11/1994 | MacDonald et al. | |
| 5,468,854 A | 11/1995 | McCabe et al. | |
| 5,482,835 A | 1/1996 | King et al. | |
| 5,491,084 A | 2/1996 | Chalfie et al. | |
| 5,532,157 A | 7/1996 | Fink | |
| 5,576,436 A | 11/1996 | McCabe et al. | |
| 5,625,048 A | 4/1997 | Tsien et al. | |
| 5,777,079 A | 7/1998 | Tsien et al. | |
| 5,804,387 A | 9/1998 | Cormack et al. | |
| 5,891,646 A | 4/1999 | Barak et al. | |
| 5,958,713 A | 9/1999 | Thastrup et al. | |
| 5,989,835 A | 11/1999 | Dunlay et al. | |
| 6,066,476 A | 5/2000 | Tsien et al. | |
| 6,096,705 A | 8/2000 | Lefkowitz et al. | |
| 6,107,324 A | 8/2000 | Behan et al. | |
| 6,110,693 A | 8/2000 | Barak et al. | |
| 6,140,509 A | 10/2000 | Behan et al. | |
| 6,150,393 A | 11/2000 | Behan et al. | |
| 6,528,271 B1 * | 3/2003 | Bohn et al. | 435/7.2 |
| 2002/0106739 A1 | 8/2002 | Oakley et al. | |
| 2003/0013137 A1 | 1/2003 | Barak et al. | |
| 2003/0049643 A1 | 3/2003 | Barak et al. | |
| 2004/0029190 A1 | 2/2004 | Barak et al. | |

FOREIGN PATENT DOCUMENTS

| | | |
|---|---|---|
| WO | 88/03168 A1 | 5/1988 |
| WO | 94/16684 A1 | 8/1994 |
| WO | 98/12310 A1 | 3/1998 |
| WO | 98/44350 A1 | 10/1998 |
| WO | 99/66324 A2 | 12/1999 |

(Continued)

OTHER PUBLICATIONS

Gurevich et al. Arrestin Interactions with G Protein-coupled Receptors. Jan. 13, 1995. J. Biol. Chem. 270(2):720-731.*

(Continued)

*Primary Examiner*—John Ulm
(74) *Attorney, Agent, or Firm*—Dorsey & Whitney; David J. Brezner

(57) ABSTRACT

The methods of the present invention allow the screening of a test composition for non-receptor-specific GPCR desensitization inhibitory activity. The methods involve screening a test composition for an indication of GPCR desensitization inhibitory activity against two or more GPCRs that are different from each other. When there is an indication that a particular test composition has GPCR desensitization inhibitory activity with respect to each of the two or more GPCRs that are different from one another, then, according to the present invention, there is an indication that the test composition has non-receptor-specific GPCR desensitization inhibitory activity.

35 Claims, 36 Drawing Sheets

FOREIGN PATENT DOCUMENTS

| WO | 00/12704 A2 | 3/2000 |
|---|---|---|
| WO | 01/58923 A2 | 8/2001 |
| WO | 02/059267 A2 | 8/2002 |

OTHER PUBLICATIONS

Hodgson, J. Receptor Screening and the Search for New Pharmaceuticals. Sep. 10, 1992. BIO/TECHNOLOGY 10:973-977.*

Walker, Julia K. L., et al., *Properties of Secretin Receptor Internalization Differ from Those of the $\beta_2$-Adrenergic Receptor*, Journal of Biological Chemistry, vol. 274, No. 44, Oct. 29, 1999, pp. 31515-31523, The American Society for Biochemistry and Molecular Biology. Inc., U.S.A.

Oakley et al., *The Cellular Distribution of Fluorescently Labeled Arrestins Provides a Robust, Sensitive, and Universal Assay for Screening G Protein-Coupled Receptors*, ASSAY and Drug Development Technologies, vol. 1, No. 1-1, 2002, pp. 21-30.

Angers, S., et al., *Detection of $\beta_2$-Adrenergic receptor dimerization in living cells using bioluminescence resonance energy transfer (BRET)*, Proceedings of the National Academy of Sciences, vol. 97, No. 7, Mar. 28, 2000, pp. 3684-3689, Proc. Natl. Acad. Sci., USA.

Attramadal, H., et al., *$\beta_2$-Arrestin2, a Novel Member of the Arrestin/$\beta$-Arrestin Gene Family*, Journal of Biological Chemistry, vol. 257, No. 25, Sep. 5, 1992, pp. 17882-17890, The American Society for Biochemistry and Molecular Biology, Inc., USA.

Barak, et al., *Abstract #2484, Molecular Biology of the Cell*, vol. 7, p. 427a Dec. 1996, 6th International Congress on Cell Biology & 36th American Society for Cell Biology Annual Meeting, Dec. 7-11, 1996, San Francisco, CA.

Barak, L.S., et al., *Constitutive arrestin-mediated desensitization of a human vasopressin receptor mutant associated with nephrogenic diabetes insipidus*, Proceedings of the National Academy of Sciences, vol. 98, No. 1, Jan. 2, 2001, pp. 93-98, Proc. Natl. Acad. Sci., USA.

Barak, L.S., et al., *A highly Conserved Tyrosine Residue in G Protein-Coupled Receptors is Required for Agonist-mediated $\beta_2$-Adrenergic Receptor Sequestration*, Journal of Biological Chemistry, vol. 269, No. 4, Jan. 28, 1994, pp. 2790-2795, The American Society for Biochemistry and Molecular Biology, Inc., USA.

Barak, L.S., et al., *A $\beta$-Arrestin/Green Fluorescent Protein Biosensor for Detecting G Protein-coupled Receptor Activation*, Journal of Biological Chemistry, vol. 272, No. 44, Oct. 31, 1997, pp. 27497-27500, The American Society for Biochemistry and Molecular Biology, Inc., USA.

Barak, L.S., et al., *The Conserved Seven-Transmembrane Sequence $NP(X)_{22}$ Y of the G-Protein-Coupled Receptor Superfamily Regulates Multiple Properties of the $\beta_2$-Adrenergic Receptor*, Biochemistry, vol. 34, No. 47, 1995, pp. 15407-15414.

Barak, L.S., et al., *Internal Trafficking and Surface Mobility of a Functionally Intact $\beta_2$-Adrenergic Receptor- Green Fluorescent Protein Conjugate*, Molecular Pharmacology, 51, 1997, pp. 177-184.

Barak, L.S., et al., *Real-time Visualization of the Cellular Redistribution of G Protein-coupled Receptor Kinase 2 and $\beta$-arrestin 2 during Homologous Desensitization of the Substance P Receptor*, Journal of Biological Chemistry, vol. 274, No. 11, Mar. 12, 1999, pp. 7565-7569, The American Society for Biochemistry and Molecular Biology, Inc., USA.

Cubitt, A., et al., *Understanding, Improving and Using Green Fluorescent Proteins*, Trends in Biochemical Sciences, International Union of Biochemistry and Molecular Biology, 448-455, Elsevier Trends Journals, Oxford, UK.

Drews, J., *Drug Discovery: A Historical Perspective*, Science, vol. 287, Mar. 17, 2000, pp. 1960-1964, American Association for the Advancement of Science, Washington, D.C.

Ferguson, S.S.G., et al., *G-protein-coupled receptor regulation: role of G-protein-coupled receptor kinases and arrestins*, Can. J. Physiol. Pharmacol., vol. 74, 1996, pp. 1095-1110, NRC, Canada.

Ferguson, S.S.G., *Molecular Mechanisms of G Protein-Coupled Receptor Desensitization and Resensitization*, Life Sciences, XP-002076355, vol. 62, pp. 1561-1565, 1998, Elsevier Publication, USA.

Ferguson, S.S.G., et al., *Role of Phosphorylation in Agonist-promoted $\beta_2$-Adrenergic Receptor Sequestration*, Journal of Biological Chemistry, vol. 270, No. 42, Oct. 20, 1995, pp. 24782-24789, The American Society for Biochemistry and Molecular Biology, Inc., USA.

Ferguson, S.S.G., et al., *Role of $\beta$-arrestin in Mediating Agonist-Promoted G Protein-Coupled Receptor Internalization*, Science, vol. 271, Jan. 19, 1996, pp. 363-366.

Grady, E., et al., *Mechanisms Attenuating Cellular Responses to Neuropeptides: Extracellular Degradation of Ligands and Desensitization of Receptors*, The Journal of Investigative Dermatology Symposium Proceedings, vol. 21, No. 1, pp. 69-75, Aug. 1997, The Society of Investigative Dermatology, Inc.

Harris, E., et al, *Protein Purification Methods*, pp. 12-18, 1989, Oxford University Press, New York, U.S.

Hausdorff, W.P., et al., *A Mutation of the $\beta_2$-Adrenergic Receptor Impairs Agonist Activation of Adenylyl Cyclase without Affecting High Affinity Agonist Binding*, Journal of Biological Chemistry, vol. 265, No. 3, Jan. 25, 1990, pp. 1388-1393, The American Society for Biochemistry and Molecular Biology, Inc., USA.

Kim, K.-M., et al., *Differential Regulation of the Dopamine $D_2$ and $D_3$ Receptors by G Protein-coupled Receptor Kinases and $\beta$-arrestins*, Journal of Biological Chemistry, vol. 276 No. 40, Oct. 5, 2001, pp. 37409-97414, The American Society for Biochemistry and Molecular Biology, Inc., USA.

Laporte, S. A., et al., *The Interaction of $\beta$-Arrestin with the AP-2 Adaptor is Required for the Clustering of $\beta_2$-Adrenergic Receptor into Clathrin-coated Pits*, Journal of Biological Chemistry, vol. 275, No. 30, Jul. 28, 2000, pp. 23120-23126, The American Society for Biochemistry and Molecular Biology, Inc., USA.

Laporte, S.A., et al., *The $\beta_2$-Adrenergic Receptor/ $\beta$-arrestin complex recruits the clathrin adaptor AP-2 during endocytosis*, Proceedings of the National Academy of Sciences, vol. 96, No. 7, Mar. 30, 1999, pp. 3712-3717, Proc.Natl. Acad. Sci, USA.

Lohse, M., et al., *$\beta$-Arrestin: A Protein That Regulates $\beta$-Adrenergic Receptor Function*, Science, vol. 248, pp. 1547-1550, Jun. 22, 1990.

McConalogue, K., et al., *Activation and Internalization of the $\mu$-opioid Receptor by the Newly Discovered Endogenous Agonists, Endomorphin-1 and Endomorphin-2*, Neuroscience, vol. 90, No. 3, pp. 1051-1059, 1999, Elsevier Science Ltd., Great Britain.

McConalogue, K., et al., *Cellular and Subcellular Localization of G-Protein Receptor Kinases, Arrestins and G-Proteins: Implications for Receptor Regulation*, Supplement to Gastroenterology, Digestive Disease Week and the 96th Annual Meeting of the American Gastroenerological Association, vol. 110, No. 4, Apr. 1996.

McConalogue, K., et al., *G Protein-Coupled Receptors in Gastrointestinal Physiology II. Regulation of Neuropeptide receptors in enteric neurons, Receptor Regulation*, pp. G792-G796, 1998, American Physiological Society.

McConalogue, K., et al., *Substance P-induced Trafficking of $\beta$-arrestins*, Journal of Biological Chemistry, vol. 274, No. 23, pp. 16257-16268, Jun. 4, 1999, The American Society for Biochemistry and Molecular Biology, Inc., USA.

Menard, L., et al., *Members the G Protein-Coupled Receptor Kinase Family that Phosphorylate the $\beta_2$-Adrenergic Receptor Facilitate Sequestration*, Biochemistry, vol. 35, No. 13, 1996, pp. 4155-4160, The American Chemical Society.

Menard, L., et al., *Synergistic Regulation of $\beta_2$-Adrenergic Receptor Sequestration: Intracellular Complement of $\beta_2$-Adrenergic Receptor Kinase and $\beta_2$-Arrestin Determine Kinetics of Internalization*, Molecular Pharmacology, vol. 51, No. 5, May 1997, pp. 800-808, The American Society for Pharmacology and Experimental Therapeutics.

Mhaouty-Kodja, S., et al., *Constitutively Active Alpha-1b Adrenergic Receptor Mutants Display Phosohorylation and Internalization Features*, Molecular Pharmacology, vol. 55, No. 2, Feb. 1999, pp. 339-347, The American Society for Pharmacology and Experimental Therapeutics.

Ormo, M., et al., *Crystal Structure of the Aequorea victoria Green Fluorescent Proteins, Science*, vol. 273, pp. 1392-1395, 1996, American Association for the Advancement of Science, Washington D.C.

Oakley, R.H., et al., *Association of β-Arrestin with G Protein-coupled Receptors during Clathrin-mediated Endocytosis Dictates the Profile of Receptor Resensitization, Journal of Biological Chemistry*, vol. 274, No. 45, Nov. 5, 1999, pp. 17201-17210, The American Society for Biochemistry and Molecular Biology, Inc., USA.

Oakley, R.H., et al., *Differential Affinities of Visual Arrestin, β-Arrestin1, and β-Arrestin2 for G Protein-coupled Receptors Delineate Two Major Classes of Receptors, Journal of Biological Chemistry*, vol. 275, No. 22, Jun. 2, 2000, pp. 17201-17210, The American Society for Biochemistry and Molecular Biology, Inc., USA.

Oakley, R.H., et al., *Molecular Determinants Underlying the Formation of Stable Intracellular G Protein-coupled Receptor-β-Arrestin Complexes after Receptor Endocytosis, Journal of Biological Chemistry*, vol. 276, No. 22, Jun. 1, 2001, pp. 19452-19460, The American Society for Biochemistry and Molecular Biology, Inc., USA.

Yokoe, *Spatial Dynamics of GFP-tagged proteins investigated by local fluorescence enhancement, Nature Biotechnology*, vol. 14, pp. 1252-1256, Oct. 14, 1996.

Zhang, J., et al., *Cellular Trafficking of G Protein-coupled Receptor/β-Arrestin Endocytic Complexes, Journal of Biological Chemistry*, vol. 274, No. 16, Apr. 16, 1999, pp. 10999-11006, The American Society for Biochemistry and Molecular Biology, Inc., USA.

Zhang, J., et al., *A Central Role for β-Arrestins and Clathrin-coated Vesicle-mediated Endocytosis in β$_2$-Adrenergic Receptor Resensitization, Journal of Biological Chemistry*, vol. 272, No. 43, Oct. 24, 1997, pp. 27005-27014, The American Society for Biochemistry and Molecular Biology, Inc., USA.

\* cited by examiner

FIG. 2A

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I Rhodopsin like | | | | | |
| | •Amine | | | | |
| | •Acetylcholine (muscarinic & nicotinic) | 5 | Brain, Nerves, Heart | Neurotransmitter | Acuity, Alzheimer's |
| | •Adrenoceptors | | | | |
| | •Alpha Adrenoceptors | 6 | Brain, Kidney, Lung | Gluconeogenesis | Diabetes, Cardiovascular |
| | •Beta Adrenoceptors | 3 | Kidney, Heart | Muscle Contraction | Cardiovascular, Respiratory |
| | •Dopamine | 5 | Brain, Kidney, GI | Neurotransmitter | Cardiovascular, Parkinson's |
| | •Histamine | 2 | Vascular, Heart, Brain | Vascular Permeability | Anti-inflammatory, Ulcers |
| | •Serotonin (5-HT) | 16 | Most Tissues | Neurotransmitter | Depression, Insomnia, Analgesic |
| | •Peptide | | | | |
| | •Angiotensin | 2 | Vascular, Liver, Kidney | Vasoconstriction | Cardiovascular, Endocrine |
| | •Bradykinin | 1 | Liver, Blood | Vasodilation, | Anti-inflammatory, Asthma |
| | •C5a anaphylatoxin | 1 | Blood | Immune System | Anti-inflammatory |
| | •Fmet-leu-phe | 3 | Blood | Chemoattractant | Anti-inflammatory |
| | •Interleukin-8 | 1 | Blood | Chemoattractant | Anti-inflammatory |
| | •Chemokine | 6 | Blood | Chemoattractant | Anti-inflammatory |
| | •Orexin | 2 | Brain | Fat Metabolism | Obesity |
| | •Nociceptin | 1 | Brain | Bronchodilator, Pain | Airway Diseases, Anesthetic |
| | •CCK (Gastrin) | 2 | Gastrointestinal | Motility, Fat Absorption | Gastrointestinal, Obesity, Parkinson's |
| | •Endothelin | 2 | Heart, Bronchus, Brain | Muscle Contraction | Cardiovascular, Respiratory |
| | •Melanocortin | 2 | Kidney, Brain | Metabolic Regulation | Anti-inflammatory, Analgesics |
| | •Neuropeptide Y | 5 | Nerves, Intestine, Blood | Neurotransmitter | Behavior, Memory, Cardiovascular |
| | •Neurotensin | 1 | Brain, | CNS | Cardiovascular, Analgesic |
| | •Opioid | 3 | Brain, | CNS | Depression, Analgesic |
| | •Somatostatin | 5 | Brain, Gastrointestinal | Neurotransmitter | Oncology, Alzheimer's |

FIG. 2B

| | | | |
|---|---|---|---|
| •Tachykinin (Substance P, NKA₁) | 3 | Brain Nerves | Neurohormone | Depression, Analgesic |
| •Thrombin | 3 | Platelets, Blood Vessels | Coagulation | Anti-coagulant, Anti-inflammatory |
| •Vasopressin-like | 4 | Arteries, Heart, Bladder | Water Balance | Anti-diuretic, Diabetic Complications |
| •Galanin | 1 | Brain, Pancreas | Neurotransmitter | Analgesics, Alzheimer's |
| •Hormone protein | | | | |
| •Follicle stimulating hormone | 1 | Ovary, Testis | Endocrine | Infertility |
| •Lutropin-choriogonadotropic | 1 | Ovary, Testis | Endocrine | Infertility |
| •Thyrotropin | 1 | Thyroid | Endocrine | Thyroidism, Metabolism |
| •(Rhod)opsin | | | | |
| •Opsin | 5 | Eye | Photoreception | Ophthalmic Diseases |
| •Olfactory | 4(~1000) | Nose | Smell | Olfactory Diseases |
| •Prostanoid | | | | |
| •Prostaglandin | 5 | Arterial, Gastrointestinal | Vasodilation, Pain | Cardiovascular, Analgesic |
| •Lysophosphatidic Acid | 2 | Vessels, Heart, Lung | Inflammation | Cancer, Anti-Inflammatory |
| •Sphingosine-1-phosphate | 2 | Most Cells | Cell proliferation | Cancer |
| •Leukotriene | 1 | White Blood Cells, Bronchus | Inflammation | Asthma, Rheumatoid Arthritis |
| •Prostacyclin | 1 | Arterial, Gastrointestinal | Platelet Regulation | Cardiovascular |
| •Thromboxane | 1 | Arterial, Bronchus | Vasoconstriction | Cardiovascular, Respiratory |
| •Nucleotide-like | | | | |
| •Adenosine | 4 | Vascular, Bronchus | Multiple Effects | Cardiovascular, Respiratory |
| •Purinoceptors | 4 | Vascular, Platelets | Relaxes Muscle | Cardiovascular, Respiratory |
| •Cannabis | 2 | Brain | Sensory Perception | Analgesics, Memory |
| •Platelet activating factor | 1 | Most Peripheral Tissues | Inflammation | Anti-inflammatory, Anti-asthmatic |
| •Gonadotropin-releasing hormone like | | | | |
| •Gonadotropin-releasing hormone | 1 | Reproductive Organs, Pituitary | Reproduction | Prostate Cancer, Endometriosis |
| •Thyrotropin-releasing hormone | 1 | Pituitary, Brain | Thyroid Regulation | Metabolic Regulation |
| •Growth hormone-inhibiting factor | 1 | Gastrointestinal | Neuroendocrine | Oncology, Alzheimer's |
| •Melatonin | 1 | Brain, Eye, Pituitary | Neuroendocrine | Regulation of Circadian Cycle |

FIG. 2C

- Class II
  Secretin like
  - Secretin — 1 — Gastrointestinal, Heart — Digestion — Obesity, Gastrointestinal
  - Calcitonin — 1 — Bone, Brain — Calcium Resorption — Osteoporosis
  - Corticotropin releasing factor/urocortin — 1 — Adrenal, Vascular, Brain — Neuroendocrine — Stress, Mood, Obesity
  - Gastric inhibitory peptide (GIP) — 1 — Adrenals, Fat Cells — Sugar/Fat Metabolism — Diabetes, Obesity
  - Glucagon — 1 — Liver, Fat Cells, Heart — Gluconeogenesis — Cardiovascular
  - Glucagon-like Peptide 1 (GLP-1) — 1 — Pancreas, Stomach, Lung — Gluconeogenesis — Cardiovascular, Diabetes, Obesity
  - Growth hormone-releasing hormone — 1 — Brain — Neuroendocrine — Growth Regulation
  - Parathyroid hormone — 1 — Bone, Kidney — Calcium Regulation — Osteoporosis
  - PACAP — 1 — Brain, Pancreas, Adrenals — Metabolism — Metabolic Regulation
  - Vasoactive intestinal polypeptide (VIP) — 1 — Gastrointestinal — Motility — Gastrointestinal

- Class III
  - Metabotropic Glutamate — 7 — Brain — Sensory Perception — Hearing, Vision
  - GABA$_B$ — 1 — Brain — Neurotransmitter — Mood Disorders
  - Extracellular Calcium Sensing — 1 — Parathyroid, Kidney, GI Tract — Calcium Regulation — Cataracts, GI Tumors

FIG. 3A

G protein-coupled receptors:
(Division into Class A
Or Class B)

1.  A1 adenosine receptor [Homo sapiens]. ACCESSION AAB25533
    NPIVYAF RIQKFRVTFL KIWNDHFRCQ PAPPIDEDLP EERPDD
    *Class A*

2.  adrenergic, alpha -1B-, receptor [Homo sapiens]. ACCESSION NP_000670
    npiiypc sskefkrafv rilgcqcrgr grrrrrrrr lggcaytyrp wtrggslers qsrkdsldds gsclsgsqrt lpsaspspgy lgrgapppve lcafpewkap gallslpape ppgrrgrhds gplftfkllt epespgtdgg asnggceaaa dvangqpgfk snmplapgqf
    *Class A*

3.  adrenergic receptor alpha-2A [Homo sapiens]. ACCESSION AAG00447
    npviytifn hdfrrafkki lcrgdrkriv
    *Class A*

4.  alpha-2B-adrenergic receptor - human. ACCESSION A37223
    npviytifn qdfrrafrri lcrpwtqtaw
    *Class A*

5.  alpha-2C-adrenergic receptor - human. ACCESSION A31237
    npviytvfn qdfrpsfkhi lfrrrrgfr q
    *Class A*

6.  beta-1-adrenergic receptor [Homo sapiens]. ACCESSION NP_000675
    npiiycrs pdfrkafqgl lccarraarr rhathgdrpr asgclarpgp ppspgaasdd ddddvvgatp parllepwag cnggaaadsd ssldepcrpg faseskv
    *Class A*

7.  beta-2 adrenergic receptor. ACCESSION P07550
    npliycrsp dfriafqell clrrsslkay gngyssngnt 361 geqsgyhveq ekenkllced lpgtedfvgh qgtvpsdnid sqgrncstnd sll
    *Class A*

8.  dopamine receptor D1 [Homo sapiens]. ACCESSION NP_000785
    npii yafnadfrka fstllgcyrl cpatmnaiet vsinnngaam fsshheprgs iskecnlvyl iphavgssed lkkeeaagia rpleklspal svildydtdv slekiqpitq ngqhpt
    *Class A*

9.  D(2) dopamine receptor. ACCESSION P14416
    npiiyttfn iefrkaflki lhc
    *Class A*

FIG. 3B

10. d3 dopamine receptor - human. ACCESSION G01977
    np viyttfnief rkaflkilsc
    Class A 11. dopamine receptor D4 - human. ACCESSION DYHUD4
    npviytv fnaefrnvfr kalracc
    Class A 12. dopamine receptor D5 - human. ACCESSION DYHUD5
    npviya fnadfqkvfa qllgcshfcs rtpvetvnis nelisynqdi vfhkeiaaay ihmmpnavtp gnrevdndee
    egpfdrmfqi yqtspdgdpv aesvweldce geisldkitp ftpngfh
    Class A 13. muscarinic acetylcholine receptor M1 [Homo sapiens]. ACCESSION NP_000729
    npmcyal cnkafrdtfr llllcrwdkr rwrkipkrpg svhrtpsrqc
    Class A 14. muscarinic acetylcholine receptor M2 [Homo sapiens]. ACCESSION NP_000730
    npacy alcnatfkkt fkhllmchyk nigatr
    Class A 15. muscarinic acetylcholine receptor M3 [Homo sapiens]. ACCESSION NP_000731
    n pvcyalcnkt frttfkmlll cqcdkkkrrk qqyqqrqsvi fhkrapeqal
    Class A 16. muscarinic acetylcholine receptor M4 [Homo sapiens]. ACCESSION NP_000732
    npa cyalcnatfk ktfrhlllcq yrnigtar
    Class A 17. m5 muscarinic receptor. locus HUMACHRM ACCESSION AAA51569
    npicyalcnr tfrktfkmll lcrwkkkkve eklywqgnsk lp
    Class A 18. 5-hydroxytryptamine (serotonin) receptor 1A [Homo sapiens]. ACCESSION BAA90449
    npviy ayfnkdfqna fkkiikckf
    Class A 19. 5-hydroxytryptamine (serotonin) receptor 1B [Homo sapiens]. ACCESSION BAA94455
    npiiyt msnedfkqaf hklirfkcts
    Class A 20. 5-hydroxytryptamine (serotonin) receptor 1E [Homo sapiens]. ACCESSION BAA94458
    n pllytsfned fklafkkllr cre
    Class A

FIG. 3C

21. OLFACTORY RECEPTOR 6A1. ACCESSION O95222
    npiiyclmq evkralccil hlyqhqdpdp kkgsmv
    Class A 22. OLFACTORY RECEPTOR 2C1. ACCESSION O95371
    npliy tlmmevkga lrrllgkgre vg
    Class A 23. angiotensin receptor 1 [Homo sapiens]. ACCESSION NP_033611
    npl fygflgkkfk ryflqllkyi ppkakshsnl sfkmsflsyr psdnvssstk kpapcfeve
    Class B 24. angiotensin receptor 2 [Homo sapiens]. ACCESSION NP_000677
    npflycf vgnrfqqklr svfrvpitwl qgkresmscr kssslremet fvs
    Class B 25. interleukin 8 receptor beta (CXCR2) [Homo sapiens]. ACCESSION NM_001557
    NPLIYAFIGQKFRHGLLKILAIHGLISKDSLPKDSRPSFVGSSSGHTSTTL
    Class B 26. cx3c chemokine receptor 1 (cx3cr1) (fractalkine receptor)
    ACCESSION P49238
    np liyafagekf rrylyhlygk clavlcgrsv hvdfsssesq rsrhgsvlss nftyhtsdgd allll
    Class B 27. neurotensin receptor - human. ACCESSION S29506
    n pilynlvsan frhiflatla clcpvwrrrr krpafsrkad svssnhflss natretly
    Class B 28. SUBSTANCE-P RECEPTOR (SPR) (NK-1 RECEPTOR) (NK-1R). ACCESSION P25103
    npiiycclnd rfrlgfkhaf rccpfisagd yeglemkstr ylqtqgsvyk vsrlettistvvgaheeepe dgpkatpssl
    dltsncssrs dsktmtesfs fssnvls
    Class B 29. vasopressin receptor type 2 [Homo sapiens]. ACCESSION AAD16444
    npwiyasfss svsselrsll ccargrtpps lgpqdesctt assslakdfs s
    Class B 30. thyrotropin-releasing hormone receptor - human. ACCESSION JN0708
    npviy nlmsqkfraa frklcnckqk ptekpanysv alnysvikes dhfstelddi tvtdtylsat kvsfddtcla sevsfsqs
    Class B

FIG. 3D

31. oxytocin receptor - human. ACCESSION A55493
    npwiym lftghlfhel vqrflccsas ylkgrrlget saskksnsss fvlshrsssq rscsqpsta
    Class B 32. neuromedin U receptor [Homo sapiens]. ACCESSION AAG24793
    npvlyslmssrfretfqealclgacchrlrprhsshslsrmttgstlcdvgslgswvhplagndgpeaqqetdps
    Class B 33. gastrin receptor. ACCESSION AAC37528
    nplvy cfmhrrfrqa cletcarccp rpprarpral pdedpptpsi aslsrlsytt lstlgpg
    Class B 34. galanin receptor 3 [Homo sapiens]. ACCESSION 10879541
    nplv yalasrhfra rfrrlwpcgr rrhrarral rrvrpassgp pgcpgdarps grllagggqg pepregpvhg geaargpe
    Class A 35. edg-1 - human. ACCESSION A35300
    npiiy tltnkemrra firimscckc psgdsagkfk rpiiagmefs rsksdnsshp 361 qkdegdnpet imssgnvnss s
    Class A 36. central cannabinoid receptor [Homo sapiens]. ACCESSION NP_057167
    npiiyalr skdlrhafrs mfpscegtaq pldnsmgdsd clhkhannaa svhraaesci kstvkiakvt msvstdtsae al
    Class A 37. delta opioid receptor - human. ACCESSION I38532
    npvlyaf ldenfkrcfr qlcrkpcgrp dpssfsrpre atarervtac tpsdgpgggr aa
    Class A 38. proteinase activated receptor 2 (PAR-2) human. ACCESSION P55085
    dpfvyyfvshdfrdhaknallcrsvrtvkqmqvsltskkhsrksssysssttvktsy
    Class A 39. vasopressive intestinal peptide receptor (VIPR) rat. ACCESSION NM_012685
    NGEVQAELRRKWRRWHLQGVLGWSSKSQHPWGGSNGATCSTQVSMLTRVSPSARR
    SSSFQAEVSLV
    Class B

FIG. 4A

The mutated amino acid at the second position of the DRY motif is underlined.

VASOPRESSIN V2 RECEPTOR - (Human)
accession P30518

R137H

```
  1 MLMASTTSAV PGHPSLPSLP SNSSQERPLD TRDPLLARAE LALLSIVFVA VALSNGLVLA
 61 ALARRGRRGH WAPIHVFIGH LCLADLAVAL FQVLPQLAWK ATDRFRGPDA LCRAVKYLQM
121 VGMYASSYMI LAMTLDHHRA ICRPMLAYRH GSGAHWNRPV LVAWAFSLLL SLPQLFIFAQ
181 RNVEGGSGVT DCWACFAEPW GRRTYVTWIA LMVFVAPTLG IAACQVLIFR EIHASLVPGP
241 SERPGGRRRG RRTGSPGEGA HVSAAVAKTV RMTLVIVVVY VLCWAPFFLV QLWAAWDPEA
301 PLEGAPFVLL MLLASLNSCT NPWIYASFSS SVSSELRSLL CCARGRTPPS LGPQDESCTT
361 ASSSLAKDTS S
```
(SEQ ID NO:40)

ALPHA-1B ADRENERGIC RECEPTOR (ALPHA 1B-ADRENOCEPTOR).
(Golden hamster)
ACCESSION P18841
R143E

```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDEYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:41)

R143A

```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDAYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:42)

```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDHYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:43)

R143N

```
  1 MNPDLDTGHN TSAPAQWGEL KDANFTGPNQ TSSNSTLPQL DVTRAISVGL VLGAFILFAI
 61 VGNILVILSV ACNRHLRTPT NYFIVNLAIA DLLLSFTVLP FSATLEVLGY WVLGRIFCDI
121 WAAVDVLCCT ASILSLCAIS IDNYIGVRYS LQYPTLVTRR KAILALLSVW VLSTVISIGP
181 LLGWKEPAPN DDKECGVTEE PFYALFSSLG SFYIPLAVIL VMYCRVYIVA KRTTKNLEAG
241 VMKEMSNSKE LTLRIHSKNF HEDTLSSTKA KGHNPRSSIA VKLFKFSREK KAAKTLGIVV
301 GMFILCWLPF FIALPLGSLF STLKPPDAVF KVVFWLGYFN SCLNPIIYPC SSKEFKRAFM
361 RILGCQCRSG RRRRRRRLG ACAYTYRPWT RGGSLERSQS RKDSLDDSGS CMSGSQRTLP
421 SASPSPGYLG RGAQPPLELC AYPEWKSGAL LSLPEPPGRR GRLDSGPLFT FKLLGEPESP
481 GTEGDASNGG CDATTDLANG QPGFKSNMPL APGHF
```
(SEQ ID NO:44)

FIG. 4C

Angiotensin II Receptor, Type 1 (AT1A) [Rattus norvegicus].
ACCESSION NP_112247

R126H

```
  1 MALNSSAEDG IKRIQDDCPK AGRHSYIFVM IPTLYSIIFV VGIFGNSLVV IVIYFYMKLK
 61 TVASVFLLNL ALADLCFLLT CPLWAVYTAM EYRWPFGNHL CKIASASVTF NLYASVFLLT
121 CLSIDHYLAI VHPMKSRLRR TMLVAKVTCI IIWLMAGLAS LPAVIHRNVY FIENTNITVC
181 AFHYESRNST LPIGLGLTKN ILGFLFPFLI ILTSYTLIWK ALKKAYEIQK NKPRNDDIFR
241 IIMAIVLFFF FSWVPHQIFT FLDVLIQLGV IHDCKISDIV DTAMPITICI AYFNNCLNPL
301 FYGFLGKKFK KYFLQLLKYI PPKAKSHSSL STKMSTLSYR PSDNMSSSAK KPASCFEVE
```
(SEQ ID NO:45)

FIGS. 5A – 5B

A. Amino Acid sequence of the hGPR3- Enhanced Receptor

MMWGAGSPLAWLSAGSGNVNVSSVGPAEGPTGPAAPLPSPKAWDVVLCISGTLVSCENA
LVVAIIVGTPAFRAPMFLLVGSLAVADLLAGLGLVLHFAAVFCIGSAEMSLVLVGVLAM
AFTASIGSLLAITVDRYLSLYNALTYYSETTVTRTYVMLALVWGGALGLGLLPVLAWNC
LDGLTTCGVVYPLSKNHLVVLAIAFFMVFGIMLQLYAQICRIVCRHAQQIALQRHLLPA
SHYVATRKGIATLAVVLGAFAACWLPFTVYCLLGDAHSPPLYTYLTLLPATYNSMINPI
IYAFRNQDVQKVLWAVCCCCAAARGRTPPSLGPQDESCTTASSSLAKDTSS
(SEQ ID No: 46)

B. Nucleotide sequence of the hGPR3- Enhanced Receptor

ATGATGTGGGGTGCAGGCAGCCCTCTGGCCTGGCTCTCAGCTGGCTCAGGCAACGTGAA
TGTAAGCAGCGTGGGCCCAGCAGAGGGGCCCACAGGTCCAGCCGCACCACTGCCCTCGC
CTAAGGCCTGGGATGTGGTGCTCTGCATCTCAGGCACCCTGGTGTCCTGCGAGAATGCG
CTAGTGGTGGCCATCATCGTGGGCACTCCTGCCTTCCGTGCCCCATGTTCCTGCTGGT
GGGCAGCCTGGCCGTGGCAGACCTGCTGGCAGGCCTGGGCCTGGTCCTGCACTTTGCTG
CTGTCTTCTGCATCGGCTCAGCGGAGATGAGCCTGGTGCTGGTTGGCGTGCTGGCAATG
GCCTTTACYGCCAGCATCGGCAGTCTACTGGCCATCACTGTCGACCGCTACCTTTCTCT
GTACAATGCCCTCACCTACTATTCAGAGACAACAGTGACACGGACCTATGTGATGCTGG
CCTTAGTGTGGGGAGGTGCCCTGGGCCTGGGGCTGCTGCCTGTGCTGGCCTGGAACTGC
CTGGATGGCCTGACCACATGTGGCGTGGTTTATCCACTCTCCAAGAACCATCTGGTAGT
TCTGGCCATTGCCTTCTTCATGGTGTTTGGCATCATGCTGCAGCTCTACGCCCAAATCT
GCCGCATCGTCTGCCGCCATGCCCAGCAGATTGCCCTTCAGCGGCACCTGCTGCCTGCC
TCCCACTATGTGGCCACCCGCAAGGGCATTGCCACACTGGCCGTGGTGCTTGGAGCCTT
TGCCGCCTGCTGGTTGCCCTTCACTGTCTACTGCCTGCTGGGTGATGCCCACTCTCCAC
CTCTCTACACCTATCTTACCTTGCTCCCTGCCACCTACAACTCCATGATCAACCCTATC
ATCTACGCCTTCCGCAACCAGGATGTGCAGAAAGTGCTGTGGGCTGTCTGCTGCTGCTG
TGCGGCCGCACGGGGACGCACCCCACCCAGCCTGGGTCCCAAGATGAGTCCTGCACCA
CCGCCAGcTCCTCCCTGGCCAAGGACACTTCATCGTGA
(SEQ ID No: 47)

FIGS. 5C – 5D

C. Amino Acid sequence of the hGPR6- Enhanced Receptor

MNASAASLNDSQVVVVAAEGAAAAATAAGGPDTGEWGPPAAAALGAGGGANGSLELSSQ
LSAGPPGLLLPAVNPWDVLLCVSGTVIAGENALVVALIASTPALRTPMFVLVGSLATAD
LLAGCGLILHFVFQYLVPSETVSLLTVGFLVASFAASVSSLLAITVDRYLSLYNALTYY
SRRTLLGVHLLLAATWTVSLGLGLLPVLGWNCLAERAACSVVRPLARSHVALLSAAFFM
VFGIMLHLYVRICQVVWRHAHQIALQQHCLAPPHLAATRKGVGTLAVVLGTFGASWLPF
AIYCVVGSHEDPAVYTYATLLPATYNSMINPIIYAFRNQEIQRALWLLLCGCAAARGRT
PPSLGPQDESCTTASSSLAKDTSS
(SEQ ID No: 48)

D. Nucleotide sequence of the hGPR6- Enhanced Receptor

ATGAACGCGAGCGCCGCCTCGCTAACGACTCCCAGGTGGTGGTAGTGGCGGCCGAAGG
AGCGGCGGCGGCGGCCACAGCAGCAGGGGGGCCGGACACGGGCGAATGGGGACCCCTG
CTGCGGCGGCTCTAGGAGCCGGCGGCGGAGCTAATGGGTCTCTGGAGCTGTCCTCGCAG
CTGTCGGCTGGGCCACCGGGACTCCTGCTGCCAGCGGTGAATCCGTGGGACGTGCTCCT
GTGCGTGTCGGGGACAGTGATCGCTGGAGAAAACGCGCTGGTGGTGGCGCTCATCGCGT
CCACTCCGGCGCTGCGCACGCCCATGTTCGTGCTGGTAGGCAGCCTGGCCACCGCTGAC
CTGTTGGCGGGCTGTGGCCTCATCTTGCACTTTGTGTTCCAGTACTTGGTGCCCTCGGA
GACTGTGAGTCTGCTCACGGTGGGCTTCCTCGTGGCCTCCTTCGCCGCCTCTGTCAGCA
GCCTGCTGGCCATTACGGTGGACCGCTACCTGTCCCTGTATAACGCGCTCACCTATTAC
TCGCGCCGGACCCTGTTGGGCGTGCACCTCCTGCTTGCCGCCACTTGGACCGTGTCCCT
AGGCCTGGGGCTGCTGCCCGTGCTGGGCTGGAACTGCCTGGCAGAGCGCGCCGCCTGCA
GCGTGGTGCGCCCGCTGGCGCGCAGCCACGTGGCTCTGCTCTCCGCCGCCTTCTTCATG
GTCTTCGGCATCATGCTGCACCTGTACGTGCGCATCTGCCAGGTGGTCTGGCGCCACGC
GCACCAGATCGCGCTGCAGCAGCACTGCCTGGCGCCACCCCATCTCGCTGCCACCAGAA
AGGGTGTGGGTACACTGGCTGTGGTGCTGGGCACTTTCGGCGCCAGCTGGCTGCCCTTC
GCCATCTATTGCGTGGTGGGCAGCCATGAGGACCCGGCGGTCTACACTTACGCCACCCT
GCTGCCCGCCACCTACAACTCCATGATCAATCCCATCATCTATGCCTTCCGCAACCAGG
AGATCCAGCGCGCCCTGTGGCTCCTGCTCTGTGGCTGTGCGGCCGCACGGGACGCACC
CCACCCAGCCTGGGTCCCCAAGATGAGTCCTGCACCACCGCCAGCTCCTCCCTGGCCAA
GGACACTTCATCGTGA
(SEQ ID No: 49)

FIGS. 5E – 5F

E. Amino Acid sequence of the hGPR12- Enhanced Receptor

MNEDLKVNLSGLPRDYLDAAAAENISAAVSSRVPAVEPEPELVVNPWDIVLCTSGTLIS
CENAIVVLIIFHNPSLRAPMFLLIGSLALADLLAGIGLITNFVFAYLLQSEATKLVTIG
LIVASFSASVCSLLAITVDRYLSLYYALTYHSERTVTFTYVMLVMLWGTSICLGLLPVM
GWNCLRDESTCSVVRPLTKNNAAILSVSFLFMFALMLQLYIQICKIVMRHAHQIALQHH
FLATSHYVTTRKGVSTLAIILGTFAACWMPFTLYSLIADYTYPSIYTYATLLPATYNSI
INPVIYAFRNQEIQKALCLICCGCAAARGRTPPSLGPQDESCTTASSSLAKDTSS
(SEQ ID No: 50)

F. Nucleotide sequence of the hGPR12- Enhanced Receptor

ATGAATGAAGACCTGAAGGTCAATTTAAGCGGGCTGCCTCGGGATTATTTAGATGCCGC
TGCTGCGGAGAACATCTCGGCTGCTGTCTCCTCCCGGGTTCCTGCCGTAGAGCCAGAGC
CTGAGCTCGTAGTCAACCCCTGGGACATTGTCTTGTGTACCTCGGGAACCCTCATCTCC
TGTGAAAATGCCATTGTGGTCCTTATCATCTTCCACAACCCCAGCCTGCGAGCACCCAT
GTTCCTGCTAATAGGCAGCCTGGCTCTTGCAGACCTGCTGGCCGGCATTGGACTCATCA
CCAATTTTGTTTTTGCCTACCTGCTTCAGTCAGAAGCCACCAAGCTGGTCACGATCGGC
CTCATTGTCGCCTCTTTCTCTGCCTCTGTCTGCAGCTTGCTGGCTATCACTGTTGACCG
CTACCTCTCACTGTACTACGCTCTGACGTACCATTCGGAGAGGACGGTCACGTTTACCT
ATGTCATGCTCGTCATGCTCTGGGGACCTCCATCTGCCTGGGGCTGCTGCCCGTCATG
GGCTGGAACTGCCTCCGAGACGAGTCCACCTGCAGCGTGGTCAGACCGCTCACCAAGAA
CAACGCGGCCATCCTCTCGGTGTCCTTCCTCTTCATGTTTGCGCTCATGCTTCAGCTCT
ACATCCAGATCTGTAAGATTGTGATGAGGCACGCCCATCAGATAGCCCTGCAGCACCAC
TTCCTGGCCACGTCGCACTATGTGACCACCCGGAAGGGGTCTCCACCCTGGCTATCAT
CCTGGGGACGTTTGCTGCTTGCTGGATGCCTTTCACCCTCTATTCCTTGATAGCGGATT
ACACCTACCCCTCCATCTATACCTACGCCACCCTCCTGCCCGCCACCTACAATTCCATC
ATCAACCCTGTCATATATGCTTTCAGAAACCAAGAGATCCAGAAAGCGCTCTGTCTCAT
TTGCTGCGGCTGCGCGGCCGCACGGGGACGCACCCCACCCAGCCTGGGTCCCCAAGATG
AGTCCTGCACCACCGCCAGCTCCTCCCTGGCCAAGGACACTTCATCGTGA
(SEQ ID No: 51)

FIGS. 5G – 5H

G. Amino Acid sequence of the hSREB3- Enhanced Receptor

MANTTGEPEEVSGALSPPSASAYVKLVLLGLIMCVSLAGNAILSLLVLKERALHKAPYY
FLLDLCLADGIRSAVCFPFVLASVRHGSSWTFSALSCKIVAFMAVLFCFHAAFMLFCIS
VTRYMAIAHHRFYAKRMTLWTCAAVICMAWTLSVAMAFPPVFDVGTYKFIREEDQCIFE
HRYFKANDTLGFMLMLAVLMAATHAVYGKLLLFEYRHRKMKPVQMVPAISQNWTFHGPG
ATGQAAANWIAGFGRGPMPPTLLGIRQNGHAASRRLLGMDEVKGEKQLGRMFYAITLLF
LLLWSPYIVACYWRVFVKACAVPHRYLATAVWMSFAQAAVNPIVCFLLNKDLKKCLRTH
APCAAARGRTPPSLGPQDESCTTASSSLAKDTSS
(SEQ ID No: 52)

H. Nucleotide sequence of the hSREB3- Enhanced Receptor

ATGGCCAACACTACCGGAGAGCCTGAGGAGGTGAGCGGCGCTCTGTCCCCACCGTCCGC
ATCAGCTTATGTGAAGCTGGTACTGCTGGGACTGATTATGTGCGTGAGCCTGGCGGGTA
ACGCCATCTTGTCCCTGCTGGTGCTCAAGGAGCGTGCCCTGCACAAGGCTCCTTACTAC
TTCCTGCTGGACCTGTGCCTGGCCGATGGCATACGCTCTGCCGTCTGCTTCCCCTTTGT
GCTGGCTTCTGTGCGCCACGGCTCTTCATGGACCTTCAGTGCACTCAGCTGCAAGATTG
TGGCCTTTATGGCCGTGCTCTTTTGCTTCCATGCGGCCTTCATGCTGTTCTGCATCAGC
GTCACCCGCTACATGGCCATCGCCCACCACCGCTTCTACGCCAAGCGCATGACACTCTG
GACATGCGCGGCTGTCATCTGCATGGCCTGGACCCTGTCTGTGGCCATGGCCTTCCCAC
CTGTCTTTGACGTGGGCACCTACAAGTTTATTCGGGAGGAGGACCAGTGCATCTTTGAG
CATCGCTACTTCAAGGCCAATGACACGCTGGGCTTCATGCTTATGTTGGCTGTGCTCAT
GGCAGCTACCCATGCTGTCTACGGCAAGCTGCTCCTCTTCGAGTATCGTCACCGCAAGA
TGAAGCCAGTGCAGATGGTGCCAGCCATCAGCCAGAACTGGACATTCCATGGTCCCGGG
GCCACCGGCCAGGCTGCTGCCAACTGGATCGCCGGCTTTGGCCGTGGGCCCATGCCACC
AACCCTGCTGGGTATCCGGCAGAATGGGCATGCAGCCAGCCGGCGGCTACTGGGCATGG
ACGAGGTCAAGGGTGAAAAGCAGCTGGGCCGCATGTTCTACGCGATCACACTGCTCTTT
CTGCTCCTCTGGTCACCCTACATCGTGGCCTGCTACTGGCGAGTGTTTGTGAAAGCCTG
TGCTGTGCCCCACCGCTACCTGGCCACTGCTGTTTGGATGAGCTTCGCCCAGGCTGCCG
TCAACCCAATTGTCTGCTTCCTGCTCAACAAGGACCTCAAGAAGTGCCTGAGGACTCAC
GCCCCCTGCGCGGCCGCACGGGGACGCACCCCACCCAGCCTGGGTCCCCAAGATGAGTC
CTGCACCACCGCCAGCTCCTCCCTGGCCAAGGACACTTCATCGTGA
(SEQ ID No: 53)

FIGS. 5I – 5J

I. Amino Acid sequence of the hSREB2- Enhanced Receptor

MANYSHAADNILQNLSPLTAFLKLTSLGFIIGVSVVGNLLISILLVKDKTLHRAPYYFL
LDLCCSDILRSAICFPFVFNSVKNGSTWTYGTLTCKVIAFLGVLSCFHTAFMLFCISVT
RYLAIAHHRFYTKRLTFWTCLAVICMVWTLSVAMAFPPVLDVGTYSFIREEDQCTFQHR
SFRANDSLGFMLLLALILLATQLVYLKLIFFVHDRRKMKPVQFVAAVSQNWTFHGPGAS
GQAAANWLAGFGRGPTPPTLLGIRQNANTTGRRRLLVLDEFKMEKRISRMFYIMTFLFL
TLWGPYLVACYWRVFARGPVVPGGFLTAAVWMSFAQAGINPFVCIFSNRELRRCFSTTL
LYCAAARGRTPPSLGPQDESCTTASSSLAKDTSS
(SEQ ID No: 54)

J. Nucleotide sequence of the hSREB2- Enhanced Receptor

ATGGCGAACTATAGCCATGCAGCTGACAACATTTTGCAAAATCTCTCGCCTCTAACAGC
CTTTCTGAAACTGACTTCCTTGGGTTTCATAATAGGAGTCAGCGTGGTGGGCAACCTCC
TGATCTCCATTTTGCTAGTGAAAGATAAGACCTTGCATAGAGCACCTTACTACTTCCTG
TTGGATCTTTGCTGTTCAGATATCCTCAGATCTGCAATTTGTTTCCCATTTGTGTTCAA
CTCTGTCAAAAATGGCTCTACCTGGACTTATGGACTCTGACTTGCAAAGTGATTGCCT
TTCTGGGGGTTTTGTCCTGTTTCCACACTGCTTTCATGCTCTTCTGCATCAGTGTCACC
AGATACTTAGCTATCGCCCATCACCGCTTCTATACAAAGAGGCTGACCTTTTGGACGTG
TCTGGCTGTGATCTGTATGGTGTGGACTCTGTCTGTGGCCATGGCATTTCCCCCGGTTT
TAGACGTGGGCACTTACTCATTCATTAGGGAGGAAGATCAATGCACCTTCCAACACCGC
TCCTTCAGGGCTAATGATTCCTTAGGATTTATGCTGCTTCTtGCTCTCATCCTCCTAGC
CACACAGCTTGTCTACCTCAAGCTGATATTTTCGTCCACGATCGAAGAAAAATGAAGC
CAGTCCAGTTTGTAGCAGCAGTCAGCCAGAACTGGACTTTTCATGGTCCTGGAGCCAGT
GGCCAGGCAGCTGCCAATTGGCTAGCAGGATTTGGAAGGGGTCCCACACCACCCACCTT
GCTGGGCATCAGGCAAAATGCAAACACCACAGGCAGAAGAAGGCTATTGGTCTTAGACG
AGTTCAAAATGGAGAAAAGAATCAGCAGAATGTTCTATATAATGACTTTTCTGTTTCTA
ACCTTGTGGGGCCCCTACCTGGTGGCCTGTTATTGGAGAGTTTTTGCAAGAGGGCCTGT
AGTACCAGGGGGATTTCTAACAGCTGCTGTCTGGATGAGTTTTGCCCAAGCAGGAATCA
ATCCTTTTGTCTGCATTTTCTCAAACAGGGAGCTGAGGCGCTGTTTCAGCACAACCCTT
CTTTACTGCGCGGCCGCACGGGGACGCACCCCACCCAGCCTGGGTCCCCAAGATGAGTC
CTGCACCACCGCCAGCTCCTCCCTGGCCAAGGACACTTCATCGTGA
(SEQ ID No: 55)

FIGS. 5K – 5L

K. Amino Acid sequence of the hGPR8- Enhanced Receptor

MQAAGHPEPLDSRGSFSLPTMGANVSQDNGTGHNATFSEPLPFLYVLLPAVYSGICAVG
LTGNTAVILVILRAPKMKTVTNVFILNLAVADGLFTLVLPVNIAEHLLQYWPFGELLCK
LVLAVDHYNIFSSIYFLAVMSVDRYLVVLATVRSRHMPWRTYRGAKVASLCVWLGVTVL
VLPFFSFAGVYSNELQVPSCGLSFPWPERVWFKASRVYTLVLGFVLPVCTICVLYTDLL
RRLRAVRLRSGAKALGKARRKVTVLVLVVLAVCLLCWTPFHLASVVALTTDLPQTPLVI
SMSYVITSLSYANSCLNPFLYAFLDDNFRKNFRSILRCAAARGRTPPSLGPQDESCTTA
SSSLAKDTSS
(SEQ ID No: 56)

L. Nucleotide sequence of the hGPR8- Enhanced Receptor

ATGCAGGCCGCTGGGCACCCAGAGCCCCTTGACAGCAGGGGCTCCTTCTCCCTCCCCAC
GATGGGTGCCAACGTCTCTCAGGACAATGGCACTGGCCACAATGCCACCTTCTCCGAGC
CACTGCCGTTCCTCTATGTGCTCCTGCCCGCCGTGTACTCCGGGATCTGTGCTGTGGGG
CTGACTGGCAACACGGCCGTCATCCTTGTAATCCTAAGGGCGCCCAAGATGAAGACGGT
GACCAACGTGTTCATCCTGAACCTGGCCGTCGCCGACGGGCTCTTCACGCTGGTACTGC
CCGTCAACATCGCGGAGCACCTGCTGCAGTACTGGCCCTTCGGGGAGCTGCTCTGCAAG
CTGGTGCTGGCCGTCGACCACTACAACATCTTCTCCAGCATCTACTTCCTAGCCGTGAT
GAGCGTGGACCGATACCTGGTGGTGCTGGCCACCGTGAGGTCCCGCCACATGCCCTGGC
GCACCTACCGGGGGGCGAAGGTCGCCAGCCTGTGTGTCTGGCTGGGCGTCACGGTCCTG
GTTCTGCCCTTCTTCTCTTTCGCTGGCGTCTACAGCAACGAGCTGCAGGTCCCAAGCTG
TGGGCTGAGCTTCCCGTGGCCCGAGCGGGTCTGGTTCAAGGCCAGCCGTGTCTACACTT
TGGTCCTGGGCTTCGTGCTGCCCGTGTGCACCATCTGTGTGCTCTACACAGACCTCCTG
CGCAGGCTGCGGGCCGTGCGGCTCCGCTCTGGAGCCAAGGCTCTAGGCAAGGCCAGGCG
GAAGGTGACCGTCCTGGTCCTCGTCGTGCTGGCCGTGTGCCTCCTCTGCTGGACGCCCT
TCCACCTGGCCTCTGTCGTGGCCCTGACCACGGACCTGCCCCAGACCCCACTGGTCATC
AGTATGTCCTACGTCATCACCAGCCTCAGCTACGCCAACTCGTGCCTGAACCCCTTCCT
CTACGCCTTTCTAGATGACAACTTCCGGAAGAACTTCCGCAGCATATTGCGGTGCGCGG
CCGCACGGGGACGCACCCCACCCAGCCTGGGTCCCCAAGATGAGTCCTGCACCACCGCC
AGCTCCTCCCTGGCCAAGGACACTTCATCGTGA
(SEQ ID No: 57)

FIGS. 5M – 5N

M. Amino Acid sequence of the hGPR22-Enhanced Receptor

MCFSPILEINMQSESNITVRDDIDDINTNMYQPLSYPLSFQVSLTGFLMLEIVLGLGSN
LTVLVLYCMKSNLINSVSNIITMNLHVLDVIICVGCIPLTIVILLLSLESNTALICCFH
EACVSFASVSTAINVFAITLDRYDISVKPANRILTMGRAVMLMISIWIFSFFSFLIPFI
EVNFFSLQSGNTWENKTLLCVSTNEYYTELGMYYHLLVQIPIFFFTVVVMLITYTKILQ
ALNIRIGTRFSTGQKKKARKKKTISLTTQHEATDMSQSSGGRNVVFGVRTSVSVIIALR
RAVKRHRERRERQKRVFRMSLLIISTFLLCWTPISVLNTTILCLGPSDLLVKLRLCFLV
MAYGTTIFHPLLYAFTRQKFQKVLKSKMKKRVVCAAARGRTPPSLGPQDESCTTASSSL
AKDTSS
(SEQ ID No: 58)

N. Nucleotide sequence of the hGPR22-Enhanced Receptor

ATGTGTTTTCTCCcaTTCTGGAAATCAACATGCAGTCTGAATCTAACATTACAGTGCG
AGATGACATTGATGACATCAACACCAATATGTACCAACCACTATCATATCCGTTAAGCT
TTCAAGTGTCTCTCACCGGATTTCTTATGTTAGAAATTGTGTTGGGACTTGGCAGCAAC
CTCACTGTATTGGTACTTTACTGCATGAAATCCAACTTAATCAACTCTGTCAGTAACAT
TATTACAATGAATCTTCATGTACTTGATGTAATAATTTGTGTGGGATGTATTCCTCTAA
CTATAGTTATCCTTCTGCTTTCACTGGAGAGTAACACTGCTCTCATTTGCTGTTTCCAT
GAGGCTTGTGTATCTTTTGCAAGTGTCTCAACAGCAATCAACGTTTTTGCTATCACTTT
GGACAGATATGACATCTCTGTAAAACCTGCAAACCGAATTCTGACAATGGGCAGAGCTG
TAATGTTAATGATATCCATTTGGATTTTTTCTTTTTTCTCTTTCCTGATTCCTTTTATT
GAGGTAAATTTTTCAGTCTTCAAAGTGGAAATACCTGGGAAAACAAGACACTTTTATG
TGTCAGTACAAATGAATACTACACTGAACTGGGAATGTATTATCACCTGTTAGTACAGA
TCCCAATATTCTTTTTCACTGTTGTAGTAATGTTAATCACATACACCAAAATACTTCAG
GCTCTTAATATTCGAATAGGCACAAGATTTTCAACAGGGCAGAAGAAGAAAGCAAGAAA
GAAAAGACAATTTCTCTAACCACACAACATGAGGCTACAGACATGTCACAAAGCAGTG
GTGGGAGAAATGTAGTCTTTGGTGTAAGAACTTCAGTTTCTGTAATAATTGCCCTCCGG
CGAGCTGTGAAACGACACCGTGAACGACGAGAAAGACAAAAGAGAGTCTTCAGGATGTC
TTTATTGATTATTTCTACATTTCTTCTCTGCTGGACACCAATTTCTGTTTTAAATACCA
CCATTTTATGTTTAGGCCCAAGTGACCTTTTAGTAAAATTAAGATTGTGTTTTTTAGTC
ATGGCTTATGGAACAACTATATTTCACCCTCTATTATATGCATTCACTAGACAAAAATT
TCAAAAGGTCTTGAAAAGTAAAATGAAAAGCGAGTTGTTTGTGCGGCCGCACGGGGAC
GCACCCCACCCAGCCTGGGTCCCCAAGATGAGTCCTGCACCACCGCCAGCTCCTCCCTG
GCCAAGGACACTTCATCGTGA
(SEQ ID No: 59)

FIGS. 6A – 6C

A. Amino acid sequence of the β₂AR-V2R chimera

MGQPGNGSAFLLAPNRSHAPDHDVTQQRDEVWVVGMGIVMSLIVLAIVFGNVLVITAI
AKFERLQTVTNYFITSLACADLVMGLAVVPFGAAHILMKMWTFGNFWCEFWTSIDVLC
VTASIETLCVIAVDRYFAITSPFKYQSLLTKNKARVIILMVWIVSGLTSFLPIQMHWYRAT
HQEAINCYANETCCDFFTNQAYAIASSIVSFYVPLVIMVFVYSRVFQEAKRQLQKIDKSE
GRFHVQNLSQVEQDGRTGHGLRRSSKFCLKEHKALKTLGIIMGTFTLCWLPFFIVNIVHV
IQDNLIRKEVYILLNWIGYVNSGFNPLIYCRSPDFRIAFQELLCARGRTPPSLGPQDESCTT
ASSSLAKDTSS (Seq. ID No. 60)

B. Amino acid sequence of the MOR-V2R chimera

MDSSTGPGNTSDCSDPLAQASCSPAPGSWLNLSHVDGNQSDPCGLNRTGLGGNDSLCP
QTGSPSMVTAITIMALYSIVCVVGLFGNFLVMYVIVRYTKMKTATNIYIFNLALADALAT
STLPFQSVNYLMGTWPFGTILCKIVISIDYYNMFTSIFTLCTMSVDRYIAVCHPVKALDFR
TPRNAKIVNVCNWILSSAIGLPVMFMATTKYRQGSIDCTLTFSHPTWYWENLLKICVFIF
AFIMPILIITVCYGLMILRLKSVRMLSGSKEKDRNLRRITRMVLVVVAVFIVCWTPIHIYVI
IKALITIPETTFQTVSWHFCIALGYTNSCLNPVLYAFLDENFKRCFREFCAAARGRTPPSL
GPQDESCTTASSSLAKDTSS (Seq. ID No. 61)

C. Amino acid sequence of the D1AR-V2R chimera

MAPNTSTMDEAGLPAERDFSFRILTACFLSLLILSTLLGNTLVCAAVIRFRHLRSKVTNFF
VISLAVSDLLVAVLVMPWKAVAEIAGFWPFGSFCNIWVAFDIMCSTASILNLCVISVDRY
WAISSPFQYERKMTPKAAFILISVAWTLSVLISFIPVQLSWHKAKPTWPLDGNFTSLEDTE
DDNCDTRLSRTYAISSSLISFYIPVAIMIVTYTSIYRIAQKQIRRISALERAAVHAKNCQTT
AGNGNPVECAQSESSFKMSFKRETKVLKTLSVIMGVFVCCWLPFFISNCMVPFCGSEET
QPFCIDSITFDVFVWFGWANSSLNPIIYAFNADFQKAFSTLLGCYRLCAAARGRTPPSLGP
QDESCTTASSSLAKDTSS (Seq. ID No. 62)

FIGS. 6D – 6F

D. Amino acid sequence of the 5HT1AR-V2R chimera

MDVLSPGQGNNTTSPPAPFETGGNTTGISDVTVSYQVITSLLLGTLIFCAVLGNACVVAA
IALERSLQNVANYLIGSLAVTDLMVSVLVLPMAALYQVLNKWTLGQVTCDLFIALDVL
CCTSSILHLCAIALDRYWAITDPIDYVNKRTPRRAAALISLTWLIGFLISIPPMLGWRTPED
RSDPDACTISKDHGYTIYSTFGAFYIPLLLMLVLYGRIFRAARFRIRKTVKKVEKTGADT
RHGASPAPQPKKSVNGESGSRNWRLGVESKAGGALCANGAVRQGDDGAALEVIEVHR
VGNSKEHLPLPSEAGPTPCAPASFERKNERNAEAKRKMALARERKTVKTLGIIMGTFILC
WLPFFIVALVLPFCESSCHMPTLLGAIINWLGYSNSLLNPVIYAYFNKDFQNAFKKIIKCN
FCAAARGRTPPSLGPQDESCTTASSSLAKDTSS
(Seq. ID No. 63)

E. Amino acid sequence of the β3AR-V2R chimera

MAPWPHENSSLAPWPDLPTLAPNTANTSGLPGVPWEAALAGALLALAVLATVGGNLLV
IVAIAWTPRLQTMTNVFVTSLAAADLVMGLLVVPPAATLALTGHWPLGATGCELWTSV
DVLCVTASIETLCALAVDRYLAVTNPLRYGALVTKRCARTAVVLVWVVSAAVSFAPIM
SQWWRVGADAEAQRCHSNPRCCAFASNMPYVLLSSSVSFYLPLLVMLFVYARVFVVA
TRQLRLLRGELGRFPPEESPPAPSRSLAPAPVGTCAPPEGVPACGRRPARLLPLREHRALC
TLGLIMGTFTLCWLPFFLANVLRALGGPSLVPGPAFLALNWLGYANSAFNPLIYCRSPDF
RSAFRRLLCRCAAARGRTPPSLGPQDESCTTASSSLAKDTSS
(Seq. ID No. 64)

F. Amino acid sequence of the Edg1R-V2R chimera

MGPTSVPLVKAHRSSVSDYVNYDIIVRHYNYTGKLNISADKENSIKLTSVVFILICCFIILE
NIFVLLTIWKTKKFHRPMYYFIGNLALSDLLAGVAYTANLLLSGATTYKLTPAQWFLRE
GSMFVALSASVFSLLAIAIERYITMLKMKLHNGSNNFRLFLLISACWVISLILGGLPIMGW
NCISALSSCSTVLPLYHKHYILFCTTVFTLLLLSIVILYCRIYSLVRTRSRRLTFRKNISKAS
RSSEKSLALLKTVIIVLSVFIACWAPLFILLLLDVGCKVKTCDILFRAEYFLVLAVLNSGT
NPIIYTLTNKEMRRAFIRIMSCCKCAAARGRTPPSLGPQDESCTTASSSLAKDTSS
(Seq. ID No. 65)

Bisindolylmaleimide III

RO-31-7549

SEQUENCE LISTING

```
<160> NUMBER OF SEQ ID NOS: 65

<210> SEQ ID NO 1
<211> LENGTH: 43
<212> TYPE: PRT
<213> ORGANISM: Homo sapiens

<400> SEQUENCE: 1

Asn Pro Ile Val Tyr Ala Phe Arg Ile Gln Lys Phe Arg Val Thr Phe
1               5                   10                  15

Leu Lys Ile Trp Asn Asp His Phe Arg Cys Gln Pro Ala Pro Pro Ile
            20                  25                  30

Asp Glu Asp Leu Pro Glu Glu Arg Pro Asp Asp
        35                  40

<210> SEQ ID NO 2
<211> LENGTH: 177
<212> TYPE: PRT
<213> ORGANISM: Homo sapiens

<400> SEQUENCE: 2

Asn Pro Ile Ile Tyr Pro Cys Ser Ser Lys Glu Phe Lys Arg Ala Phe
1               5                   10                  15

Val Arg Ile Leu Gly Cys Gln Cys Arg Gly Arg Gly Arg Arg Arg Arg
            20                  25                  30

Arg Arg Arg Arg Arg Leu Gly Gly Cys Ala Tyr Thr Tyr Arg Pro Trp
        35                  40                  45

Thr Arg Gly Gly Ser Leu Glu Arg Ser Gln Ser Arg Lys Asp Ser Leu
    50                  55                  60

Asp Asp Ser Gly Ser Cys Leu Ser Gly Ser Gln Arg Thr Leu Pro Ser
65                  70                  75                  80

Ala Ser Pro Ser Pro Gly Tyr Leu Gly Arg Gly Ala Pro Pro Pro Val
```

-continued

```
                85                  90                  95
Glu Leu Cys Ala Phe Pro Glu Trp Lys Ala Pro Gly Ala Leu Leu Ser
            100                 105                 110
Leu Pro Ala Pro Glu Pro Pro Gly Arg Arg Gly Arg His Asp Ser Gly
            115                 120                 125
Pro Leu Phe Thr Phe Lys Leu Leu Thr Glu Pro Glu Ser Pro Gly Thr
            130                 135                 140
Asp Gly Gly Ala Ser Asn Gly Gly Cys Glu Ala Ala Asp Val Ala
145                 150                 155                 160
Asn Gly Gln Pro Gly Phe Lys Ser Asn Met Pro Leu Ala Pro Gly Gln
                165                 170                 175
Phe

<210> SEQ ID NO 3
<211> LENGTH: 29
<212> TYPE: PRT
<213> ORGANISM: Homo sapiens

<400> SEQUENCE: 3

Asn Pro Val Ile Tyr Thr Ile Phe Asn His Asp Phe Arg Arg Ala Phe
1               5                   10                  15
Lys Lys Ile Leu Cys Arg Gly Asp Arg Lys Arg Ile Val
            20                  25

<210> SEQ ID NO 4
<211> LENGTH: 29
<212> TYPE: PRT
<213> ORGANISM: Homo sapiens

<400> SEQUENCE: 4

Asn Pro Val Ile Tyr Thr Ile Phe Asn Gln Asp Phe Arg Arg Ala Phe
1               5                   10                  15
Arg Arg Ile Leu Cys Arg Pro Trp Thr Gln Thr Ala Trp
            20                  25

<210> SEQ ID NO 5
<211> LENGTH: 30
<212> TYPE: PRT
<213> ORGANISM: Homo sapiens

<400> SEQUENCE: 5

Asn Pro Val Ile Tyr Thr Val Phe Asn Gln Asp Phe Arg Pro Ser Phe
1               5                   10                  15
Lys His Ile Leu Phe Arg Arg Arg Arg Gly Phe Arg Gln
            20                  25                  30

<210> SEQ ID NO 6
<211> LENGTH: 105
<212> TYPE: PRT
<213> ORGANISM: Homo sapiens

<400> SEQUENCE: 6

Asn Pro Ile Ile Tyr Cys Arg Ser Pro Asp Phe Arg Lys Ala Phe Gln
1               5                   10                  15
Gly Leu Leu Cys Cys Ala Arg Arg Ala Ala Arg Arg Arg His Ala Thr
            20                  25                  30
His Gly Asp Arg Pro Arg Ala Ser Gly Cys Leu Ala Arg Pro Gly Pro
        35                  40                  45
Pro Pro Ser Pro Gly Ala Ala Ser Asp Asp Asp Asp Asp Val Val
```

```
                50                  55                  60
Gly Ala Thr Pro Pro Ala Arg Leu Leu Glu Pro Trp Ala Gly Cys Asn
 65                  70                  75                  80

Gly Gly Ala Ala Ala Asp Ser Asp Ser Ser Leu Asp Glu Pro Cys Arg
                 85                  90                  95

Pro Gly Phe Ala Ser Glu Ser Lys Val
                100                 105

<210> SEQ ID NO 7
<211> LENGTH: 92
<212> TYPE: PRT
<213> ORGANISM: Homo sapiens

<400> SEQUENCE: 7

Asn Pro Leu Ile Tyr Cys Arg Ser Pro Asp Phe Arg Ile Ala Phe Gln
 1               5                  10                  15

Glu Leu Leu Cys Leu Arg Arg Ser Ser Leu Lys Ala Tyr Gly Asn Gly
                20                  25                  30

Tyr Ser Ser Asn Gly Asn Thr Gly Glu Gln Ser Gly Tyr His Val Glu
            35                  40                  45

Gln Glu Lys Glu Asn Lys Leu Leu Cys Glu Asp Leu Pro Gly Thr Glu
     50                  55                  60

Asp Phe Val Gly His Gln Gly Thr Val Pro Ser Asp Asn Ile Asp Ser
 65                  70                  75                  80

Gln Gly Arg Asn Cys Ser Thr Asn Asp Ser Leu Leu
                85                  90

<210> SEQ ID NO 8
<211> LENGTH: 120
<212> TYPE: PRT
<213> ORGANISM: Homo sapiens

<400> SEQUENCE: 8

Asn Pro Ile Ile Tyr Ala Phe Asn Ala Asp Phe Arg Lys Ala Phe Ser
 1               5                  10                  15

Thr Leu Leu Gly Cys Tyr Arg Leu Cys Pro Ala Thr Asn Asn Ala Ile
                20                  25                  30

Glu Thr Val Ser Ile Asn Asn Asn Gly Ala Ala Met Phe Ser Ser His
            35                  40                  45

His Glu Pro Arg Gly Ser Ile Ser Lys Glu Cys Asn Leu Val Tyr Leu
     50                  55                  60

Ile Pro His Ala Val Gly Ser Ser Glu Asp Leu Lys Lys Glu Glu Ala
 65                  70                  75                  80

Ala Gly Ile Ala Arg Pro Leu Glu Lys Leu Ser Pro Ala Leu Ser Val
                85                  90                  95

Ile Leu Asp Tyr Asp Thr Asp Val Ser Leu Glu Lys Ile Gln Pro Ile
                100                 105                 110

Thr Gln Asn Gly Gln His Pro Thr
            115                 120

<210> SEQ ID NO 9
<211> LENGTH: 22
<212> TYPE: PRT
<213> ORGANISM: Homo sapiens

<400> SEQUENCE: 9

Asn Pro Ile Ile Tyr Thr Thr Phe Asn Ile Glu Phe Arg Lys Ala Phe
 1               5                  10                  15
```

Leu Lys Ile Leu His Cys
            20

<210> SEQ ID NO 10
<211> LENGTH: 22
<212> TYPE: PRT
<213> ORGANISM: Homo sapiens

<400> SEQUENCE: 10

Asn Pro Val Ile Tyr Thr Thr Phe Asn Ile Glu Phe Arg Lys Ala Phe
1               5                   10                  15

Leu Lys Ile Leu Ser Cys
            20

<210> SEQ ID NO 11
<211> LENGTH: 24
<212> TYPE: PRT
<213> ORGANISM: Homo sapiens

<400> SEQUENCE: 11

Asn Pro Val Ile Tyr Thr Val Phe Asn Ala Glu Phe Arg Asn Val Phe
1               5                   10                  15

Arg Lys Ala Leu Arg Ala Cys Cys
            20

<210> SEQ ID NO 12
<211> LENGTH: 123
<212> TYPE: PRT
<213> ORGANISM: Homo sapiens

<400> SEQUENCE: 12

Asn Pro Val Ile Tyr Ala Phe Asn Ala Asp Phe Gln Lys Val Phe Ala
1               5                   10                  15

Gln Leu Leu Gly Cys Ser His Phe Cys Ser Arg Thr Pro Val Glu Thr
            20                  25                  30

Val Asn Ile Ser Asn Glu Leu Ile Ser Tyr Asn Gln Asp Ile Val Phe
        35                  40                  45

His Lys Glu Ile Ala Ala Ala Tyr Ile His Met Met Pro Asn Ala Val
    50                  55                  60

Thr Pro Gly Asn Arg Glu Val Asp Asn Asp Glu Glu Gly Pro Phe
65                  70                  75                  80

Asp Arg Met Phe Gln Ile Tyr Gln Thr Ser Pro Asp Gly Asp Pro Val
                85                  90                  95

Ala Glu Ser Val Trp Glu Leu Asp Cys Glu Gly Glu Ile Ser Leu Asp
            100                 105                 110

Lys Ile Thr Pro Phe Thr Pro Asn Gly Phe His
        115                 120

<210> SEQ ID NO 13
<211> LENGTH: 47
<212> TYPE: PRT
<213> ORGANISM: Homo sapiens

<400> SEQUENCE: 13

Asn Pro Met Cys Tyr Ala Leu Cys Asn Lys Ala Phe Arg Asp Thr Phe
1               5                   10                  15

Arg Leu Leu Leu Leu Cys Arg Trp Asp Lys Arg Trp Arg Lys Ile
            20                  25                  30

Pro Lys Arg Pro Gly Ser Val His Arg Thr Pro Ser Arg Gln Cys

```
              35                  40                  45

<210> SEQ ID NO 14
<211> LENGTH: 31
<212> TYPE: PRT
<213> ORGANISM: Homo sapiens

<400> SEQUENCE: 14

Asn Pro Ala Cys Tyr Ala Leu Cys Asn Ala Thr Phe Lys Lys Thr Phe
 1               5                  10                  15

Lys His Leu Leu Met Cys His Tyr Lys Asn Ile Gly Ala Thr Arg
            20                  25                  30

<210> SEQ ID NO 15
<211> LENGTH: 50
<212> TYPE: PRT
<213> ORGANISM: Homo sapiens

<400> SEQUENCE: 15

Asn Pro Val Cys Tyr Ala Leu Cys Asn Lys Thr Phe Arg Thr Thr Lys
 1               5                  10                  15

Met Leu Leu Cys Gln Cys Asp Lys Lys Arg Arg Lys Gln Gln
            20                  25                  30

Tyr Gln Gln Arg Gln Ser Val Ile Phe His Lys Arg Ala Pro Glu Gln
        35                  40                  45

Ala Leu
    50

<210> SEQ ID NO 16
<211> LENGTH: 31
<212> TYPE: PRT
<213> ORGANISM: Homo sapiens

<400> SEQUENCE: 16

Asn Pro Ala Cys Tyr Ala Leu Cys Asn Ala Thr Phe Lys Lys Thr Phe
 1               5                  10                  15

Arg His Leu Leu Leu Cys Gln Tyr Arg Asn Ile Gly Thr Ala Arg
            20                  25                  30

<210> SEQ ID NO 17
<211> LENGTH: 42
<212> TYPE: PRT
<213> ORGANISM: Homo sapiens

<400> SEQUENCE: 17

Asn Pro Ile Cys Tyr Ala Leu Cys Asn Arg Thr Phe Arg Lys Thr Phe
 1               5                  10                  15

Lys Met Leu Leu Leu Cys Arg Trp Lys Lys Lys Val Glu Glu Lys
            20                  25                  30

Leu Tyr Trp Gln Gly Asn Ser Lys Leu Pro
        35                  40

<210> SEQ ID NO 18
<211> LENGTH: 24
<212> TYPE: PRT
<213> ORGANISM: Homo sapiens

<400> SEQUENCE: 18

Asn Pro Val Ile Tyr Ala Tyr Phe Asn Lys Asp Phe Gln Asn Ala Phe
 1               5                  10                  15

Lys Lys Ile Ile Lys Cys Lys Phe
```

```
                                     20

<210> SEQ ID NO 19
<211> LENGTH: 26
<212> TYPE: PRT
<213> ORGANISM: Homo sapiens

<400> SEQUENCE: 19

Asn Pro Ile Ile Tyr Thr Met Ser Asn Glu Asp Phe Lys Gln Ala Phe
1               5                   10                  15

His Lys Leu Ile Arg Phe Lys Cys Thr Ser
            20                  25

<210> SEQ ID NO 20
<211> LENGTH: 24
<212> TYPE: PRT
<213> ORGANISM: Homo sapiens

<400> SEQUENCE: 20

Asn Pro Leu Leu Tyr Thr Ser Phe Asn Glu Asp Phe Lys Leu Ala Phe
1               5                   10                  15

Lys Lys Leu Ile Arg Cys Arg Glu
            20

<210> SEQ ID NO 21
<211> LENGTH: 37
<212> TYPE: PRT
<213> ORGANISM: Homo sapiens

<400> SEQUENCE: 21

Asn Pro Ile Ile Tyr Cys Leu Arg Asn Gln Glu Val Lys Arg Ala Leu
1               5                   10                  15

Cys Cys Ile Leu His Leu Tyr Gln His Gln Asp Pro Asp Pro Lys Lys
            20                  25                  30

Gly Ser Arg Asn Val
        35

<210> SEQ ID NO 22
<211> LENGTH: 27
<212> TYPE: PRT
<213> ORGANISM: Homo sapiens

<400> SEQUENCE: 22

Asn Pro Leu Ile Tyr Thr Leu Arg Asn Met Glu Val Lys Gly Ala Leu
1               5                   10                  15

Arg Arg Leu Leu Gly Lys Gly Arg Glu Val Gly
            20                  25

<210> SEQ ID NO 23
<211> LENGTH: 62
<212> TYPE: PRT
<213> ORGANISM: Homo sapiens

<400> SEQUENCE: 23

Asn Pro Leu Phe Tyr Gly Phe Leu Gly Lys Lys Phe Lys Arg Tyr Phe
1               5                   10                  15

Leu Gln Leu Leu Lys Tyr Ile Pro Pro Lys Ala Lys Ser His Ser Asn
            20                  25                  30

Leu Ser Thr Lys Met Ser Thr Leu Ser Tyr Arg Pro Ser Asp Asn Val
        35                  40                  45

Ser Ser Ser Thr Lys Lys Pro Ala Pro Cys Phe Glu Val Glu
```

```
<210> SEQ ID NO 24
<211> LENGTH: 50
<212> TYPE: PRT
<213> ORGANISM: Homo sapiens

<400> SEQUENCE: 24

Asn Pro Phe Leu Tyr Cys Phe Val Gly Asn Arg Phe Gln Gln Lys Leu
1               5                   10                  15

Arg Ser Val Phe Arg Val Pro Ile Thr Trp Leu Gln Gly Lys Arg Glu
            20                  25                  30

Ser Met Ser Cys Arg Lys Ser Ser Leu Arg Glu Met Glu Thr Phe
        35                  40                  45

Val Ser
    50

<210> SEQ ID NO 25
<211> LENGTH: 50
<212> TYPE: PRT
<213> ORGANISM: Homo sapiens

<400> SEQUENCE: 25

Asn Pro Leu Ile Tyr Ala Phe Ile Gly Gln Lys Phe Arg His Gly Leu
1               5                   10                  15

Leu Lys Ile Leu Ala Ile His Gly Leu Ser Lys Asp Ser Leu Pro Lys
            20                  25                  30

Asp Ser Arg Pro Ser Phe Val Gly Ser Ser Ser Gly His Thr Ser Thr
        35                  40                  45

Thr Leu
    50

<210> SEQ ID NO 26
<211> LENGTH: 67
<212> TYPE: PRT
<213> ORGANISM: Homo sapiens

<400> SEQUENCE: 26

Asn Pro Leu Ile Tyr Ala Phe Ala Gly Glu Lys Phe Arg Arg Tyr Leu
1               5                   10                  15

Tyr His Leu Tyr Gly Lys Cys Leu Ala Val Leu Cys Gly Arg Ser Val
            20                  25                  30

His Val Asp Phe Ser Ser Glu Ser Gln Arg Ser Arg His Gly Ser
        35                  40                  45

Val Leu Ser Ser Asn Phe Thr Tyr His Thr Ser Asp Gly Asp Ala Leu
    50                  55                  60

Leu Leu Leu
65

<210> SEQ ID NO 27
<211> LENGTH: 59
<212> TYPE: PRT
<213> ORGANISM: Homo sapiens

<400> SEQUENCE: 27

Asn Pro Ile Leu Tyr Asn Leu Val Ser Ala Asn Phe Arg His Ile Phe
1               5                   10                  15

Leu Ala Thr Leu Ala Cys Leu Cys Pro Val Trp Arg Arg Arg Arg Lys
            20                  25                  30
```

-continued

Arg Pro Ala Phe Ser Arg Lys Ala Asp Ser Val Ser Ser Asn His Thr
                35                  40                  45

Leu Ser Ser Asn Ala Thr Arg Glu Thr Leu Tyr
     50                  55

<210> SEQ ID NO 28
<211> LENGTH: 107
<212> TYPE: PRT
<213> ORGANISM: Homo sapiens

<400> SEQUENCE: 28

Asn Pro Ile Ile Tyr Cys Cys Leu Asn Asp Arg Phe Arg Leu Gly Phe
  1               5                  10                  15

Lys His Ala Phe Arg Cys Cys Pro Phe Ile Ser Ala Gly Asp Tyr Glu
                 20                  25                  30

Gly Leu Glu Met Lys Ser Thr Arg Tyr Leu Gln Thr Gln Gly Ser Val
                35                  40                  45

Tyr Lys Val Ser Arg Leu Glu Thr Thr Ile Ser Thr Val Val Gly Ala
     50                  55                  60

His Glu Glu Pro Glu Asp Gly Pro Lys Ala Thr Pro Ser Ser Leu
 65                  70                  75                  80

Asp Leu Thr Ser Asn Cys Ser Ser Arg Ser Asp Ser Lys Thr Met Thr
                 85                  90                  95

Glu Ser Phe Ser Phe Ser Ser Asn Val Leu Ser
                100                 105

<210> SEQ ID NO 29
<211> LENGTH: 51
<212> TYPE: PRT
<213> ORGANISM: Homo sapiens

<400> SEQUENCE: 29

Asn Pro Trp Ile Tyr Ala Ser Phe Ser Ser Val Ser Ser Glu Leu
  1               5                  10                  15

Arg Ser Leu Leu Cys Cys Ala Arg Gly Arg Thr Pro Pro Ser Leu Gly
                 20                  25                  30

Pro Gln Asp Glu Ser Cys Thr Thr Ala Ser Ser Ser Leu Ala Lys Asp
                 35                  40                  45

Thr Ser Ser
     50

<210> SEQ ID NO 30
<211> LENGTH: 83
<212> TYPE: PRT
<213> ORGANISM: Homo sapiens

<400> SEQUENCE: 30

Asn Pro Val Ile Tyr Asn Leu Met Ser Gln Lys Phe Arg Ala Ala Phe
  1               5                  10                  15

Arg Lys Leu Cys Asn Cys Lys Gln Lys Pro Thr Glu Lys Pro Ala Asn
                 20                  25                  30

Tyr Ser Val Ala Leu Asn Tyr Ser Val Ile Lys Glu Ser Asp His Phe
                 35                  40                  45

Ser Thr Glu Leu Asp Asp Ile Thr Val Thr Asp Thr Tyr Leu Ser Ala
     50                  55                  60

Thr Lys Val Ser Phe Asp Asp Thr Cys Leu Ala Ser Glu Val Ser Phe
 65                  70                  75                  80

Ser Gln Ser

<210> SEQ ID NO 31
<211> LENGTH: 65
<212> TYPE: PRT
<213> ORGANISM: Homo sapiens

<400> SEQUENCE: 31

Asn Pro Trp Ile Tyr Met Leu Phe Thr Gly His Leu Phe His Glu Leu
1               5                   10                  15

Val Gln Arg Phe Leu Cys Cys Ser Ala Ser Tyr Leu Lys Gly Arg Arg
            20                  25                  30

Leu Gly Glu Thr Ser Ala Ser Lys Lys Ser Asn Ser Ser Ser Phe Val
        35                  40                  45

Leu Ser His Arg Ser Ser Gln Arg Ser Cys Ser Gln Pro Ser Thr
    50                  55                  60

Ala
65

<210> SEQ ID NO 32
<211> LENGTH: 75
<212> TYPE: PRT
<213> ORGANISM: Homo sapiens

<400> SEQUENCE: 32

Asn Pro Val Leu Tyr Ser Leu Met Ser Ser Arg Phe Arg Glu Thr Phe
1               5                   10                  15

Gln Glu Ala Leu Cys Leu Gly Ala Cys Cys His Arg Leu Arg Pro Arg
            20                  25                  30

His Ser Ser His Ser Leu Ser Arg Met Thr Thr Gly Ser Thr Leu Cys
        35                  40                  45

Asp Val Gly Ser Leu Gly Ser Trp Val His Pro Leu Ala Gly Asn Asp
    50                  55                  60

Gly Pro Glu Ala Gln Gln Glu Thr Asp Pro Ser
65                  70                  75

<210> SEQ ID NO 33
<211> LENGTH: 62
<212> TYPE: PRT
<213> ORGANISM: Homo sapiens

<400> SEQUENCE: 33

Asn Pro Leu Val Tyr Cys Phe Met His Arg Arg Phe Arg Gln Ala Cys
1               5                   10                  15

Leu Glu Thr Cys Ala Arg Cys Cys Pro Arg Pro Pro Arg Ala Arg Pro
            20                  25                  30

Arg Ala Leu Pro Asp Glu Asp Pro Pro Thr Pro Ser Ile Ala Ser Leu
        35                  40                  45

Ser Arg Leu Ser Tyr Thr Thr Ile Ser Phe Leu Gly Pro Gly
    50                  55                  60

<210> SEQ ID NO 34
<211> LENGTH: 82
<212> TYPE: PRT
<213> ORGANISM: Homo sapiens

<400> SEQUENCE: 34

Asn Pro Leu Val Tyr Ala Leu Ala Ser Arg His Phe Arg Ala Arg Phe
1               5                   10                  15

Arg Arg Leu Trp Pro Cys Gly Arg Arg Arg Arg His Arg Ala Arg Arg

```
                    20                  25                  30

Ala Leu Arg Arg Val Arg Pro Ala Ser Ser Gly Pro Pro Gly Cys Pro
            35                  40                  45

Gly Asp Ala Arg Pro Ser Gly Arg Leu Leu Ala Gly Gly Gln Gly
    50                  55                  60

Pro Glu Pro Arg Glu Gly Pro Val His Gly Gly Glu Ala Ala Arg Gly
65                  70                  75                  80

Pro Glu

<210> SEQ ID NO 35
<211> LENGTH: 76
<212> TYPE: PRT
<213> ORGANISM: Homo sapiens

<400> SEQUENCE: 35

Asn Pro Ile Ile Tyr Thr Leu Thr Asn Lys Glu Met Arg Arg Ala Phe
1               5                   10                  15

Ile Arg Ile Met Ser Cys Cys Lys Cys Pro Ser Gly Asp Ser Ala Gly
            20                  25                  30

Lys Phe Lys Arg Pro Ile Ile Ala Gly Met Glu Phe Ser Arg Ser Lys
        35                  40                  45

Ser Asp Asn Ser Ser His Pro Gln Lys Asp Glu Gly Asp Asn Pro Glu
    50                  55                  60

Thr Ile Met Ser Ser Gly Asn Val Asn Ser Ser Ser
65                  70                  75

<210> SEQ ID NO 36
<211> LENGTH: 80
<212> TYPE: PRT
<213> ORGANISM: Homo sapiens

<400> SEQUENCE: 36

Asn Pro Ile Ile Tyr Ala Leu Arg Ser Lys Asp Leu Arg His Ala Phe
1               5                   10                  15

Arg Ser Met Phe Pro Ser Cys Glu Gly Thr Ala Gln Pro Leu Asp Asn
            20                  25                  30

Ser Met Gly Asp Ser Asp Cys Leu His Lys His Ala Asn Asn Ala Ala
        35                  40                  45

Ser Val His Arg Ala Ala Glu Ser Cys Ile Lys Ser Thr Val Lys Ile
    50                  55                  60

Ala Lys Val Thr Met Ser Val Ser Thr Asp Thr Ser Ala Glu Ala Leu
65                  70                  75                  80

<210> SEQ ID NO 37
<211> LENGTH: 59
<212> TYPE: PRT
<213> ORGANISM: Homo sapiens

<400> SEQUENCE: 37

Asn Pro Val Leu Tyr Ala Phe Leu Asp Glu Asn Phe Lys Arg Cys Phe
1               5                   10                  15

Arg Gln Leu Cys Arg Lys Pro Cys Gly Arg Pro Asp Pro Ser Ser Phe
            20                  25                  30

Ser Arg Pro Arg Glu Ala Thr Ala Arg Glu Arg Val Thr Ala Cys Thr
        35                  40                  45

Pro Ser Asp Gly Pro Gly Gly Gly Arg Ala Ala
    50                  55
```

<210> SEQ ID NO 38
<211> LENGTH: 58
<212> TYPE: PRT
<213> ORGANISM: Homo sapiens

<400> SEQUENCE: 38

```
Asp Pro Phe Val Tyr Tyr Phe Val Ser His Asp Phe Arg Asp His Ala
  1               5                  10                  15

Lys Asn Ala Leu Leu Cys Arg Ser Val Arg Thr Val Lys Gln Met Gln
             20                  25                  30

Val Ser Leu Thr Ser Lys Lys His Ser Arg Lys Ser Ser Ser Tyr Ser
         35                  40                  45

Ser Ser Ser Thr Thr Val Lys Thr Ser Tyr
         50                  55
```

<210> SEQ ID NO 39
<211> LENGTH: 66
<212> TYPE: PRT
<213> ORGANISM: Homo sapiens

<400> SEQUENCE: 39

```
Asn Gly Glu Val Gln Ala Glu Leu Arg Arg Lys Trp Arg Arg Trp His
  1               5                  10                  15

Leu Gln Gly Val Leu Gly Trp Ser Ser Lys Ser Gln His Pro Trp Gly
             20                  25                  30

Gly Ser Asn Gly Ala Thr Cys Ser Thr Gln Val Ser Met Leu Thr Arg
         35                  40                  45

Val Ser Pro Ser Ala Arg Arg Ser Ser Ser Phe Gln Ala Glu Val Ser
     50                  55                  60

Leu Val
65
```

<210> SEQ ID NO 40
<211> LENGTH: 371
<212> TYPE: PRT
<213> ORGANISM: Homo sapiens

<400> SEQUENCE: 40

```
Met Leu Met Ala Ser Thr Thr Ser Ala Val Pro Gly His Pro Ser Leu
  1               5                  10                  15

Pro Ser Leu Pro Ser Asn Ser Ser Gln Glu Arg Pro Leu Asp Thr Arg
             20                  25                  30

Asp Pro Leu Leu Ala Arg Ala Glu Leu Ala Leu Leu Ser Ile Val Phe
         35                  40                  45

Val Ala Val Ala Leu Ser Asn Gly Leu Val Leu Ala Ala Leu Ala Arg
     50                  55                  60

Arg Gly Arg Arg Gly His Trp Ala Pro Ile His Val Phe Ile Gly His
 65                  70                  75                  80

Leu Cys Leu Ala Asp Leu Ala Val Ala Leu Phe Gln Val Leu Pro Gln
             85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
            115                 120                 125

Met Ile Leu Ala Met Thr Leu Asp Arg His Arg Ala Ile Cys Arg Pro
        130                 135                 140

Met Leu Ala Tyr Arg His Gly Ser Gly Ala His Trp Asn Arg Pro Val
```

```
                145                 150                 155                 160
Leu Val Ala Trp Ala Phe Ser Leu Leu Ser Leu Pro Gln Leu Phe
                    165                 170                 175
Ile Phe Ala Gln Arg Asn Val Glu Gly Gly Ser Gly Val Thr Asp Cys
                180                 185                 190
Trp Ala Cys Phe Ala Glu Pro Trp Gly Arg Arg Thr Tyr Val Thr Trp
            195                 200                 205
Ile Ala Leu Met Val Phe Val Ala Pro Thr Leu Gly Ile Ala Ala Cys
        210                 215                 220
Gln Val Leu Ile Phe Arg Glu Ile His Ala Ser Leu Val Pro Gly Pro
225                 230                 235                 240
Ser Glu Arg Pro Gly Gly Arg Arg Gly Arg Arg Thr Gly Ser Pro
                245                 250                 255
Gly Glu Gly Ala His Val Ser Ala Ala Val Ala Lys Thr Val Arg Met
                260                 265                 270
Thr Leu Val Ile Val Val Tyr Val Leu Cys Trp Ala Pro Phe Phe
            275                 280                 285
Leu Val Gln Leu Trp Ala Ala Trp Asp Pro Glu Ala Pro Leu Glu Gly
        290                 295                 300
Ala Pro Phe Val Leu Leu Met Leu Leu Ala Ser Leu Asn Ser Cys Thr
305                 310                 315                 320
Asn Pro Trp Ile Tyr Ala Ser Phe Ser Ser Ser Val Ser Ser Glu Leu
                325                 330                 335
Arg Ser Leu Leu Cys Cys Ala Arg Gly Arg Thr Pro Pro Ser Leu Gly
                340                 345                 350
Pro Gln Asp Glu Ser Cys Thr Thr Ala Ser Ser Ser Leu Ala Lys Asp
                355                 360                 365
Thr Ser Ser
    370

<210> SEQ ID NO 41
<211> LENGTH: 515
<212> TYPE: PRT
<213> ORGANISM: Golden hamster

<400> SEQUENCE: 41

Met Asn Pro Asp Leu Asp Thr Gly His Asn Thr Ser Ala Pro Ala Gln
1               5                   10                  15
Trp Gly Glu Leu Lys Asp Ala Asn Phe Thr Gly Pro Asn Gln Thr Ser
                20                  25                  30
Ser Asn Ser Thr Leu Pro Gln Leu Asp Val Thr Arg Ala Ile Ser Val
            35                  40                  45
Gly Leu Val Leu Gly Ala Phe Ile Leu Phe Ala Ile Val Gly Asn Ile
        50                  55                  60
Leu Val Ile Leu Ser Val Ala Cys Asn Arg His Leu Arg Thr Pro Thr
65                  70                  75                  80
Asn Tyr Phe Ile Val Asn Leu Ala Ile Ala Asp Leu Leu Leu Ser Phe
                85                  90                  95
Thr Val Leu Pro Phe Ser Ala Thr Leu Glu Val Leu Gly Tyr Trp Val
            100                 105                 110
Leu Gly Arg Ile Phe Cys Asp Ile Trp Ala Ala Val Asp Val Leu Cys
        115                 120                 125
Cys Thr Ala Ser Ile Leu Ser Leu Cys Ala Ile Ser Ile Asp Glu Tyr
    130                 135                 140
```

```
Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Met Arg Ile Leu Gly Cys Gln Cys Arg
        355                 360                 365

Ser Gly Arg Arg Arg Arg Arg Arg Leu Gly Ala Cys Ala Tyr
    370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
                405                 410                 415

Arg Thr Leu Pro Ser Ala Ser Pro Ser Pro Gly Tyr Leu Gly Arg Gly
            420                 425                 430

Ala Gln Pro Pro Leu Glu Leu Cys Ala Tyr Pro Glu Trp Lys Ser Gly
        435                 440                 445

Ala Leu Leu Ser Leu Pro Glu Pro Pro Gly Arg Arg Gly Arg Leu Asp
    450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
            500                 505                 510

Gly His Phe
        515

<210> SEQ ID NO 42
<211> LENGTH: 515
<212> TYPE: PRT
<213> ORGANISM: Golden hamster

<400> SEQUENCE: 42
```

```
Met Asn Pro Asp Leu Asp Thr Gly His Asn Thr Ser Ala Pro Ala Gln
  1               5                  10                  15

Trp Gly Glu Leu Lys Asp Ala Asn Phe Thr Gly Pro Asn Gln Thr Ser
             20                  25                  30

Ser Asn Ser Thr Leu Pro Gln Leu Asp Val Thr Arg Ala Ile Ser Val
         35                  40                  45

Gly Leu Val Leu Gly Ala Phe Ile Leu Phe Ala Ile Val Gly Asn Ile
     50                  55                  60

Leu Val Ile Leu Ser Val Ala Cys Asn Arg His Leu Arg Thr Pro Thr
 65                  70                  75                  80

Asn Tyr Phe Ile Val Asn Leu Ala Ile Ala Asp Leu Leu Leu Ser Phe
                 85                  90                  95

Thr Val Leu Pro Phe Ser Ala Thr Leu Glu Val Leu Gly Tyr Trp Val
                100                 105                 110

Leu Gly Arg Ile Phe Cys Asp Ile Trp Ala Ala Val Asp Val Leu Cys
             115                 120                 125

Cys Thr Ala Ser Ile Leu Ser Leu Cys Ala Ile Ser Ile Asp Ala Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                 165                 170                 175

Ser Ile Gly Pro Leu Leu Gly Trp Lys Glu Pro Ala Pro Asn Asp Asp
             180                 185                 190

Lys Glu Cys Gly Val Thr Glu Glu Pro Phe Tyr Ala Leu Phe Ser Ser
             195                 200                 205

Leu Gly Ser Phe Tyr Ile Pro Leu Ala Val Ile Leu Val Met Tyr Cys
         210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                 245                 250                 255

Ser Lys Asn Phe His Glu Asp Thr Leu Ser Ser Thr Lys Ala Lys Gly
             260                 265                 270

His Asn Pro Arg Ser Ser Ile Ala Val Lys Leu Phe Lys Phe Ser Arg
             275                 280                 285

Glu Lys Lys Ala Ala Lys Thr Leu Gly Ile Val Val Gly Met Phe Ile
             290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                 325                 330                 335

Gly Tyr Phe Asn Ser Cys Leu Asn Pro Ile Ile Tyr Pro Cys Ser Ser
             340                 345                 350

Lys Glu Phe Lys Arg Ala Phe Met Arg Ile Leu Gly Cys Gln Cys Arg
             355                 360                 365

Ser Gly Arg Arg Arg Arg Arg Arg Arg Leu Gly Ala Cys Ala Tyr
         370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
             405                 410                 415
```

```
Arg Thr Leu Pro Ser Ala Ser Pro Ser Pro Gly Tyr Leu Gly Arg Gly
            420                 425                 430

Ala Gln Pro Pro Leu Glu Leu Cys Ala Tyr Pro Glu Trp Lys Ser Gly
            435                 440                 445

Ala Leu Leu Ser Leu Pro Glu Pro Pro Gly Arg Arg Gly Arg Leu Asp
            450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
            485                 490                 495

Leu Ala Asn Gly Gln Pro Gly Phe Lys Ser Asn Met Pro Leu Ala Pro
            500                 505                 510

Gly His Phe
        515

<210> SEQ ID NO 43
<211> LENGTH: 515
<212> TYPE: PRT
<213> ORGANISM: Golden hamster

<400> SEQUENCE: 43

Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
            20                  25                  30

Ser Asn Ser Thr Leu Pro Gln Leu Asp Val Thr Arg Ala Ile Ser Val
            35                  40                  45

Gly Leu Val Leu Gly Ala Phe Ile Leu Phe Ala Ile Val Gly Asn Ile
        50                  55                  60

Leu Val Ile Leu Ser Val Ala Cys Asn Arg His Leu Arg Thr Pro Thr
65              70                  75                  80

Asn Tyr Phe Ile Val Asn Leu Ala Ile Ala Asp Leu Leu Leu Ser Phe
            85                  90                  95

Thr Val Leu Pro Phe Ser Ala Thr Leu Glu Val Leu Gly Tyr Trp Val
            100                 105                 110

Leu Gly Arg Ile Phe Cys Asp Ile Trp Ala Ala Val Asp Val Leu Cys
            115                 120                 125

Cys Thr Ala Ser Ile Leu Ser Leu Cys Ala Ile Ser Ile Asp His Tyr
        130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
            165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
            195                 200                 205

Leu Gly Ser Phe Tyr Ile Pro Leu Ala Val Ile Leu Val Met Tyr Cys
        210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
            245                 250                 255

Ser Lys Asn Phe His Glu Asp Thr Leu Ser Ser Thr Lys Ala Lys Gly
            260                 265                 270
```

```
His Asn Pro Arg Ser Ser Ile Ala Val Lys Leu Phe Lys Phe Ser Arg
            275                 280                 285

Glu Lys Lys Ala Ala Lys Thr Leu Gly Ile Val Val Gly Met Phe Ile
        290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Met Arg Ile Leu Gly Cys Gln Cys Arg
        355                 360                 365

Ser Gly Arg Arg Arg Arg Arg Arg Arg Leu Gly Ala Cys Ala Tyr
            370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
                405                 410                 415

Arg Thr Leu Pro Ser Ala Ser Pro Ser Pro Gly Tyr Leu Gly Arg Gly
            420                 425                 430

Ala Gln Pro Pro Leu Glu Leu Cys Ala Tyr Pro Glu Trp Lys Ser Gly
        435                 440                 445

Ala Leu Leu Ser Leu Pro Glu Pro Pro Gly Arg Arg Gly Arg Leu Asp
    450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
            500                 505                 510

Gly His Phe
        515

<210> SEQ ID NO 44
<211> LENGTH: 515
<212> TYPE: PRT
<213> ORGANISM: Golden hamster

<400> SEQUENCE: 44

Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
            20                  25                  30

Ser Asn Ser Thr Leu Pro Gln Leu Asp Val Thr Arg Ala Ile Ser Val
        35                  40                  45

Gly Leu Val Leu Gly Ala Phe Ile Leu Phe Ala Ile Val Gly Asn Ile
    50                  55                  60

Leu Val Ile Leu Ser Val Ala Cys Asn Arg His Leu Arg Thr Pro Thr
65                  70                  75                  80

Asn Tyr Phe Ile Val Asn Leu Ala Ile Ala Asp Leu Leu Leu Ser Phe
                85                  90                  95

Thr Val Leu Pro Phe Ser Ala Thr Leu Glu Val Leu Gly Tyr Trp Val
            100                 105                 110

Leu Gly Arg Ile Phe Cys Asp Ile Trp Ala Ala Val Asp Val Leu Cys
```

```
            115                 120                 125
Cys Thr Ala Ser Ile Leu Ser Leu Cys Ala Ile Ser Ile Asp Asn Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
                245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
                325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Met Arg Ile Leu Gly Cys Gln Cys Arg
        355                 360                 365

Ser Gly Arg Arg Arg Arg Arg Arg Leu Gly Ala Cys Ala Tyr
    370                 375                 380

Thr Tyr Arg Pro Trp Thr Arg Gly Gly Ser Leu Glu Arg Ser Gln Ser
385                 390                 395                 400

Arg Lys Asp Ser Leu Asp Asp Ser Gly Ser Cys Met Ser Gly Ser Gln
                405                 410                 415

Arg Thr Leu Pro Ser Ala Ser Pro Ser Pro Gly Tyr Leu Gly Arg Gly
            420                 425                 430

Ala Gln Pro Pro Leu Glu Leu Cys Ala Tyr Pro Glu Trp Lys Ser Gly
        435                 440                 445

Ala Leu Leu Ser Leu Pro Glu Pro Pro Gly Arg Arg Gly Arg Leu Asp
    450                 455                 460

Ser Gly Pro Leu Phe Thr Phe Lys Leu Leu Gly Glu Pro Glu Ser Pro
465                 470                 475                 480

Gly Thr Glu Gly Asp Ala Ser Asn Gly Gly Cys Asp Ala Thr Thr Asp
                485                 490                 495

Leu Ala Asn Gly Gln Pro Gly Phe Lys Ser Asn Met Pro Leu Ala Pro
            500                 505                 510

Gly His Phe
515

<210> SEQ ID NO 45
```

-continued

```
<211> LENGTH: 359
<212> TYPE: PRT
<213> ORGANISM: Rattus norvegicus

<400> SEQUENCE: 45

Met Ala Leu Asn Ser Ser Ala Glu Asp Gly Ile Lys Arg Ile Gln Asp
 1               5                  10                  15

Asp Cys Pro Lys Ala Gly Arg His Ser Tyr Ile Phe Val Met Ile Pro
                20                  25                  30

Thr Leu Tyr Ser Ile Ile Phe Val Val Gly Ile Phe Gly Asn Ser Leu
            35                  40                  45

Val Val Ile Val Ile Tyr Phe Tyr Met Lys Leu Lys Thr Val Ala Ser
 50                  55                  60

Val Phe Leu Leu Asn Leu Ala Leu Ala Asp Leu Cys Phe Leu Leu Thr
 65                  70                  75                  80

Cys Pro Leu Trp Ala Val Tyr Thr Ala Met Glu Tyr Arg Trp Pro Phe
                85                  90                  95

Gly Asn His Leu Cys Lys Ile Ala Ser Ala Ser Val Thr Phe Asn Leu
               100                 105                 110

Tyr Ala Ser Val Phe Leu Leu Thr Cys Leu Ser Ile Asp Arg Tyr Leu
            115                 120                 125

Ala Ile Val His Pro Met Lys Ser Arg Leu Arg Arg Thr Met Leu Val
130                 135                 140

Ala Lys Val Thr Cys Ile Ile Ile Trp Leu Met Ala Gly Leu Ala Ser
145                 150                 155                 160

Leu Pro Ala Val Ile His Arg Asn Val Tyr Phe Ile Glu Asn Thr Asn
                165                 170                 175

Ile Thr Val Cys Ala Phe His Tyr Glu Ser Arg Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Arg
225                 230                 235                 240

Ile Ile Met Ala Ile Val Leu Phe Phe Phe Ser Trp Val Pro His
                245                 250                 255

Gln Ile Phe Thr Phe Leu Asp Val Leu Ile Gln Leu Gly Val Ile His
            260                 265                 270

Asp Cys Lys Ile Ser Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
    290                 295                 300

Leu Gly Lys Lys Phe Lys Lys Tyr Phe Leu Gln Leu Leu Lys Tyr Ile
305                 310                 315                 320

Pro Pro Lys Ala Lys Ser His Ser Ser Leu Ser Thr Lys Met Ser Thr
                325                 330                 335

Leu Ser Tyr Arg Pro Ser Asp Asn Met Ser Ser Ser Ala Lys Lys Pro
            340                 345                 350

Ala Ser Cys Phe Glu Val Glu
        355

<210> SEQ ID NO 46
<211> LENGTH: 346
<212> TYPE: PRT
```

<213> ORGANISM: Homo sapiens

<400> SEQUENCE: 46

```
Met Met Trp Gly Ala Gly Ser Pro Leu Ala Trp Leu Ser Ala Gly Ser
 1               5                  10                  15
Gly Asn Val Asn Val Ser Ser Val Gly Pro Ala Glu Gly Pro Thr Gly
             20                  25                  30
Pro Ala Ala Pro Leu Pro Ser Pro Lys Ala Trp Asp Val Val Leu Cys
         35                  40                  45
Ile Ser Gly Thr Leu Val Ser Cys Glu Asn Ala Leu Val Val Ala Ile
     50                  55                  60
Ile Val Gly Thr Pro Ala Phe Arg Ala Pro Met Phe Leu Leu Val Gly
 65                  70                  75                  80
Ser Leu Ala Val Ala Asp Leu Leu Ala Gly Leu Gly Leu Val Leu His
                 85                  90                  95
Phe Ala Val Phe Cys Ile Gly Ser Ala Glu Met Ser Leu Val Leu
             100                 105                 110
Val Gly Val Leu Ala Met Ala Phe Thr Ala Ser Ile Gly Ser Leu Leu
         115                 120                 125
Ala Ile Thr Val Asp Arg Tyr Leu Ser Leu Tyr Asn Ala Leu Thr Tyr
    130                 135                 140
Tyr Ser Glu Thr Thr Val Thr Arg Thr Tyr Val Met Leu Ala Leu Val
145                 150                 155                 160
Trp Gly Gly Ala Leu Gly Leu Gly Leu Leu Pro Val Leu Ala Trp Asn
                165                 170                 175
Cys Leu Asp Gly Leu Thr Thr Cys Gly Val Val Tyr Pro Leu Ser Lys
            180                 185                 190
Asn His Leu Val Val Leu Ala Ile Ala Phe Phe Met Val Phe Gly Ile
        195                 200                 205
Met Leu Gln Leu Tyr Ala Gln Ile Cys Arg Ile Val Cys Arg His Ala
    210                 215                 220
Gln Gln Ile Ala Leu Gln Arg His Leu Leu Pro Ala Ser His Tyr Val
225                 230                 235                 240
Ala Thr Arg Lys Gly Ile Ala Thr Leu Ala Val Val Leu Gly Ala Phe
                245                 250                 255
Ala Ala Cys Trp Leu Pro Phe Thr Val Tyr Cys Leu Leu Gly Asp Ala
            260                 265                 270
His Ser Pro Pro Leu Tyr Thr Tyr Leu Thr Leu Leu Pro Ala Thr Tyr
        275                 280                 285
Asn Ser Met Ile Asn Pro Ile Ile Tyr Ala Phe Arg Asn Gln Asp Val
    290                 295                 300
Gln Lys Val Leu Trp Ala Val Cys Cys Cys Ala Ala Ala Arg Gly
305                 310                 315                 320
Arg Thr Pro Pro Ser Leu Gly Pro Gln Asp Glu Ser Cys Thr Thr Ala
                325                 330                 335
Ser Ser Ser Leu Ala Lys Asp Thr Ser Ser
            340                 345
```

<210> SEQ ID NO 47
<211> LENGTH: 1041
<212> TYPE: DNA
<213> ORGANISM: Homo sapiens

<400> SEQUENCE: 47
atgatgtggg gtgcaggcag ccctctggcc tggctctcag ctggctcagg caacgtgaat    60

-continued

```
gtaagcagcg tgggcccagc agaggggccc acaggtccag ccgcaccact gccctcgcct      120
aaggcctggg atgtggtgct ctgcatctca ggcaccctgg tgtcctgcga gaatgcgcta      180
gtggtggcca tcatcgtggg cactcctgcc ttccgtgccc ccatgttcct gctggtgggc      240
agcctggccg tggcagacct gctggcaggc ctgggcctgg tcctgcactt gctgctgtc       300 ttctgcatcg gctcagcgga gatgagcctg gtgctggttg gcgtgctggc aatgcctttt      360
acygccagca tcggcagtct actggccatc actgtcgacc gctacctttc tctgtacaat      420
gccctcacct actattcaga gacaacagtg acacggacct atgtgatgct ggccttagtg      480
tggggaggtg ccctgggcct ggggctgctg cctgtgctgg cctggaactg cctggatggc      540
ctgaccacat gtggcgtggt ttatccactc tccaagaacc atctggtagt tctggccatt      600
gccttcttca tggtgtttgg catcatgctg cagctctacg cccaaatctg ccgcatcgtc      660
tgccgccatg cccagcagat tgcccttcag cggcacctgc tgcctgcctc ccactatgtg      720
gccacccgca agggcattgc cacactggcc gtggtgcttg gagcctttgc cgcctgctgg      780
ttgcccttca ctgtctactg cctgctgggt gatgcccact ctccacctct ctacacctat      840
cttaccttgc tccctgccac ctacaactcc atgatcaacc ctatcatcta cgccttccgc      900
aaccaggatg tgcagaaagt gctgtgggct gtctgctgct gctgtgcggc cgcacgggga      960 cgcacccccac ccagcctggg tccccaagat gagtcctgca ccaccgccag ctcctccctg     1020
gccaaggaca cttcatcgtg a                                                1041
```

<210> SEQ ID NO 48
<211> LENGTH: 378
<212> TYPE: PRT
<213> ORGANISM: Homo sapiens

<400> SEQUENCE: 48

```
Met Asn Ala Ser Ala Ala Ser Leu Asn Asp Ser Gln Val Val Val
 1               5                  10                  15

Ala Ala Glu Gly Ala Ala Ala Ala Thr Ala Ala Gly Gly Pro Asp
             20                  25                  30

Thr Gly Glu Trp Gly Pro Ala Ala Ala Leu Gly Ala Gly Gly
         35                  40                  45

Gly Ala Asn Gly Ser Leu Glu Leu Ser Ser Gln Leu Ser Ala Gly Pro
     50                  55                  60

Pro Gly Leu Leu Leu Pro Ala Val Asn Pro Trp Asp Val Leu Leu Cys
 65                  70                  75                  80

Val Ser Gly Thr Val Ile Ala Gly Glu Asn Ala Leu Val Val Ala Leu
                     85                  90                  95

Ile Ala Ser Thr Pro Ala Leu Arg Thr Pro Met Phe Val Leu Val Gly
                    100                 105                 110

Ser Leu Ala Thr Ala Asp Leu Leu Ala Gly Cys Gly Leu Ile Leu His
                115                 120                 125

Phe Val Phe Gln Tyr Leu Val Pro Ser Glu Thr Val Ser Leu Leu Thr
                130                 135                 140

Val Gly Phe Leu Val Ala Ser Phe Ala Ala Ser Val Ser Ser Leu Leu
145                 150                 155                 160

Ala Ile Thr Val Asp Arg Tyr Leu Ser Leu Tyr Asn Ala Leu Thr Tyr
                    165                 170                 175

Tyr Ser Arg Arg Thr Leu Leu Gly Val His Leu Leu Leu Ala Ala Thr
                180                 185                 190
```

```
Trp Thr Val Ser Leu Gly Leu Gly Leu Leu Pro Val Leu Gly Trp Asn
            195                 200                 205

Cys Leu Ala Glu Arg Ala Ala Cys Ser Val Val Arg Pro Leu Ala Arg
        210                 215                 220

Ser His Val Ala Leu Leu Ser Ala Ala Phe Phe Met Val Phe Gly Ile
225                 230                 235                 240

Met Leu His Leu Tyr Val Arg Ile Cys Gln Val Val Trp Arg His Ala
                245                 250                 255

His Gln Ile Ala Leu Gln Gln His Cys Leu Ala Pro Pro His Leu Ala
            260                 265                 270

Ala Thr Arg Lys Gly Val Gly Thr Leu Ala Val Val Leu Gly Thr Phe
        275                 280                 285

Gly Ala Ser Trp Leu Pro Phe Ala Ile Tyr Cys Val Val Gly Ser His
290                 295                 300

Glu Asp Pro Ala Val Tyr Thr Tyr Ala Thr Leu Leu Pro Ala Thr Tyr
305                 310                 315                 320

Asn Ser Met Ile Asn Pro Ile Ile Tyr Ala Phe Arg Asn Gln Glu Ile
                325                 330                 335

Gln Arg Ala Leu Trp Leu Leu Leu Cys Gly Cys Ala Ala Ala Arg Gly
            340                 345                 350

Arg Thr Pro Pro Ser Leu Gly Pro Gln Asp Glu Ser Cys Thr Thr Ala
        355                 360                 365

Ser Ser Ser Leu Ala Lys Asp Thr Ser Ser
        370                 375

<210> SEQ ID NO 49
<211> LENGTH: 1137
<212> TYPE: DNA
<213> ORGANISM: Homo sapiens

<400> SEQUENCE: 49
atgaacgcga gcgccgcctc gctcaacgac tcccaggtgg tggtagtggc ggccgaagga      60
gcggcggcgg cggccacagc agcagggggg ccggacacgg gcgaatgggg accccctgct     120
gcggcggctc taggagccgg cggcggagct aatgggtctc tggagctgtc ctcgcagctg     180
tcggctgggc caccgggact cctgctgcca gcggtgaatc cgtgggacgt gctcctgtgc     240
gtgtcgggga cagtgatcgc tggagaaaac gcgctggtgg tggcgctcat cgcgtccact     300
ccggcgctgc gcacgcccat gttcgtgctg gtaggcagcc tggccaccgc tgacctgttg     360
gcgggctgtg gcctcatctt gcactttgtg ttccagtact tggtgccctc ggagactgtg     420
agtctgctca cggtgggctt cctcgtggcc tccttcgccg cctctgtcag cagcctgctg     480
gccattacgg tggaccgcta cctgtccctg tataacgcgc tcacctatta ctcgcgccgg     540
accctgttgg gcgtgcacct cctgcttgcc gccacttgga ccgtgtccct aggcctgggg     600
ctgctgcccg tgctgggctg gaactgcctg gcagagcgcg ccgcctgcag cgtggtgcgc     660
ccgctggcgc gcagccacgt ggctctgctc tccgccgcct tcttcatggt cttcggcatc     720
atgctgcacc tgtacgtgcg catctgccag gtggtctggc gccacgcgca ccagatcgcg     780
ctgcagcagc actgcctggc gccacccat ctcgctgcca ccagaaaggg tgtgggtaca     840
ctggctgtgg tgctgggcac tttcggcgcc agctggctgc ccttcgccat ctattgcgtg     900
gtgggcagcc atgaggaccc ggcggtctac acttacgcca ccctgctgcc cgccacctac     960
aactccatga tcaatcccat catctatgcc ttccgcaacc aggagatcca gcgcgccctg    1020
tggctcctgc tctgtggctg tgcggccgca cggggacgca ccccacccag cctgggtccc    1080
```

```
caagatgagt cctgcaccac cgccagctcc tccctggcca aggacacttc atcgtga          1137
```

<210> SEQ ID NO 50
<211> LENGTH: 350
<212> TYPE: PRT
<213> ORGANISM: Homo sapiens

<400> SEQUENCE: 50

```
Met Asn Glu Asp Leu Lys Val Asn Leu Ser Gly Leu Pro Arg Asp Tyr
 1               5                  10                  15

Leu Asp Ala Ala Ala Glu Asn Ile Ser Ala Val Ser Ser Arg
             20                  25                  30

Val Pro Ala Val Glu Pro Glu Pro Glu Leu Val Val Asn Pro Trp Asp
         35                  40                  45

Ile Val Leu Cys Thr Ser Gly Thr Leu Ile Ser Cys Glu Asn Ala Ile
     50                  55                  60

Val Val Leu Ile Ile Phe His Asn Pro Ser Leu Arg Ala Pro Met Phe
 65                  70                  75                  80

Leu Leu Ile Gly Ser Leu Ala Leu Ala Asp Leu Leu Ala Gly Ile Gly
                 85                  90                  95

Leu Ile Thr Asn Phe Val Phe Ala Tyr Leu Leu Gln Ser Glu Ala Thr
             100                 105                 110

Lys Leu Val Thr Ile Gly Leu Ile Val Ala Ser Phe Ser Ala Ser Val
         115                 120                 125

Cys Ser Leu Leu Ala Ile Thr Val Asp Arg Tyr Leu Ser Leu Tyr Tyr
     130                 135                 140

Ala Leu Thr Tyr His Ser Glu Arg Thr Val Thr Phe Thr Tyr Val Met
145                 150                 155                 160

Leu Val Met Leu Trp Gly Thr Ser Ile Cys Leu Gly Leu Leu Pro Val
                 165                 170                 175

Met Gly Trp Asn Cys Leu Arg Asp Glu Ser Thr Cys Ser Val Val Arg
             180                 185                 190

Pro Leu Thr Lys Asn Asn Ala Ala Ile Leu Ser Val Ser Phe Leu Phe
         195                 200                 205

Met Phe Ala Leu Met Leu Gln Leu Tyr Ile Gln Ile Cys Lys Ile Val
     210                 215                 220

Met Arg His Ala His Gln Ile Ala Leu Gln His His Phe Leu Ala Thr
225                 230                 235                 240

Ser His Tyr Val Thr Thr Arg Lys Gly Val Ser Thr Leu Ala Ile Ile
                 245                 250                 255

Leu Gly Thr Phe Ala Ala Cys Trp Met Pro Phe Thr Leu Tyr Ser Leu
             260                 265                 270

Ile Ala Asp Tyr Thr Tyr Pro Ser Ile Tyr Thr Tyr Ala Thr Leu Leu
         275                 280                 285

Pro Ala Thr Tyr Asn Ser Ile Ile Asn Pro Val Ile Tyr Ala Phe Arg
     290                 295                 300

Asn Gln Glu Ile Gln Lys Ala Leu Cys Leu Ile Cys Cys Gly Cys Ala
305                 310                 315                 320

Ala Ala Arg Gly Arg Thr Pro Pro Ser Leu Gly Pro Gln Asp Glu Ser
                 325                 330                 335

Cys Thr Thr Ala Ser Ser Ser Leu Ala Lys Asp Thr Ser Ser
             340                 345                 350
```

<210> SEQ ID NO 51

<211> LENGTH: 1053
<212> TYPE: DNA
<213> ORGANISM: Homo sapiens

<400> SEQUENCE: 51

| | | | | | |
|---|---|---|---|---|---|
| atgaatgaag | acctgaaggt | caatttaagc | gggctgcctc | gggattattt | agatgccgct | 60 |
| gctgcggaga | acatctcggc | tgctgtctcc | tcccggggttc | ctgccgtaga | gccagagcct | 120 |
| gagctcgtag | tcaacccctg | ggacattgtc | ttgtgtacct | cgggaaccct | catctcctgt | 180 |
| gaaaatgcca | ttgtggtcct | tatcatcttc | cacaacccca | gcctgcgagc | acccatgttc | 240 |
| ctgctaatag | gcagcctggc | tcttgcagac | ctgctggccg | gcattggact | catcaccaat | 300 |
| tttgttttg | cctacctgct | tcagtcagaa | gccaccaagc | tggtcacgat | cggcctcatt | 360 |
| gtcgcctctt | tctctgcctc | tgtctgcagc | ttgctggcta | tcactgttga | ccgctacctc | 420 |
| tcactgtact | acgctctgac | gtaccattcg | gagaggacgg | tcacgtttac | ctatgtcatg | 480 |
| ctcgtcatgc | tctgggggac | ctccatctgc | tggggctgc | tgcccgtcat | gggctggaac | 540 |
| tgcctccgag | acgagtccac | ctgcagcgtg | gtcagaccgc | tcaccaagaa | caacgcggcc | 600 |
| atcctctcgg | tgtccttcct | cttcatgttt | gcgctcatgc | ttcagctcta | catccagatc | 660 |
| tgtaagattg | tgatgaggca | cgcccatcag | atagccctgc | agcaccactt | cctggccacg | 720 |
| tcgcactatg | tgaccacccg | gaaaggggtc | tccaccctgg | ctatcatcct | ggggacgttt | 780 |
| gctgcttgct | ggatgccttt | caccctctat | tccttgatag | cggattacac | ctaccccctcc | 840 |
| atctataccct | acgccaccct | cctgcccgcc | acctacaatt | ccatcatcaa | ccctgtcata | 900 |
| tatgctttca | gaaaccaaga | gatccagaaa | gcgctctgtc | tcatttgctg | cggctgcgcg | 960 |
| gccgcacggg | gacgcacccc | acccagcctg | gtccccaag | atgagtcctg | caccaccgcc | 1020 |
| agctcctccc | tggccaagga | cacttcatcg | tga | | | 1053 |

<210> SEQ ID NO 52
<211> LENGTH: 388
<212> TYPE: PRT
<213> ORGANISM: Homo sapiens

<400> SEQUENCE: 52

Met Ala Asn Thr Thr Gly Glu Pro Glu Glu Val Ser Gly Ala Leu Ser
1               5                   10                  15

Pro Pro Ser Ala Ser Ala Tyr Val Lys Leu Val Leu Leu Gly Leu Ile
            20                  25                  30

Met Cys Val Ser Leu Ala Gly Asn Ala Ile Leu Ser Leu Leu Val Leu
        35                  40                  45

Lys Glu Arg Ala Leu His Lys Ala Pro Tyr Tyr Phe Leu Leu Asp Leu
    50                  55                  60

Cys Leu Ala Asp Gly Ile Arg Ser Ala Val Cys Phe Pro Phe Val Leu
65                  70                  75                  80

Ala Ser Val Arg His Gly Ser Ser Trp Thr Phe Ser Ala Leu Ser Cys
                85                  90                  95

Lys Ile Val Ala Phe Met Ala Val Leu Phe Cys Phe His Ala Ala Phe
            100                 105                 110

Met Leu Phe Cys Ile Ser Val Thr Arg Tyr Met Ala Ile Ala His His
        115                 120                 125

Arg Phe Tyr Ala Lys Arg Met Thr Leu Trp Thr Cys Ala Ala Val Ile
    130                 135                 140

Cys Met Ala Trp Thr Leu Ser Val Ala Met Ala Phe Pro Pro Val Phe
145                 150                 155                 160

Asp Val Gly Thr Tyr Lys Phe Ile Arg Glu Glu Asp Gln Cys Ile Phe
                165                 170                 175

Glu His Arg Tyr Phe Lys Ala Asn Asp Thr Leu Gly Phe Met Leu Met
            180                 185                 190

Leu Ala Val Leu Met Ala Ala Thr His Ala Val Tyr Gly Lys Leu Leu
        195                 200                 205

Leu Phe Glu Tyr Arg His Arg Lys Met Lys Pro Val Gln Met Val Pro
    210                 215                 220

Ala Ile Ser Gln Asn Trp Thr Phe His Gly Pro Gly Ala Thr Gly Gln
225                 230                 235                 240

Ala Ala Ala Asn Trp Ile Ala Gly Phe Gly Arg Gly Pro Met Pro Pro
                245                 250                 255

Thr Leu Leu Gly Ile Arg Gln Asn Gly His Ala Ala Ser Arg Arg Leu
            260                 265                 270

Leu Gly Met Asp Glu Val Lys Gly Glu Lys Gln Leu Gly Arg Met Phe
        275                 280                 285

Tyr Ala Ile Thr Leu Leu Phe Leu Leu Leu Trp Ser Pro Tyr Ile Val
    290                 295                 300

Ala Cys Tyr Trp Arg Val Phe Val Lys Ala Cys Ala Val Pro His Arg
305                 310                 315                 320

Tyr Leu Ala Thr Ala Val Trp Met Ser Phe Ala Gln Ala Ala Val Asn
                325                 330                 335

Pro Ile Val Cys Phe Leu Leu Asn Lys Asp Leu Lys Lys Cys Leu Arg
            340                 345                 350

Thr His Ala Pro Cys Ala Ala Ala Arg Gly Arg Thr Pro Pro Ser Leu
        355                 360                 365

Gly Pro Gln Asp Glu Ser Cys Thr Thr Ala Ser Ser Leu Ala Lys
    370                 375                 380

Asp Thr Ser Ser
385

<210> SEQ ID NO 53
<211> LENGTH: 1167
<212> TYPE: DNA
<213> ORGANISM: Homo sapiens

<400> SEQUENCE: 53
atggccaaca ctaccggaga gcctgaggag gtgagcggcg ctctgtcccc accgtccgca      60
tcagcttatg tgaagctggt actgctggga ctgattatgt gcgtgagcct ggcgggtaac     120
gccatcttgt ccctgctggt gctcaaggag cgtgccctgc acaaggctcc ttactacttc     180
ctgctggacc tgtgcctggc cgatggcata cgctctgccg tctgcttccc ctttgtgctg     240
gcttctgtgc gccacggctc ttcatggacc ttcagtgcac tcagctgcaa gattgtggcc     300
tttatggccg tgctcttttg cttccatgcg gccttcatgc tgttctgcat cagcgtcacc     360
cgctacatgg ccatcgccca ccaccgcttc tacgccaagc gcatgacact ctggacatgc     420
gcggctgtca tctgcatggc ctggaccctg tctgtggcca tggccttccc acctgtcttt     480
gacgtgggca cctacaagtt tattcgggag gaggaccagt gcatctttga gcatcgctac     540
ttcaaggcca tgacacgct gggcttcatg cttatgttgg ctgtgctcat ggcagctacc     600
catgctgtct acggcaagct gctcctcttc gagtatcgtc accgcaagat gaagccagtg     660
cagatggtgc cagccatcag ccagaactgg acattccatg gtcccggggc caccggccag     720
gctgctgcca actggatcgc cggctttggc cgtgggccca tgccaccaac cctgctgggt     780

-continued

| | | | | |
|---|---|---|---|---|
| atccggcaga | atgggcatgc | agccagccgg | cggctactgg | gcatggacga ggtcaagggt | 840 |
| gaaaagcagc | tgggccgcat | gttctacgcg | atcacactgc | tctttctgct cctctggtca | 900 |
| ccctacatcg | tggcctgcta | ctggcgagtg | tttgtgaaag | cctgtgctgt gccccaccgc | 960 |
| tacctggcca | ctgctgtttg | atgagcttc | gcccaggctg | ccgtcaaccc aattgtctgc | 1020 |
| ttcctgctca | acaaggacct | caagaagtgc | ctgaggactc | acgcccctg cgcggccgca | 1080 |
| cggggacgca | ccccacccag | cctgggtccc | caagatgagt | cctgcaccac cgccagctcc | 1140 |
| tccctggcca | aggacacttc | atcgtga | | | 1167 |

<210> SEQ ID NO 54
<211> LENGTH: 388
<212> TYPE: PRT
<213> ORGANISM: Homo sapiens

<400> SEQUENCE: 54

```
Met Ala Asn Tyr Ser His Ala Ala Asp Asn Ile Leu Gln Asn Leu Ser
  1               5                  10                  15

Pro Leu Thr Ala Phe Leu Lys Leu Thr Ser Leu Gly Phe Ile Ile Gly
             20                  25                  30

Val Ser Val Val Gly Asn Leu Leu Ile Ser Ile Leu Leu Val Lys Asp
         35                  40                  45

Lys Thr Leu His Arg Ala Pro Tyr Tyr Phe Leu Leu Asp Leu Cys Cys
     50                  55                  60

Ser Asp Ile Leu Arg Ser Ala Ile Cys Phe Pro Phe Val Phe Asn Ser
 65                  70                  75                  80

Val Lys Asn Gly Ser Thr Trp Thr Tyr Gly Thr Leu Thr Cys Lys Val
                 85                  90                  95

Ile Ala Phe Leu Gly Val Leu Ser Cys Phe His Thr Ala Phe Met Leu
            100                 105                 110

Phe Cys Ile Ser Val Thr Arg Tyr Leu Ala Ile Ala His His Arg Phe
        115                 120                 125

Tyr Thr Lys Arg Leu Thr Phe Trp Thr Cys Leu Ala Val Ile Cys Met
    130                 135                 140

Val Trp Thr Leu Ser Val Ala Met Ala Phe Pro Pro Val Leu Asp Val
145                 150                 155                 160

Gly Thr Tyr Ser Phe Ile Arg Glu Glu Asp Gln Cys Thr Phe Gln His
                165                 170                 175

Arg Ser Phe Arg Ala Asn Asp Ser Leu Gly Phe Met Leu Leu Leu Ala
            180                 185                 190

Leu Ile Leu Leu Ala Thr Gln Leu Val Tyr Leu Lys Leu Ile Phe Phe
        195                 200                 205

Val His Asp Arg Arg Lys Met Lys Pro Val Gln Phe Val Ala Ala Val
    210                 215                 220

Ser Gln Asn Trp Thr Phe His Gly Pro Gly Ala Ser Gly Gln Ala Ala
225                 230                 235                 240

Ala Asn Trp Leu Ala Gly Phe Gly Arg Gly Pro Thr Pro Pro Thr Leu
                245                 250                 255

Leu Gly Ile Arg Gln Asn Ala Asn Thr Thr Gly Arg Arg Leu Leu
            260                 265                 270

Val Leu Asp Glu Phe Lys Met Glu Lys Arg Ile Ser Arg Met Phe Tyr
        275                 280                 285

Ile Met Thr Phe Leu Phe Leu Thr Leu Trp Gly Pro Tyr Leu Val Ala
    290                 295                 300
```

Cys Tyr Trp Arg Val Phe Ala Arg Gly Pro Val Pro Gly Gly Phe
305                 310                 315                 320

Leu Thr Ala Ala Val Trp Met Ser Phe Ala Gln Ala Gly Ile Asn Pro
            325                 330                 335

Phe Val Cys Ile Phe Ser Asn Arg Glu Leu Arg Arg Cys Phe Ser Thr
        340                 345                 350

Thr Leu Leu Tyr Cys Ala Ala Arg Gly Arg Thr Pro Pro Ser Leu
        355                 360                 365

Gly Pro Gln Asp Glu Ser Cys Thr Thr Ala Ser Ser Ser Leu Ala Lys
    370                 375                 380

Asp Thr Ser Ser
385

<210> SEQ ID NO 55
<211> LENGTH: 1167
<212> TYPE: DNA
<213> ORGANISM: Homo sapiens

<400> SEQUENCE: 55

| | | | | | |
|---|---|---|---|---|---|
| atggcgaact | atagccatgc | agctgacaac | attttgcaaa | atctctcgcc | tctaacagcc | 60 |
| tttctgaaac | tgacttcctt | gggtttcata | ataggagtca | gcgtggtggg | caacctcctg | 120 |
| atctccattt | tgctagtgaa | agataagacc | ttgcatagag | cacttacta | cttcctgttg | 180 |
| gatctttgct | gttcagatat | cctcagatct | gcaatttgtt | tcccatttgt | gttcaactct | 240 |
| gtcaaaaatg | gctctacctg | gacttatggg | actctgactt | gcaaagtgat | tgcctttctg | 300 |
| ggggttttgt | cctgttttcca | cactgctttc | atgctcttct | gcatcagtgt | caccagatac | 360 |
| ttagctatcg | cccatcaccg | cttctataca | aagaggctga | cctttggac | gtgtctggct | 420 |
| gtgatctgta | tggtgtggac | tctgtctgtg | gccatggcat | ttccccggt | tttagacgtg | 480 |
| ggcacttact | cattcattag | ggaggaagat | caatgcacct | tccaacaccg | ctccttcagg | 540 |
| gctaatgatt | ccttaggatt | tatgctgctt | cttgctctca | tcctcctagc | cacacagctt | 600 |
| gtctacctca | agctgatatt | tttcgtccac | gatcgaagaa | aaatgaagcc | agtccagttt | 660 |
| gtagcagcag | tcagccagaa | ctggactttt | catggtcctg | gagccagtgg | ccaggcagct | 720 |
| gccaattggc | tagcaggatt | tggaaggggt | cccacaccac | ccaccttgct | gggcatcagg | 780 |
| caaaatgcaa | acaccacagg | cagaagaagg | ctattggtct | tagacgagtt | caaaatggag | 840 |
| aaaagaatca | gcagaatgtt | ctatataatg | acttttctgt | ttctaacctt | gtggggcccc | 900 |
| tacctggtgg | cctgttattg | gagagttttt | gcaagagggc | ctgtagtacc | aggggatttt | 960 |
| ctaacagctg | ctgtctggat | gagttttgcc | caagcaggaa | tcaatccttt | tgtctgcatt | 1020 |
| ttctcaaaca | gggagctgag | gcgctgtttc | agcacaaccc | ttctttactg | cgcggccgca | 1080 |
| cggggacgca | ccccacccag | cctgggtccc | caagatgagt | cctgcaccac | cgccagctcc | 1140 |
| tccctggcca | aggacacttc | atcgtga | | | | 1167 |

<210> SEQ ID NO 56
<211> LENGTH: 364
<212> TYPE: PRT
<213> ORGANISM: Homo sapiens

<400> SEQUENCE: 56

Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly

```
                 20                  25                  30
His Asn Ala Thr Phe Ser Glu Pro Leu Pro Phe Leu Tyr Val Leu Leu
             35                  40                  45

Pro Ala Val Tyr Ser Gly Ile Cys Ala Val Gly Leu Thr Gly Asn Thr
         50                  55                  60

Ala Val Ile Leu Val Ile Leu Arg Ala Pro Lys Met Lys Thr Val Thr
 65                  70                  75                  80

Asn Val Phe Ile Leu Asn Leu Ala Val Ala Asp Gly Leu Phe Thr Leu
                 85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
            115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Arg Val Trp
        195                 200                 205

Phe Lys Ala Ser Arg Val Tyr Thr Leu Val Leu Gly Phe Val Leu Pro
210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Leu Ala Val Cys Leu Leu Cys
            260                 265                 270

Trp Thr Pro Phe His Leu Ala Ser Val Val Ala Leu Thr Thr Asp Leu
        275                 280                 285

Pro Gln Thr Pro Leu Val Ile Ser Met Ser Tyr Val Ile Thr Ser Leu
    290                 295                 300

Ser Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys Ala Ala Ala
                325                 330                 335

Arg Gly Arg Thr Pro Pro Ser Leu Gly Pro Gln Asp Glu Ser Cys Thr
            340                 345                 350

Thr Ala Ser Ser Ser Leu Ala Lys Asp Thr Ser Ser
        355                 360

<210> SEQ ID NO 57
<211> LENGTH: 1095
<212> TYPE: DNA
<213> ORGANISM: Homo sapiens

<400> SEQUENCE: 57
atgcaggccg ctgggcaccc agagccccett gacagcaggg gctccttctc cctccccacg      60
atgggtgcca acgtctctca ggacaatggc actggccaca atgccacctt ctccgagcca     120
ctgccgttcc tctatgtgct cctgcccgcc gtgtactccg ggatctgtgc tgtggggctg     180
```

```
actggcaaca cggccgtcat ccttgtaatc ctaagggcgc ccaagatgaa gacggtgacc      240
aacgtgttca tcctgaacct ggccgtcgcc gacgggctct tcacgctggt actgcccgtc      300
aacatcgcgg agcacctgct gcagtactgg cccttcgggg agctgctctg caagctggtg      360
ctggccgtcg accactacaa catcttctcc agcatctact tcctagccgt gatgagcgtg      420
gaccgatacc tggtggtgct ggccaccgtg aggtcccgcc acatgccctg cgcacctac       480 cgggggcga aggtcgccag cctgtgtgtc tggctgggcg tcacggtcct ggttctgccc      540
ttcttctctt cgctggcgt ctacagcaac gagctgcagg tcccaagctg tgggctgagc      600
ttcccgtggc ccgagcgggt ctggttcaag gccagccgtg tctacacttt ggtcctgggc      660
ttcgtgctgc ccgtgtgcac catctgtgtg ctctacacag acctcctgcg caggctgcgg      720
gccgtgcggc tccgctctgg agccaaggct ctaggcaagg ccaggcggaa ggtgaccgtc      780
ctggtcctcg tcgtgctggc cgtgtgcctc ctctgctgga cgcccttcca cctggcctct      840
gtcgtggccc tgaccacgga cctgcccag accccactgg tcatcagtat gtcctacgtc      900
atcaccagcc tcagctacgc caactcgtgc ctgaaccct tcctctacgc ctttctagat      960
gacaacttcc ggaagaactt ccgcagcata ttgcggtgcg cggccgcacg gggacgcacc     1020
ccacccagcc tgggtcccca agatgagtcc tgcaccaccg ccagctcctc cctggccaag     1080
gacacttcat cgtga                                                       1095

<210> SEQ ID NO 58
<211> LENGTH: 419
<212> TYPE: PRT
<213> ORGANISM: Homo sapiens

<400> SEQUENCE: 58

Met Cys Phe Ser Pro Ile Leu Glu Ile Asn Met Gln Ser Glu Ser Asn
  1               5                  10                  15

Ile Thr Val Arg Asp Asp Ile Asp Ile Asn Thr Asn Met Tyr Gln
                 20                  25                  30

Pro Leu Ser Tyr Pro Leu Ser Phe Gln Val Ser Leu Thr Gly Phe Leu
             35                  40                  45

Met Leu Glu Ile Val Leu Gly Leu Gly Ser Asn Leu Thr Val Leu Val
         50                  55                  60

Leu Tyr Cys Met Lys Ser Asn Leu Ile Asn Ser Val Ser Asn Ile Ile
 65                  70                  75                  80

Thr Met Asn Leu His Val Leu Asp Val Ile Ile Cys Val Gly Cys Ile
                 85                  90                  95

Pro Leu Thr Ile Val Ile Leu Leu Ser Leu Glu Ser Asn Thr Ala
            100                 105                 110

Leu Ile Cys Cys Phe His Glu Ala Cys Val Ser Phe Ala Ser Val Ser
            115                 120                 125

Thr Ala Ile Asn Val Phe Ala Ile Thr Leu Asp Arg Tyr Asp Ile Ser
        130                 135                 140

Val Lys Pro Ala Asn Arg Ile Leu Thr Met Gly Arg Ala Val Met Leu
145                 150                 155                 160

Met Ile Ser Ile Trp Ile Phe Ser Phe Phe Ser Phe Leu Ile Pro Phe
                165                 170                 175

Ile Glu Val Asn Phe Phe Ser Leu Gln Ser Gly Asn Thr Trp Glu Asn
            180                 185                 190

Lys Thr Leu Leu Cys Val Ser Thr Asn Glu Tyr Tyr Thr Glu Leu Gly
        195                 200                 205
```

```
Met Tyr Tyr His Leu Leu Val Gln Ile Pro Ile Phe Phe Thr Val
210                 215                 220
Val Val Met Leu Ile Thr Tyr Thr Lys Ile Leu Gln Ala Leu Asn Ile
225                 230                 235                 240
Arg Ile Gly Thr Arg Phe Ser Thr Gly Gln Lys Lys Ala Arg Lys
                245                 250                 255
Lys Lys Thr Ile Ser Leu Thr Thr Gln His Glu Ala Thr Asp Met Ser
                260                 265                 270
Gln Ser Ser Gly Gly Arg Asn Val Val Phe Gly Val Arg Thr Ser Val
                275                 280                 285
Ser Val Ile Ile Ala Leu Arg Arg Ala Val Lys Arg His Arg Glu Arg
290                 295                 300
Arg Glu Arg Gln Lys Arg Val Phe Arg Met Ser Leu Leu Ile Ile Ser
305                 310                 315                 320
Thr Phe Leu Leu Cys Trp Thr Pro Ile Ser Val Leu Asn Thr Thr Ile
                325                 330                 335
Leu Cys Leu Gly Pro Ser Asp Leu Leu Val Lys Leu Arg Leu Cys Phe
                340                 345                 350
Leu Val Met Ala Tyr Gly Thr Thr Ile Phe His Pro Leu Leu Tyr Ala
                355                 360                 365
Phe Thr Arg Gln Lys Phe Gln Lys Val Leu Lys Ser Lys Met Lys Lys
370                 375                 380
Arg Val Val Cys Ala Ala Ala Arg Gly Arg Thr Pro Pro Ser Leu Gly
385                 390                 395                 400
Pro Gln Asp Glu Ser Cys Thr Thr Ala Ser Ser Leu Ala Lys Asp
                405                 410                 415
Thr Ser Ser

<210> SEQ ID NO 59
<211> LENGTH: 1260
<212> TYPE: DNA
<213> ORGANISM: Homo sapiens

<400> SEQUENCE: 59
atgtgttttt ctcccattct ggaaatcaac atgcagtctg aatctaacat tacagtgcga      60
gatgacattg atgacatcaa caccaatatg taccaaccac tatcatatcc gttaagcttt     120
caagtgtctc tcaccggatt tcttatgtta gaaattgtgt tgggacttgg cagcaacctc     180
actgtattgg tactttactg catgaaatcc aacttaatca actctgtcag taacattatt     240
acaatgaatc ttcatgtact tgatgtaata atttgtgtgg gatgtattcc tctaactata     300
gttatccttc tgctttcact ggagagtaac actgctctca tttgctgttt ccatgaggct     360
tgtgtatctt ttgcaagtgt ctcaacagca atcaacgttt tgctatcac tttggacaga     420
tatgacatct ctgtaaaacc tgcaaaccga attctgacaa tgggcagagc tgtaatgtta     480
atgatatcca tttggatttt ttcttttttc tctttcctga ttcctttat tgaggtaaat     540
tttttcagtc ttcaaagtgg aaatacctgg gaaaacaaga cacttttatg tgtcagtaca     600
aatgaatact acactgaact gggaatgtat tatcacctgt tagtacagat cccaatattc     660
ttttcactg ttgtagtaat gttaatcaca tacaccaaaa tacttcaggc tcttaatatt     720
cgaataggca caagattttc aacagggcag aagaagaaag caagaaagaa aaagacaatt     780
tctctaacca cacaacatga ggctacagac atgtcacaaa gcagtggtgg gagaaatgta     840
gtctttggtg taagaacttc agtttctgta ataattgccc tccggcgagc tgtgaaacga     900
```

-continued

```
caccgtgaac gacgagaaag acaaaagaga gtcttcagga tgtctttatt gattatttct    960
acatttcttc tctgctggac accaatttct gttttaaata ccaccatttt atgtttaggc   1020
ccaagtgacc ttttagtaaa attaagattg tgttttttag tcatggctta tggaacaact   1080
atatttcacc ctctattata tgcattcact agacaaaaat ttcaaaaggt cttgaaaagt   1140
aaaatgaaaa agcgagttgt ttgtgcggcc gcacggggac gcaccccacc cagcctggt    1200 ccccaagatg agtcctgcac caccgccagc tcctccctgg ccaaggacac ttcatcgtga   1260
```

<210> SEQ ID NO 60
<211> LENGTH: 370
<212> TYPE: PRT
<213> ORGANISM: Homo sapiens

<400> SEQUENCE: 60

```
Met Gly Gln Pro Gly Asn Gly Ser Ala Phe Leu Leu Ala Pro Asn Arg
 1               5                   10                  15

Ser His Ala Pro Asp His Asp Val Thr Gln Gln Arg Asp Glu Val Trp
             20                  25                  30

Val Val Gly Met Gly Ile Val Met Ser Leu Ile Val Leu Ala Ile Val
         35                  40                  45

Phe Gly Asn Val Leu Val Ile Thr Ala Ile Ala Lys Phe Glu Arg Leu
     50                  55                  60

Gln Thr Val Thr Asn Tyr Phe Ile Thr Ser Leu Ala Cys Ala Asp Leu
 65                  70                  75                  80

Val Met Gly Leu Ala Val Val Pro Phe Gly Ala Ala His Ile Leu Met
                 85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320
```

```
Phe Asn Pro Leu Ile Tyr Cys Arg Ser Pro Asp Phe Arg Ile Ala Phe
            325                 330                 335

Gln Glu Leu Leu Cys Ala Arg Gly Arg Thr Pro Ser Leu Gly Pro
        340                 345                 350

Gln Asp Glu Ser Cys Thr Thr Ala Ser Ser Ser Leu Ala Lys Asp Thr
            355                 360                 365

Ser Ser
    370

<210> SEQ ID NO 61
<211> LENGTH: 382
<212> TYPE: PRT
<213> ORGANISM: Homo sapiens

<400> SEQUENCE: 61

Met Asp Ser Ser Thr Gly Pro Gly Asn Thr Ser Asp Cys Ser Asp Pro
 1               5                  10                  15

Leu Ala Gln Ala Ser Cys Ser Pro Ala Pro Gly Ser Trp Leu Asn Leu
            20                  25                  30

Ser His Val Asp Gly Asn Gln Ser Asp Pro Cys Gly Leu Asn Arg Thr
        35                  40                  45

Gly Leu Gly Gly Asn Asp Ser Leu Cys Pro Gln Thr Gly Ser Pro Ser
50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr
        115                 120                 125

Leu Met Gly Thr Trp Pro Phe Gly Thr Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
```

-continued

```
305                 310                 315                 320
Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ala
            340                 345                 350

Ala Ala Arg Gly Arg Thr Pro Pro Ser Leu Gly Pro Gln Asp Glu Ser
            355                 360                 365

Cys Thr Thr Ala Ser Ser Leu Ala Lys Asp Thr Ser Ser
            370                 375                 380

<210> SEQ ID NO 62
<211> LENGTH: 382
<212> TYPE: PRT
<213> ORGANISM: Homo sapiens

<400> SEQUENCE: 62

Met Ala Pro Asn Thr Ser Thr Met Asp Glu Ala Gly Leu Pro Ala Glu
  1               5                  10                  15

Arg Asp Phe Ser Phe Arg Ile Leu Thr Ala Cys Phe Leu Ser Leu Leu
             20                  25                  30

Ile Leu Ser Thr Leu Leu Gly Asn Thr Leu Val Cys Ala Ala Val Ile
         35                  40                  45

Arg Phe Arg His Leu Arg Ser Lys Val Thr Asn Phe Phe Val Ile Ser
     50                  55                  60

Leu Ala Val Ser Asp Leu Leu Val Ala Val Leu Val Met Pro Trp Lys
 65                  70                  75                  80

Ala Val Ala Glu Ile Ala Gly Phe Trp Pro Phe Gly Ser Phe Cys Asn
                 85                  90                  95

Ile Trp Val Ala Phe Asp Ile Met Cys Ser Thr Ala Ser Ile Leu Asn
            100                 105                 110

Leu Cys Val Ile Ser Val Asp Arg Tyr Trp Ala Ile Ser Ser Pro Phe
        115                 120                 125

Gln Tyr Glu Arg Lys Met Thr Pro Lys Ala Ala Phe Ile Leu Ile Ser
    130                 135                 140

Val Ala Trp Thr Leu Ser Val Leu Ile Ser Phe Ile Pro Val Gln Leu
145                 150                 155                 160

Ser Trp His Lys Ala Lys Pro Thr Trp Pro Leu Asp Gly Asn Phe Thr
                165                 170                 175

Ser Leu Glu Asp Thr Glu Asp Asp Asn Cys Asp Thr Arg Leu Ser Arg
            180                 185                 190

Thr Tyr Ala Ile Ser Ser Ser Leu Ile Ser Phe Tyr Ile Pro Val Ala
        195                 200                 205

Ile Met Ile Val Thr Tyr Thr Ser Ile Tyr Arg Ile Ala Gln Lys Gln
    210                 215                 220

Ile Arg Arg Ile Ser Ala Leu Glu Arg Ala Ala Val His Ala Lys Asn
225                 230                 235                 240

Cys Gln Thr Thr Ala Gly Asn Gly Asn Pro Val Glu Cys Ala Gln Ser
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Ser Asn Cys Met Val Pro Phe Cys Gly Ser Glu Glu Thr Gln
    290                 295                 300
```

```
Pro Phe Cys Ile Asp Ser Ile Thr Phe Asp Val Phe Val Trp Phe Gly
305                 310                 315                 320

Trp Ala Asn Ser Ser Leu Asn Pro Ile Ile Tyr Ala Phe Asn Ala Asp
            325                 330                 335

Phe Gln Lys Ala Phe Ser Thr Leu Leu Gly Cys Tyr Arg Leu Cys Ala
        340                 345                 350

Ala Ala Arg Gly Arg Thr Pro Pro Ser Leu Gly Pro Gln Asp Glu Ser
    355                 360                 365

Cys Thr Thr Ala Ser Ser Leu Ala Lys Asp Thr Ser Ser
370                 375                 380
```

<210> SEQ ID NO 63
<211> LENGTH: 451
<212> TYPE: PRT
<213> ORGANISM: Homo sapiens

<400> SEQUENCE: 63

```
Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
            20                  25                  30

Val Ser Tyr Gln Val Ile Thr Ser Leu Leu Leu Gly Thr Leu Ile Phe
        35                  40                  45

Cys Ala Val Leu Gly Asn Ala Cys Val Val Ala Ala Ile Ala Leu Glu
    50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
    130                 135                 140

Val Asn Lys Arg Thr Pro Arg Arg Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
    210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300
```

-continued

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
            325                 330                 335

Leu Ala Arg Glu Arg Lys Thr Val Lys Thr Leu Gly Ile Ile Met Gly
            340                 345                 350

Thr Phe Ile Leu Cys Trp Leu Pro Phe Phe Ile Val Ala Leu Val Leu
            355                 360                 365

Pro Phe Cys Glu Ser Ser Cys His Met Pro Thr Leu Leu Gly Ala Ile
            370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
            405                 410                 415

Cys Asn Phe Cys Ala Ala Ala Arg Gly Arg Thr Pro Pro Ser Leu Gly
            420                 425                 430

Pro Gln Asp Glu Ser Cys Thr Thr Ala Ser Ser Ser Leu Ala Lys Asp
            435                 440                 445

Thr Ser Ser
    450

<210> SEQ ID NO 64
<211> LENGTH: 394
<212> TYPE: PRT
<213> ORGANISM: Homo sapiens

<400> SEQUENCE: 64

Met Ala Pro Trp Pro His Glu Asn Ser Ser Leu Ala Pro Trp Pro Asp
1               5                   10                  15

Leu Pro Thr Leu Ala Pro Asn Thr Ala Asn Thr Ser Gly Leu Pro Gly
            20                  25                  30

Val Pro Trp Glu Ala Ala Leu Ala Gly Ala Leu Leu Ala Leu Ala Val
            35                  40                  45

Leu Ala Thr Val Gly Gly Asn Leu Leu Val Ile Val Ala Ile Ala Trp
        50                  55                  60

Thr Pro Arg Leu Gln Thr Met Thr Asn Val Phe Val Thr Ser Leu Ala
65                  70                  75                  80

Ala Ala Asp Leu Val Met Gly Leu Leu Val Val Pro Pro Ala Ala Thr
                85                  90                  95

Leu Ala Leu Thr Gly His Trp Pro Leu Gly Ala Thr Gly Cys Glu Leu
            100                 105                 110

Trp Thr Ser Val Asp Val Leu Cys Val Thr Ala Ser Ile Glu Thr Leu
            115                 120                 125

Cys Ala Leu Ala Val Asp Arg Tyr Leu Ala Val Thr Asn Pro Leu Arg
        130                 135                 140

Tyr Gly Ala Leu Val Thr Lys Arg Cys Ala Arg Thr Ala Val Val Leu
145                 150                 155                 160

Val Trp Val Val Ser Ala Ala Val Ser Phe Ala Pro Ile Met Ser Gln
                165                 170                 175

Trp Trp Arg Val Gly Ala Asp Ala Glu Ala Gln Arg Cys His Ser Asn
            180                 185                 190

Pro Arg Cys Cys Ala Phe Ala Ser Asn Met Pro Tyr Val Leu Leu Ser
            195                 200                 205

Ser Ser Val Ser Phe Tyr Leu Pro Leu Leu Val Met Leu Phe Val Tyr

-continued

```
            210                 215                 220
Ala Arg Val Phe Val Ala Thr Arg Gln Leu Arg Leu Leu Arg Gly
225                 230                 235                 240

Glu Leu Gly Arg Phe Pro Pro Glu Ser Pro Pro Ala Pro Ser Arg
                245                 250                 255

Ser Leu Ala Pro Ala Pro Val Gly Thr Cys Ala Pro Glu Gly Val
                260                 265                 270

Pro Ala Cys Gly Arg Arg Pro Ala Arg Leu Leu Pro Leu Arg Glu His
                275                 280                 285

Arg Ala Leu Cys Thr Leu Gly Leu Ile Met Gly Thr Phe Thr Leu Cys
290                 295                 300

Trp Leu Pro Phe Phe Leu Ala Asn Val Leu Arg Ala Leu Gly Gly Pro
305                 310                 315                 320

Ser Leu Val Pro Gly Pro Ala Phe Leu Ala Leu Asn Trp Leu Gly Tyr
                325                 330                 335

Ala Asn Ser Ala Phe Asn Pro Leu Ile Tyr Cys Arg Ser Pro Asp Phe
                340                 345                 350

Arg Ser Ala Phe Arg Arg Leu Leu Cys Arg Cys Ala Ala Ala Arg Gly
                355                 360                 365

Arg Thr Pro Pro Ser Leu Gly Pro Gln Asp Glu Ser Cys Thr Thr Ala
                370                 375                 380

Ser Ser Ser Leu Ala Lys Asp Thr Ser Ser
385                 390
```

<210> SEQ ID NO 65
<211> LENGTH: 362
<212> TYPE: PRT
<213> ORGANISM: Homo sapiens

<400> SEQUENCE: 65

```
Met Gly Pro Thr Ser Val Pro Leu Val Lys Ala His Arg Ser Ser Val
1                   5                   10                  15

Ser Asp Tyr Val Asn Tyr Asp Ile Ile Val Arg His Tyr Asn Tyr Thr
                20                  25                  30

Gly Lys Leu Asn Ile Ser Ala Asp Lys Glu Asn Ser Ile Lys Leu Thr
            35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
                100                 105                 110

Thr Pro Ala Gln Trp Phe Leu Arg Glu Gly Ser Met Phe Val Ala Leu
            115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
                180                 185                 190
```

```
-continued

Thr Val Leu Pro Leu Tyr His Lys His Tyr Ile Leu Phe Cys Thr Thr
        195             200                 205

Val Phe Thr Leu Leu Leu Leu Ser Ile Val Ile Leu Tyr Cys Arg Ile
        210             215                 220

Tyr Ser Leu Val Arg Thr Arg Ser Arg Arg Leu Thr Phe Arg Lys Asn
225             230             235                     240

Ile Ser Lys Ala Ser Arg Ser Ser Glu Lys Ser Leu Ala Leu Leu Lys
                245             250                 255

Thr Val Ile Ile Val Leu Ser Val Phe Ile Ala Cys Trp Ala Pro Leu
            260             265                 270

Phe Ile Leu Leu Leu Leu Asp Val Gly Cys Lys Val Lys Thr Cys Asp
        275             280                 285

Ile Leu Phe Arg Ala Glu Tyr Phe Leu Val Leu Ala Val Leu Asn Ser
        290             295                 300

Gly Thr Asn Pro Ile Ile Tyr Thr Leu Thr Asn Lys Glu Met Arg Arg
305             310             315                     320

Ala Phe Ile Arg Ile Met Ser Cys Cys Lys Cys Ala Ala Ala Arg Gly
                325             330                 335

Arg Thr Pro Pro Ser Leu Gly Pro Gln Asp Glu Ser Cys Thr Thr Ala
            340             345                 350

Ser Ser Ser Leu Ala Lys Asp Thr Ser Ser
        355             360
```

METHODS OF SCREENING COMPOSITIONS FOR G PROTEIN-COUPLED RECEPTOR DESENSITIZATION INHIBITORY ACTIVITY

RELATED APPLICATIONS

This application is a continuation-in-part of U.S. application Ser. No. 09/993,844, filed Nov. 5, 2001 now U.S. Pat. No. 7,018,812, which claims the benefit of U.S. Provisional Application No. 60/245,772, filed Nov. 3, 2000, and which claims the benefit of U.S. Provisional Application No. 60/260,363, filed Jan. 8, 2001.

FIELD OF THE INVENTION

The present invention generally relates to methods for screening test compositions for G protein-coupled receptor desensitization inhibitory activity, and more particularly relates to screening test compositions for G protein coupled receptor desensitization inhibitory activity that is not specific to a particular receptor.

BACKGROUND OF THE INVENTION

G protein-coupled receptors (GPCRs) are cell surface proteins that translate hormone or ligand binding into intracellular signals. GPCRs are found in all animals, insects, and plants. GPCR signaling plays a pivotal role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length.

The magnitude of the physiological responses controlled by GPCRs is linked to the balance between GPCR signaling and signal termination. The signaling of GPCRs is controlled by a family of intracellular proteins called arresting. Arrestins bind activated GPCRs, including those that have been agonist-activated and especially those that have been phosphorylated by G protein-coupled receptor kinases (GRKs).

GPCRs have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer.

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See, e.g., Jurgen Drews, (2000) "Drug Discovery: A Historical Perspective," Science 287:1960–1964.

A common limitation of GPCR-targeted drugs is a patient's ability to gain tolerance or resistance to such drugs. This tolerance is attributed to the fact that GPCRs desensitize (i.e., turn off) their G protein signaling pathways in response to constant drug exposure.

One possible approach to overcoming GPCR-based drug tolerance is to inhibit GPCR desensitization with compositions having GPCR desensitization inhibitory activity. Because several hundred human GPCRs are known, and because it is estimated that a couple thousand GPCRs exist in the human genome, it would be desirable to provide a method of screening compositions for inhibitory effect on GPCR desensitization that is not receptor specific.

SUMMARY OF THE INVENTION

The methods of the present invention involve screening a test composition for an indication of GPCR desensitization inhibitory activity against two or more GPCRs that are different from each other. When there is an indication that a particular test composition has GPCR desensitization inhibitory activity with respect to each of the two or more GPCRs that are different from one another, then, according to the present invention, there is an indication that the test composition has non-receptor-specific GPCR desensitization inhibitory activity.

In one aspect, a method is provided of screening a composition for non-receptor-specific GPCR desensitization inhibitory activity using two different cells. A first cell is provided comprising a first GPCR and a first conjugate of a marker molecule and a protein associated with the desensitization pathway of the first GPCR. The first GPCR is a GPCR that requires agonist for desensitization or is a constitutively desensitized GPCR. The first cell is exposed to a test composition and, when the first GPCR requires agonist for desensitization, to an agonist for the first GPCR. A determination is made, through detection of the marker molecule in the first conjugate, whether or not the composition gives an indication of GPCR desensitization inhibitory activity with respect to the first GPCR. A second cell is provided comprising a second GPCR that is different from the first GPCR and a second conjugate of a marker molecule and a protein associated with the desensitization pathway of the second GPCR. The second GPCR is a GPCR that requires agonist for desensitization or is a constitutively desensitized GPCR. The second conjugate may be the same or different from the first conjugate. The second cell is exposed to the test composition and, when the second GPCR requires agonist for desensitization, to an agonist for the second GPCR. A determination is made, through detection of the marker molecule in the second conjugate, whether or not the composition gives an indication of GPCR desensitization inhibitory activity with respect to the second GPCR. An indication of GPCR desensitization inhibitory activity for the test composition with respect to both the first and the second GPCRs is an indication that the test composition has non-receptor-specific GPCR desensitization inhibitory activity.

The determination of whether or not the composition gives an indication of GPCR desensitization inhibitory activity with respect to a GPCR can be made in various ways. For example, the determination could be made by detecting for translocation or localization of a conjugate (e.g., the first or the second conjugate) in a test cell, a lack of translocation or localization being an indication that the composition has GPCR desensitization inhibitory activity. As another example, the determination could be made by detecting for translocation or localization of a conjugate in a test cell, a decrease in translocation or localization after exposure to the test composition being an indication that the composition has GPCR desensitization inhibitory activity. As yet another example, the determination could be made by detecting for translocation or localization of a conjugate in a test cell, a decreased level of translocation or localization in the test cell with respect to a predetermined level or with respect to a level of translocation or localization determined in a control cell not exposed to the test composition being an indication that the composition has GPCR desensitization inhibitory activity. The control cell may comprise the same GPCR and conjugate used in the test cell and may be exposed to agonist if the GPCR requires agonist for desensitization.

In another aspect of the invention, a method is provided of screening a composition for non-receptor-specific G-protein coupled receptor (GPCR) desensitization inhibitory activity using one cell. A cell is provided comprising (1) a first GPCR that is a GPCR that requires agonist for desensitization; (2) a second GPCR that is different than the first GPCR, the second GPCR being a GPCR that requires agonist for desensitization; (3) a first conjugate of a marker molecule and a protein associated with the desensitization pathway of the first GPCR; and (4) a second conjugate of a marker molecule and a protein associated with the desensitization pathway of the second GPCR. The second conjugate may be the same or different from the first conjugate. The cell is exposed to a test composition and to an agonist for the first GPCR and a determination is made whether or not the composition has GPCR desensitization inhibitory activity with respect to the first GPCR. The cell is also exposed to an agonist for the second GPCR (and optionally re-exposed to the test composition) and a determination is made whether or not the composition has GPCR desensitization inhibitory activity with respect to the second GPCR. An indication that the test composition has GPCR desensitization inhibitory activity with respect to both the first GPCR and the second GPCR is an indication that the test composition has non-receptor-specific GPCR desensitization inhibitory activity. In the method, the agonist for the first GPCR is not an agonist for the second GPCR and the agonist for the second GPCR is not an agonist for the first GPCR. As above, the determination of whether or not the composition gives an indication of GPCR desensitization inhibitory activity with respect to a GPCR can be made in various ways.

In yet another embodiment of the invention, another method of screening a composition for non-receptor-specific G-protein coupled receptor (GPCR) desensitization inhibitory activity using one cell is provided. A cell is provided comprising (1) a first GPCR that is a GPCR that requires agonist for desensitization or is a constitutively desensitized GPCR, (2) a second GPCR that is different than the first GPCR, the second GPCR being a GPCR that requires agonist for desensitization or being a constitutively desensitized GPCR. (3) a first conjugate of a first marker molecule and a protein associated with the desensitization pathway of the first GPCR, and (4) a second conjugate of a second marker molecule and a protein associated with the desensitization pathway of the second GPCR, the second conjugate being different from the first conjugate. The protein of the first conjugate is not included in the desensitization pathway of the second GPCR and the protein in the second conjugate is not included in the desensitization pathway of the first GPCR. In addition, the first and second marker molecules are different from each other and are distinguishable from each other upon detection. The cell is exposed (1) to a test composition, (2) when the first GPCR requires agonist for desensitization, to an agonist for the first GPCR, and (3) when the second GPCR requires agonist for desensitization, to an agonist for the second GPCR and a determination is made whether or not the composition has GPCR desensitization inhibitory activity with respect to the first GPCR and with respect to the second GPCR. An indication that the test composition has GPCR desensitization inhibitory activity with respect to both the first GPCR and the second GPCR being an indication that the test composition has non-receptor-specific GPCR desensitization inhibitory activity. As above, the determination of whether or not the composition gives an indication of GPCR desensitization inhibitory activity with respect to a GPCR can be made in various ways.

BRIEF DESCRIPTION OF THE DRAWINGS

FIG. 2 is an illustrative, non-limiting list of known GPCRs that may be used with the present invention. FIGS. 2A to 2B includes a non-limiting list of the known Class I GPCRs. FIG. 2C is a non-limiting list of the known Class II and Class III GPCRs.

FIG. 3A is an illustrative, non-limiting list of known Class A receptors, including amino acid sequence for their carboxyl terminal tails (SEQ ID NOS:1–9). FIG. 3B is an illustrative, non-limiting list of known Class A receptors, including amino acid sequence for their carboxyl terminal tails (SEQ ID NOS:10–20). FIG. 3C is an illustrative, non-limiting list of known Class A and Class B receptors, including amino acid sequence for their carboxyl terminal tails, and the residues that function as phosphorylation sites in the enhanced affinity motifs are shown in bolded italics (SEQ ID NOS:21–30). FIG. 3D is an illustrative, non-limiting list of known Class A and Class B receptors, including amino acid sequence for their carboxyl terminal tails, and the residues that function as phosphorylation sites in the enhanced affinity motifs are shown in bolded italics (SEQ ID NOS:31–39).

FIGS. 4A–C illustrate the amino acid sequences of the following GPCRs in which the DRY motif has been modified: Vasopressin V2 Receptor (V2R), Alpha-1B Adrenergic Receptor ($\alpha_{1B}$-AR), and Angiotensin II Receptor, Type 1 ($AT_{1A}R$). FIG. 4A illustrates the amino acid sequence of the V2R R137H mutation (SEQ ID NO:40), with the amino acids differing from the wild type sequence in bold and underlined. FIG. 4B illustrates the $\alpha_{1B}$-AR R143E mutation (SEQ ID NO:41) the α1B-AR R143A mutation (SEQ ID NO:42), the $\alpha_{1B}$-AR R143H mutation (SEQ ID NO:43), and the $\alpha_{1B}$-AR R143N mutation (SEQ ID NO:44). Amino acids that differ from the wild-type sequence are in bold and underlined. FIG. 4C illustrates the $AT_{1A}AR$ R126H mutation (SEQ ID NO:45). Amino acids that differ from the wild-type sequence are in bold and underlined.

FIGS. 5A–5J are a list of amino acid and nucleic acid sequences of the following GPCRs that have been modified to have enhanced affinity for arrestin: hGPR3-Enhanced receptor, hGPR6-Enhanced receptor, hGPR12-Enhanced receptor, hSREB3-Enhanced receptor, hSREB2-Enhanced receptor, hGPR8-Enhanced receptor, and hGPR22-Enhanced receptor. FIGS. 5A and 5B respectively illustrate the amino acid sequence (SEQ ID NO:46) and the nucleic acid sequence (SEQ ID NO:47) of the hGPR3-Enhanced receptor. FIGS. 5C and 5D respectively illustrate the amino acid sequence (SEQ ID NO:48) and the nucleic acid sequence (SEQ ID NO:49) of the hGPR6-Enhanced receptor. FIGS. 5E and 5F respectively illustrate the amino acid sequence (SEQ ID NO:50) and the nucleic acid sequence (SEQ ID NO:51) of the hGPR12-Enhanced receptor. FIGS. 5G and 5H respectively illustrate the amino acid sequence (SEQ ID NO:52) and the nucleic acid sequence (SEQ ID NO:53) of the hSREB3-Enhanced receptor. FIGS. 5I and 5J respectively illustrate the amino acid sequence (SEQ ID NO:54) and the nucleic acid sequence (SEQ ID NO:55) of the hSREB2-Enhanced receptor. FIGS. 5K and 5L respectively illustrate the amino acid sequence (SEQ ID NO:56) and the nucleic acid sequence (SEQ ID NO:57) of the hGPR8-Enhanced receptor. FIGS. 5M and 5N respectively illustrate the amino acid sequence (SEQ ID NO:58) and the nucleic acid sequence (SEQ ID NO:59) of the hGPR22-Enhanced receptor.

FIG. 6 lists GPCRs that have been modified to have enhanced affinity for arrestin. FIG. 6A shows the amino acid sequence, termed SEQ ID NO.:60, of the $\beta_2$AR-V2R chimera. FIG. 6B shows the amino acid sequence, termed SEQ ID NO.:61, of the MOR-V2R chimera. FIG. 6C shows the amino acid sequence, termed SEQ ID NO.:62, of the D1AR-V2R chimera. FIG. 6D shows the amino acid sequence, termed SEQ ID NO.:63, of the 5HT1AR-V2R chimera. FIG. 6E shows the amino acid sequence, termed SEQ ID NO.:64, of the $\beta_3$AR-V2R chimera. FIG. 6F shows the amino acid sequence, termed SEQ ID NO.:65, of the Edg1R-V2R chimera.

FIGS. 7–21 illustrate concentration-response plots for test compositions and FIG. 22 illustrates the concentration-response plot of a control compound as described in the Example below.

DETAILED DESCRIPTION OF THE INVENTION

Figure 1:
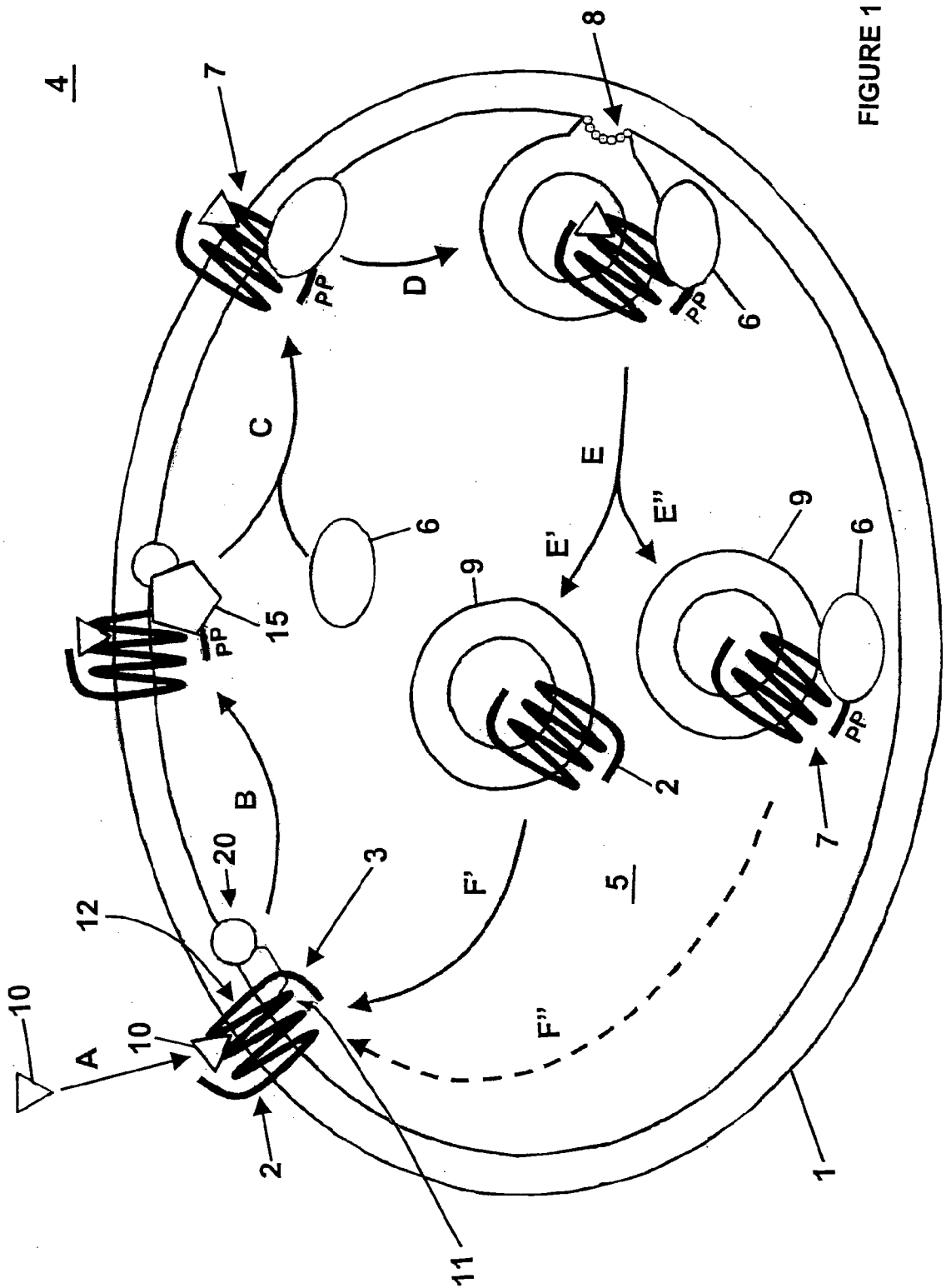
FIG. 1 illustrates an example of a desensitization pathway of a GPCR in response to an agonist. Reference numerals in FIG. 1 correspond to items depicted therein as follows: cell membrane-1; GPCR or GPCR-marker molecule conjugate-2; carboxyl terminal tail of GPCR-3; extracellular region-4; intracellular region/cytosol-5; arrestin protein or arrestin-marker molecule conjugate-6; GPCR-arrestin protein complex-7; clathrin-coated pit/vesicle-8; endosome-9; agonist for GPCR-10; third intracellular loop-11; intramembrane portion of GPCR-12; G protein-coupled receptor kinase (GRK)-15; G protein-20.
Figure 7:
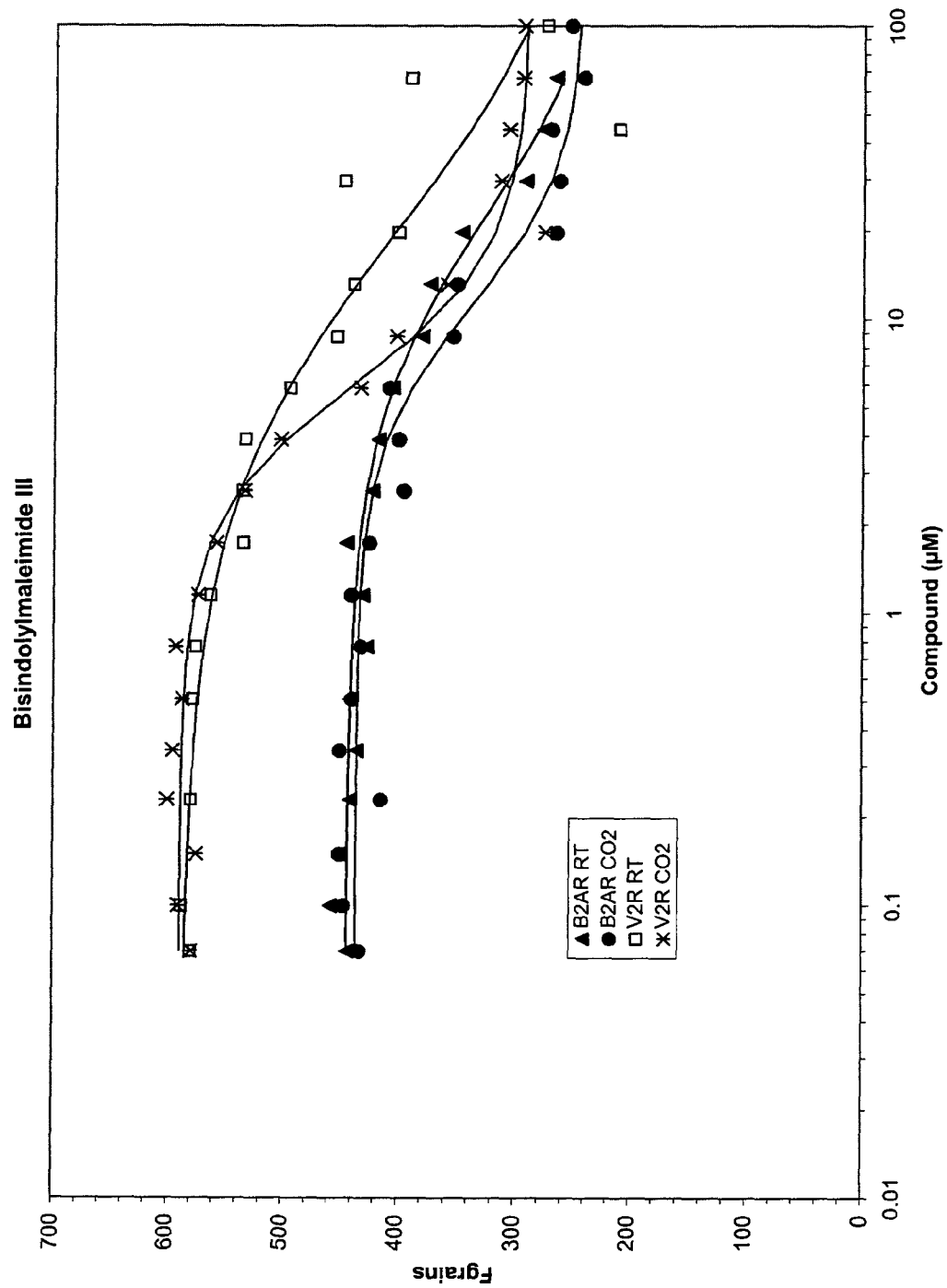
FIGS. 7–22 illustrate concentration-response plots of the average amount of fluorescent intensity of identified "grains" of arrestin-GFP localization (i.e., Fgrains) in cells expressing $\beta_2$AR and cells expressing V2R after addition of the indicated concentrations of test compound (or control compound) and addition of agonist. Each compound was tested against each receptor at room temperature and atmospheric $CO_2$ (indicated in the figures as $\beta$2AR RT and V2R RT) and at 37° C. and 5% $CO_2$/95% $O_2$ (indicated in the figures as $\beta$2AR CO2 and V2R CO2). Concentration-response curves were plotted for the assays that indicated GPCR desensitization inhibitory activity of a compound.
Figure 8:
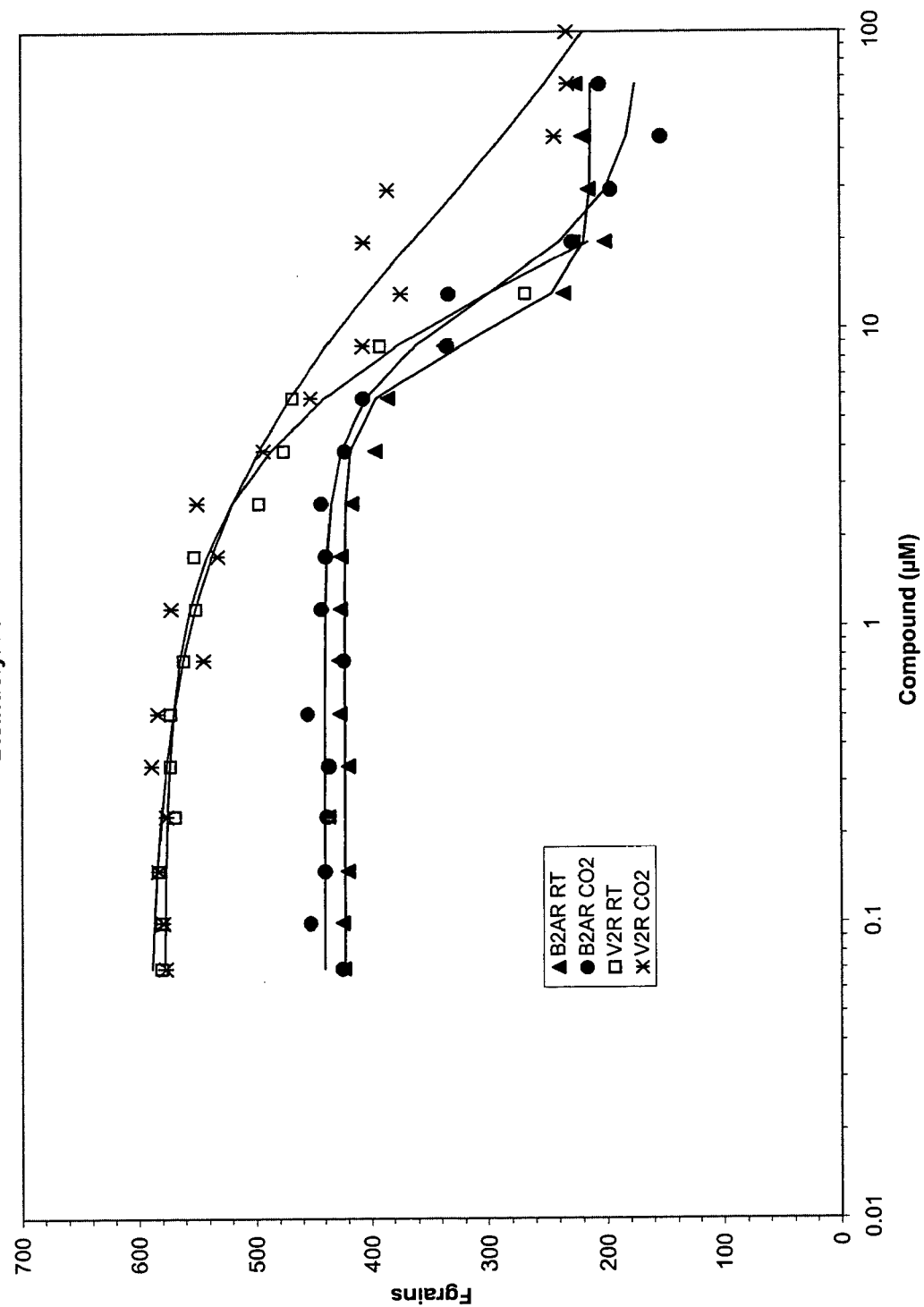
Figure 9:
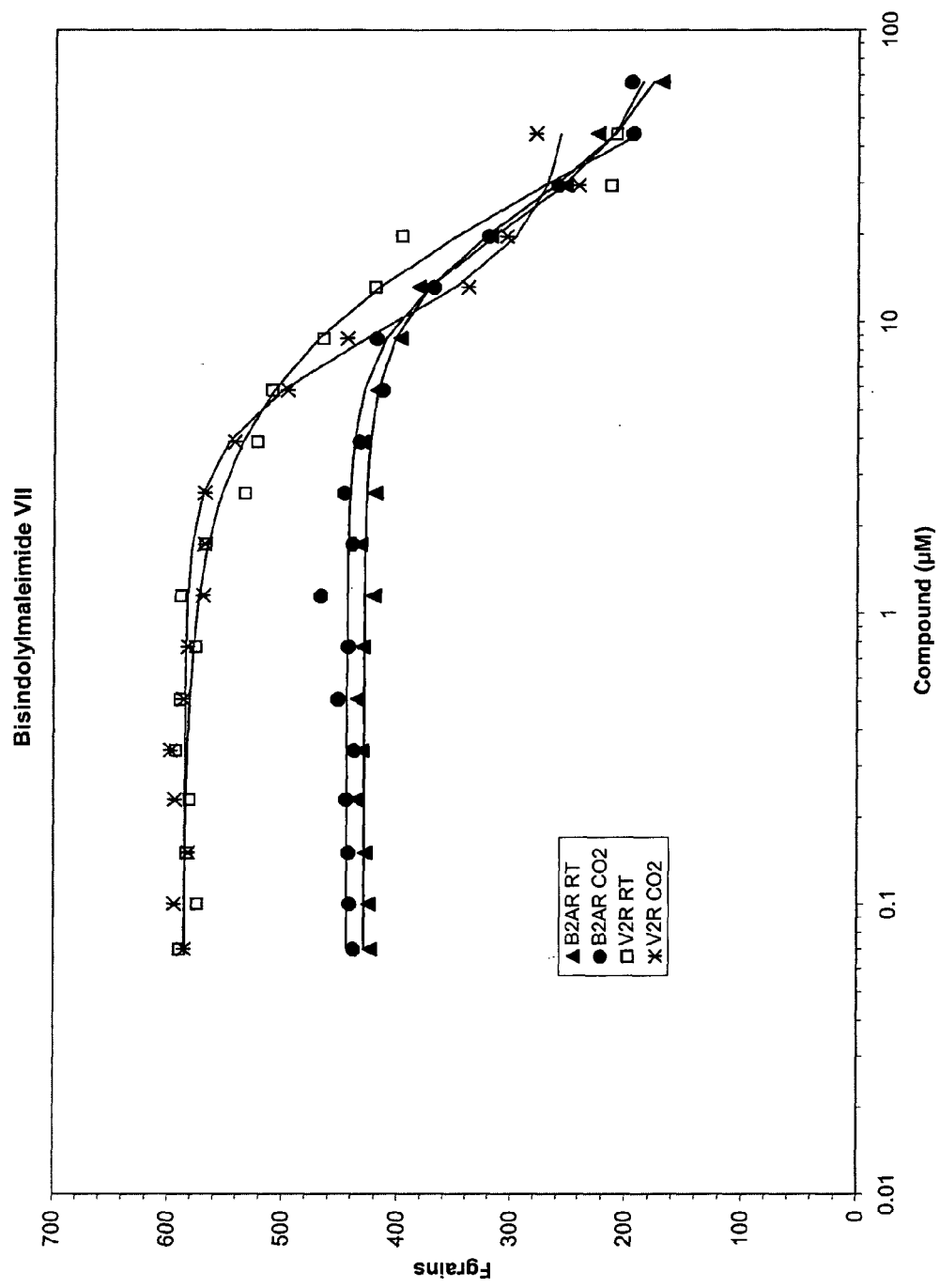
Figure 10:
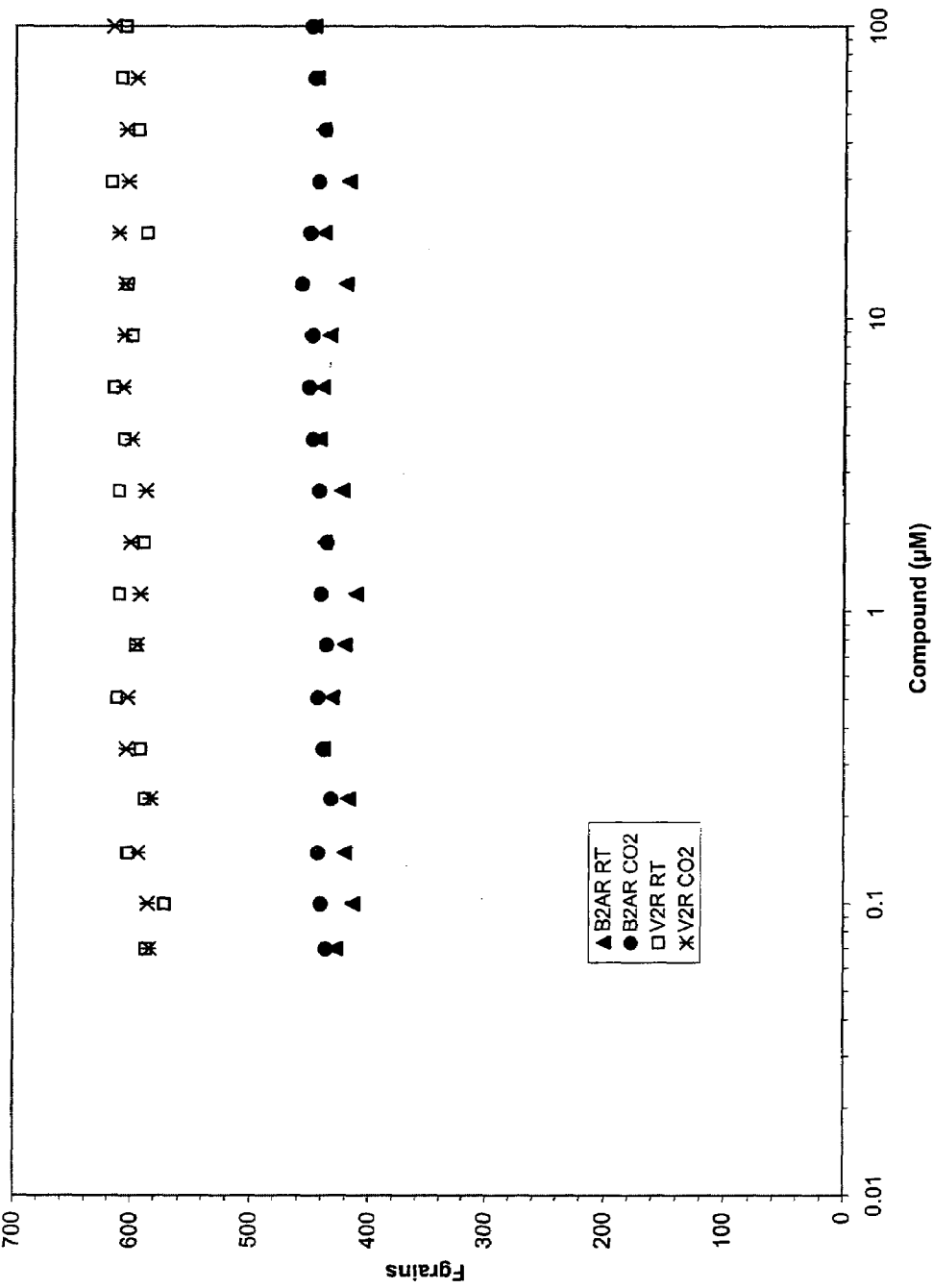
Figure 11:
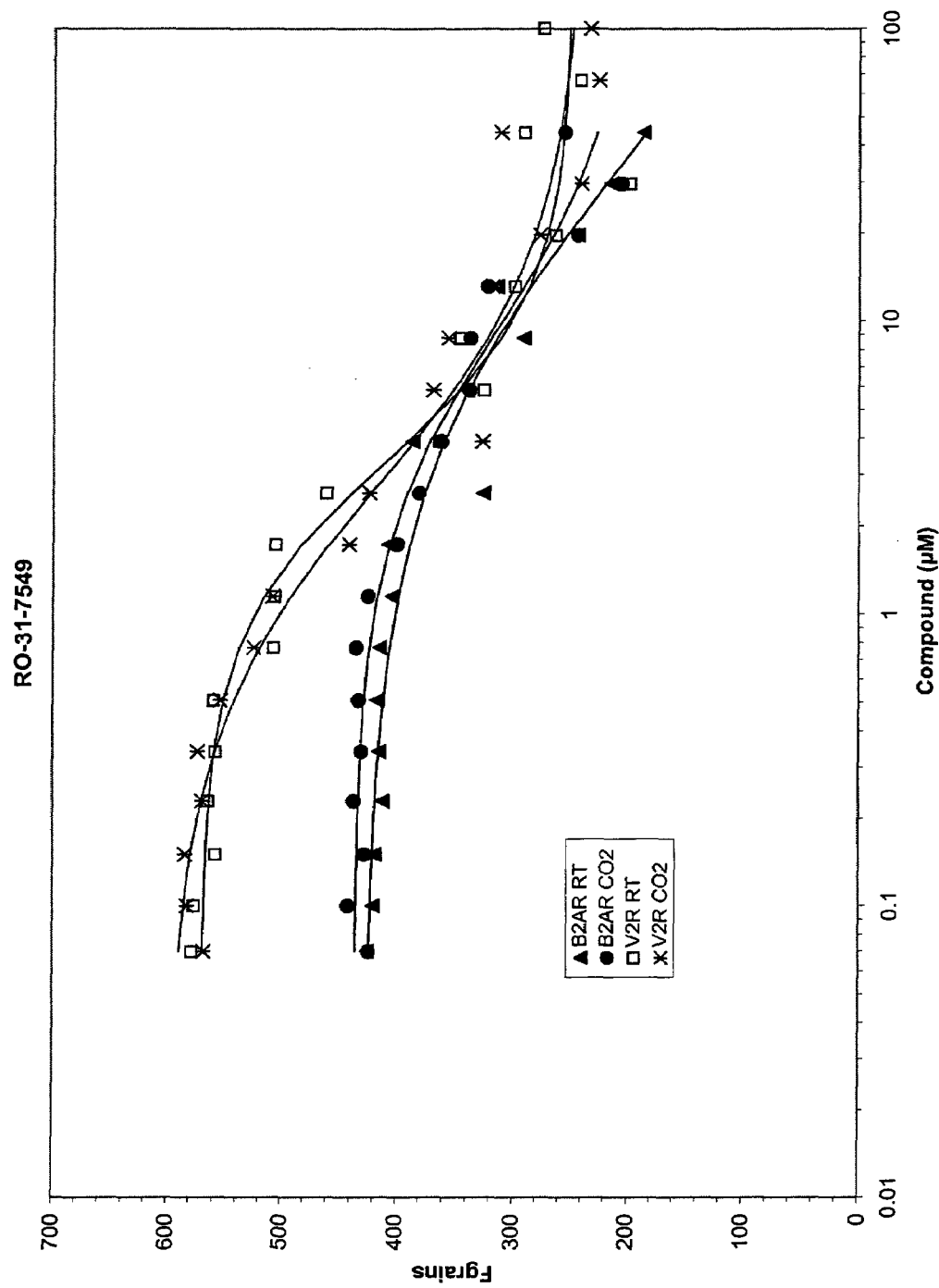
Figure 12:
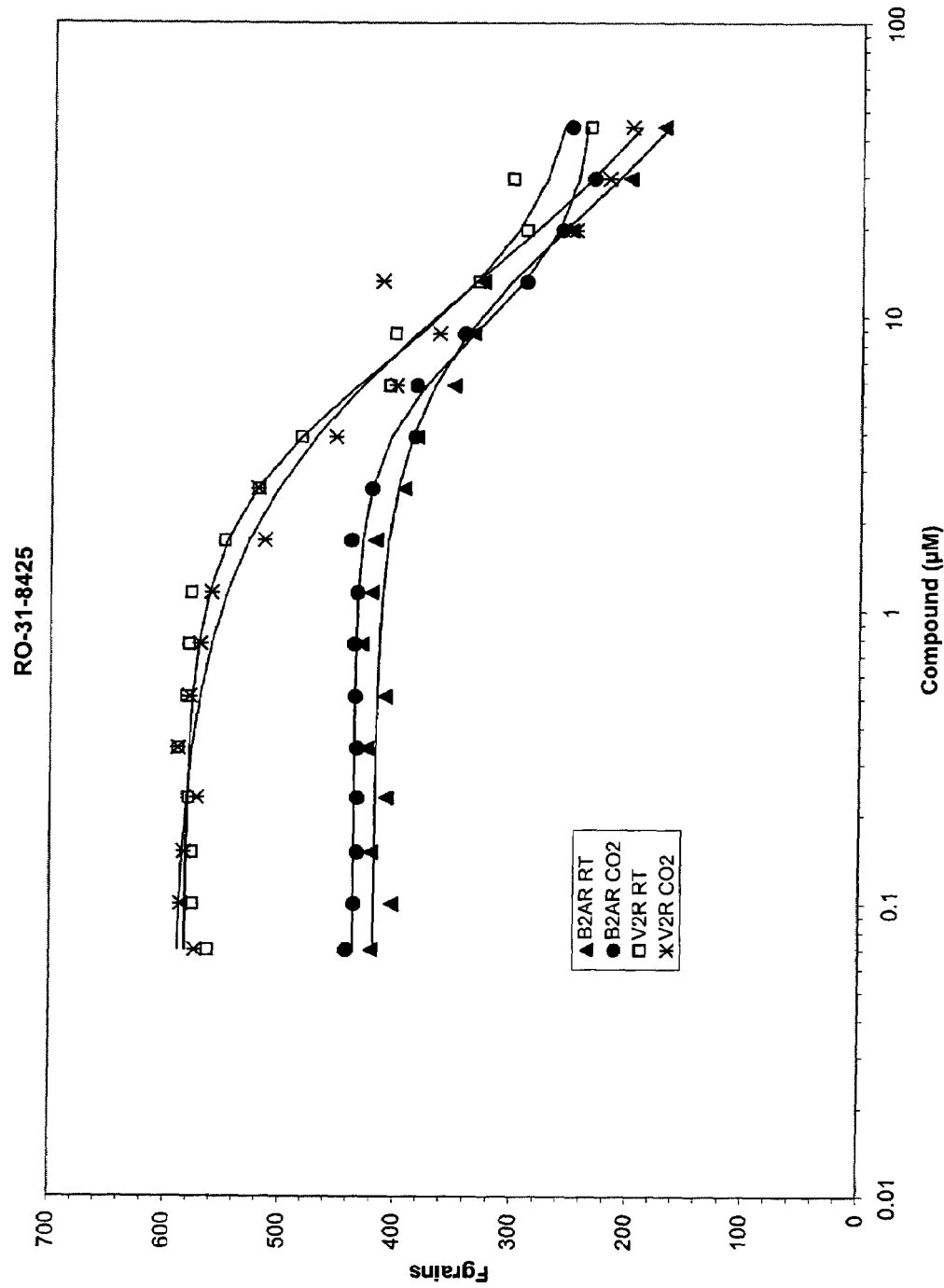
Figure 13:
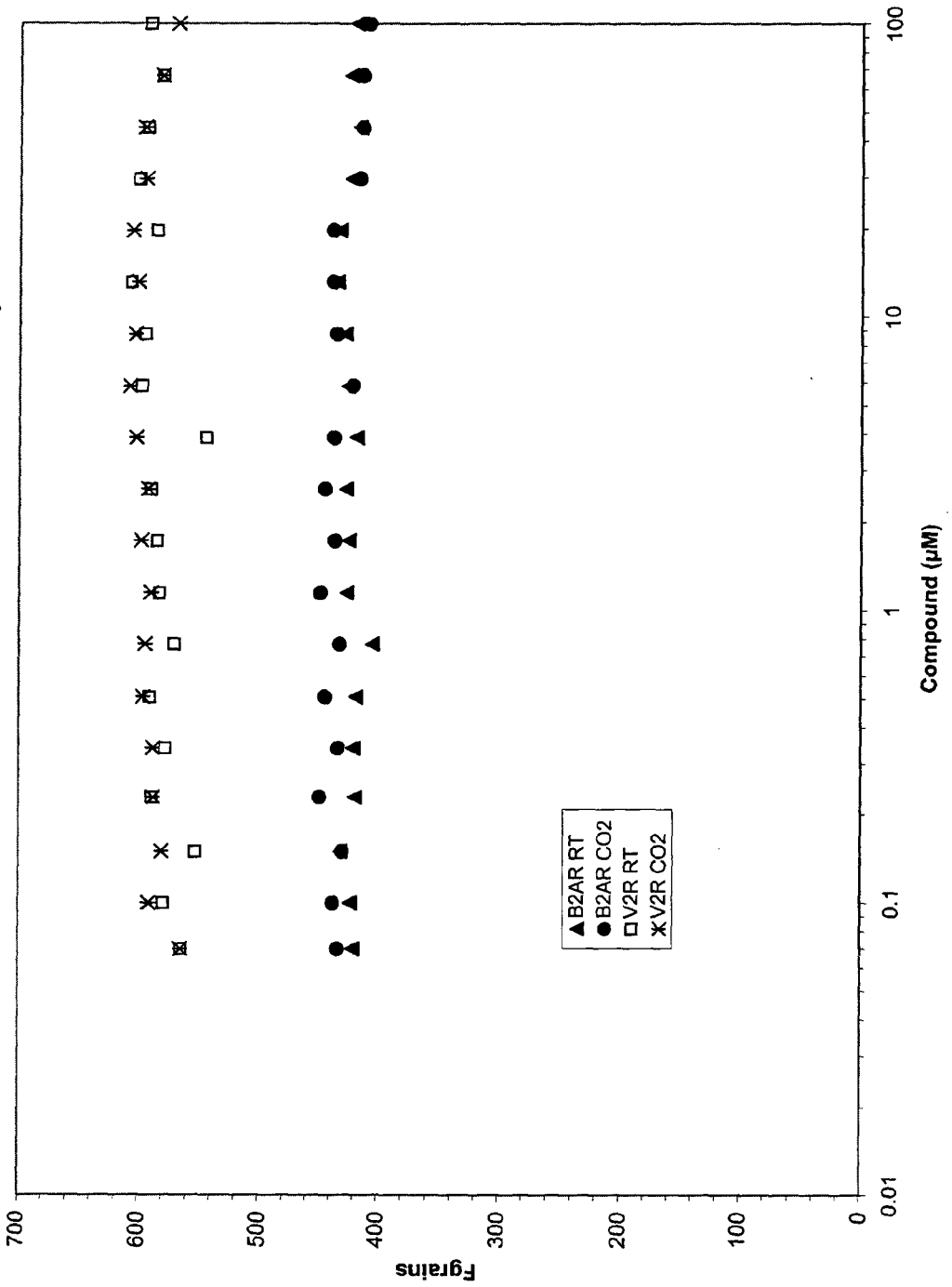
Figure 14:
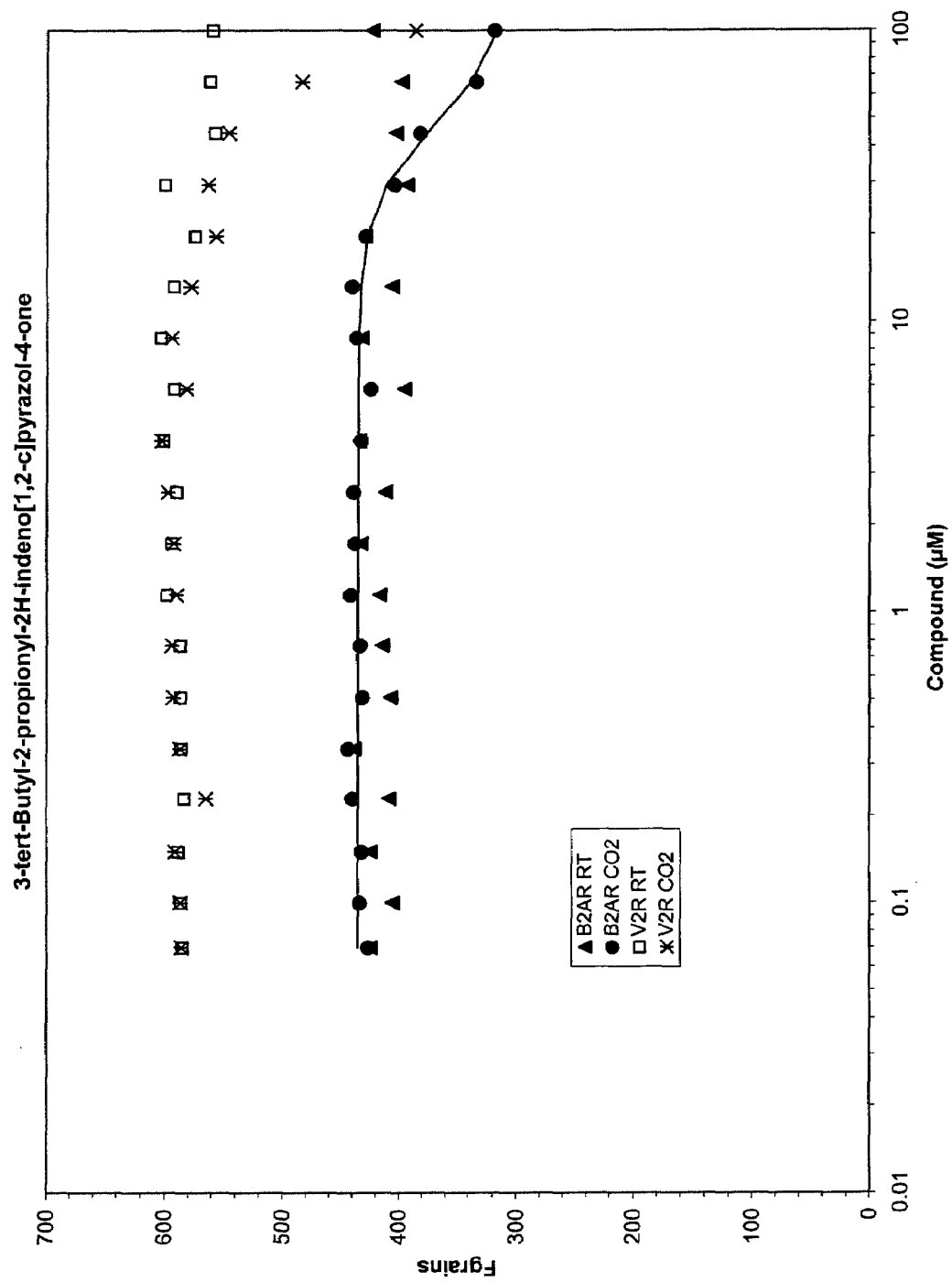
Figure 15:
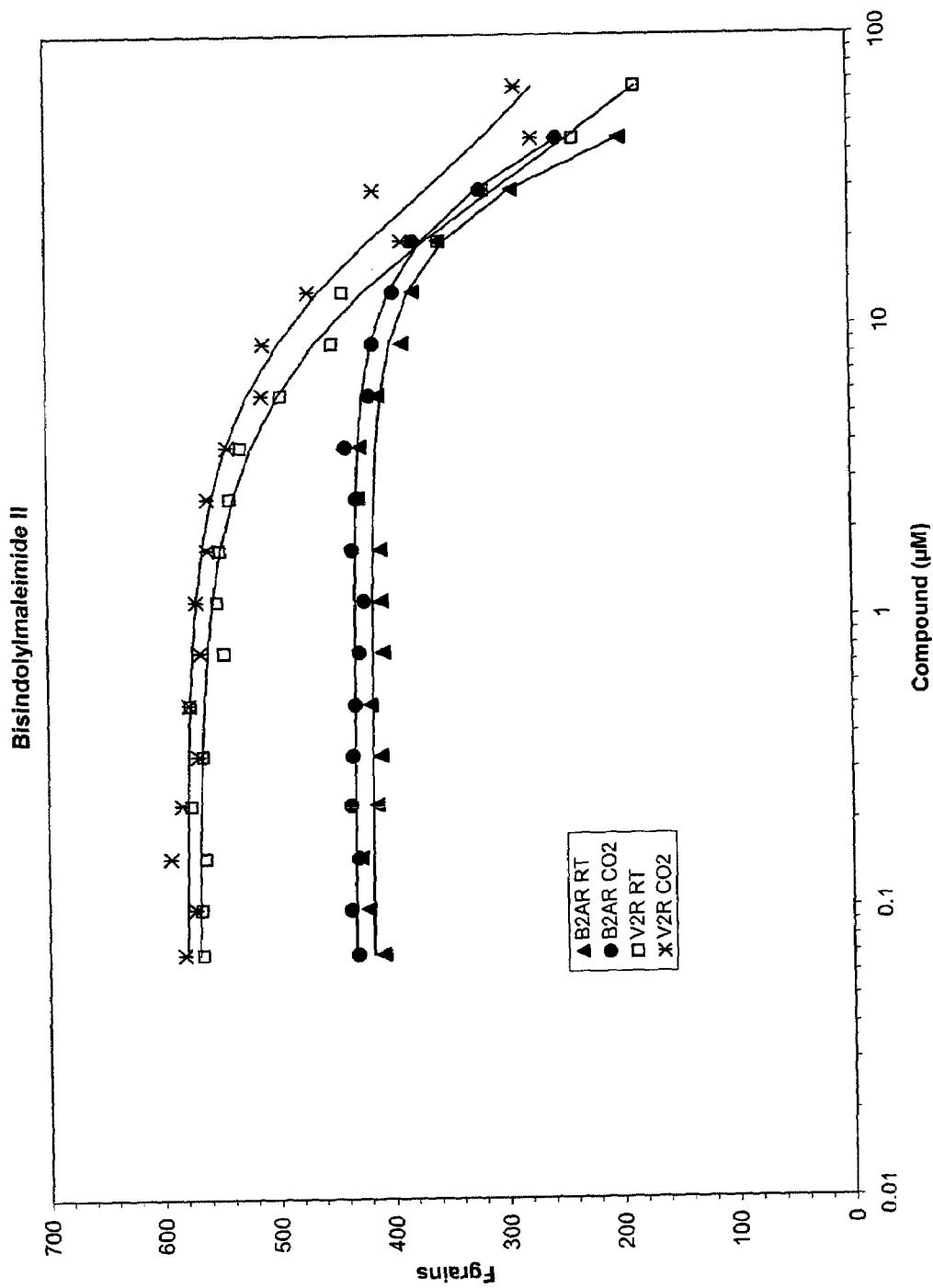
Figure 16:
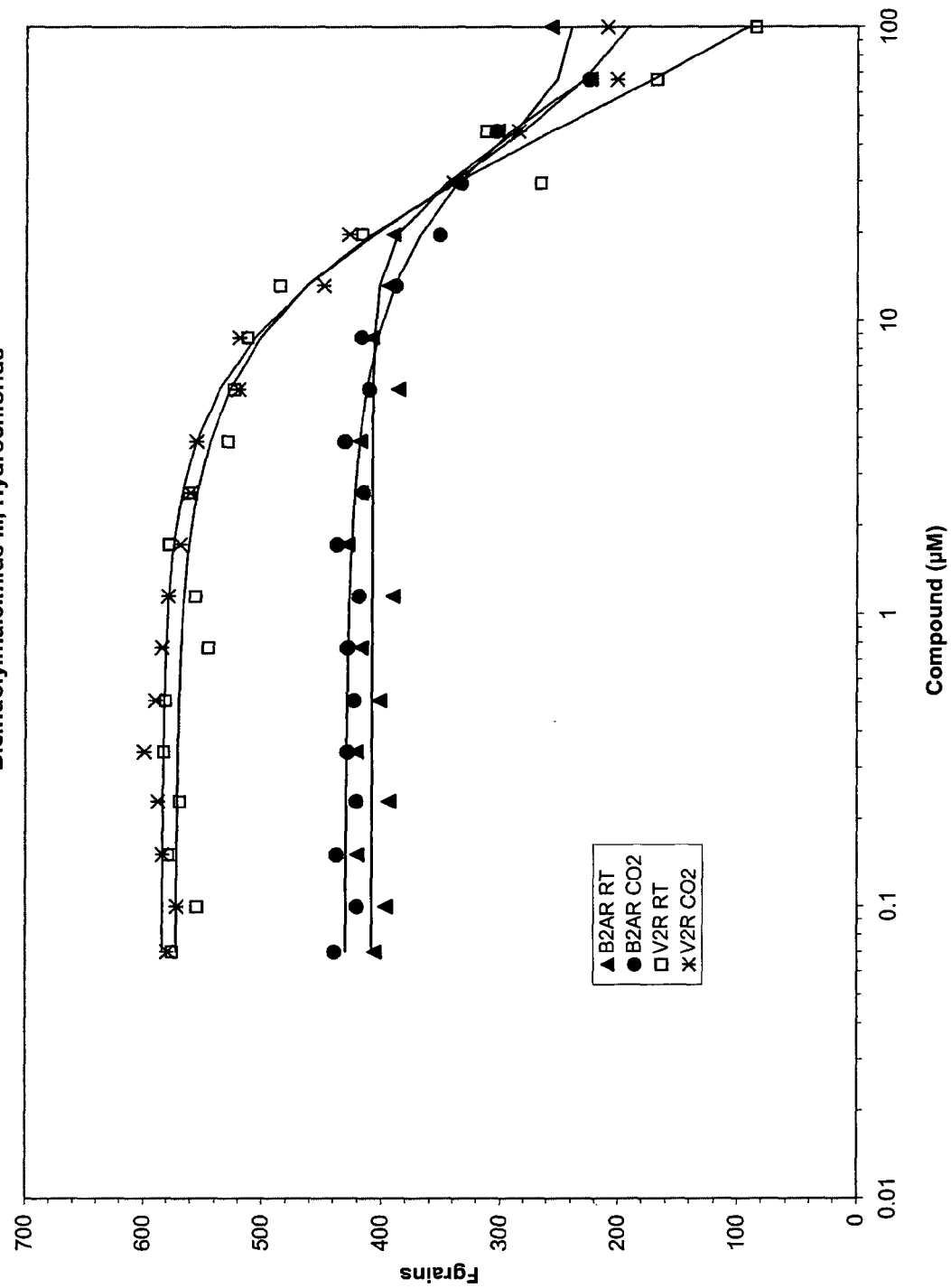
Figure 17:
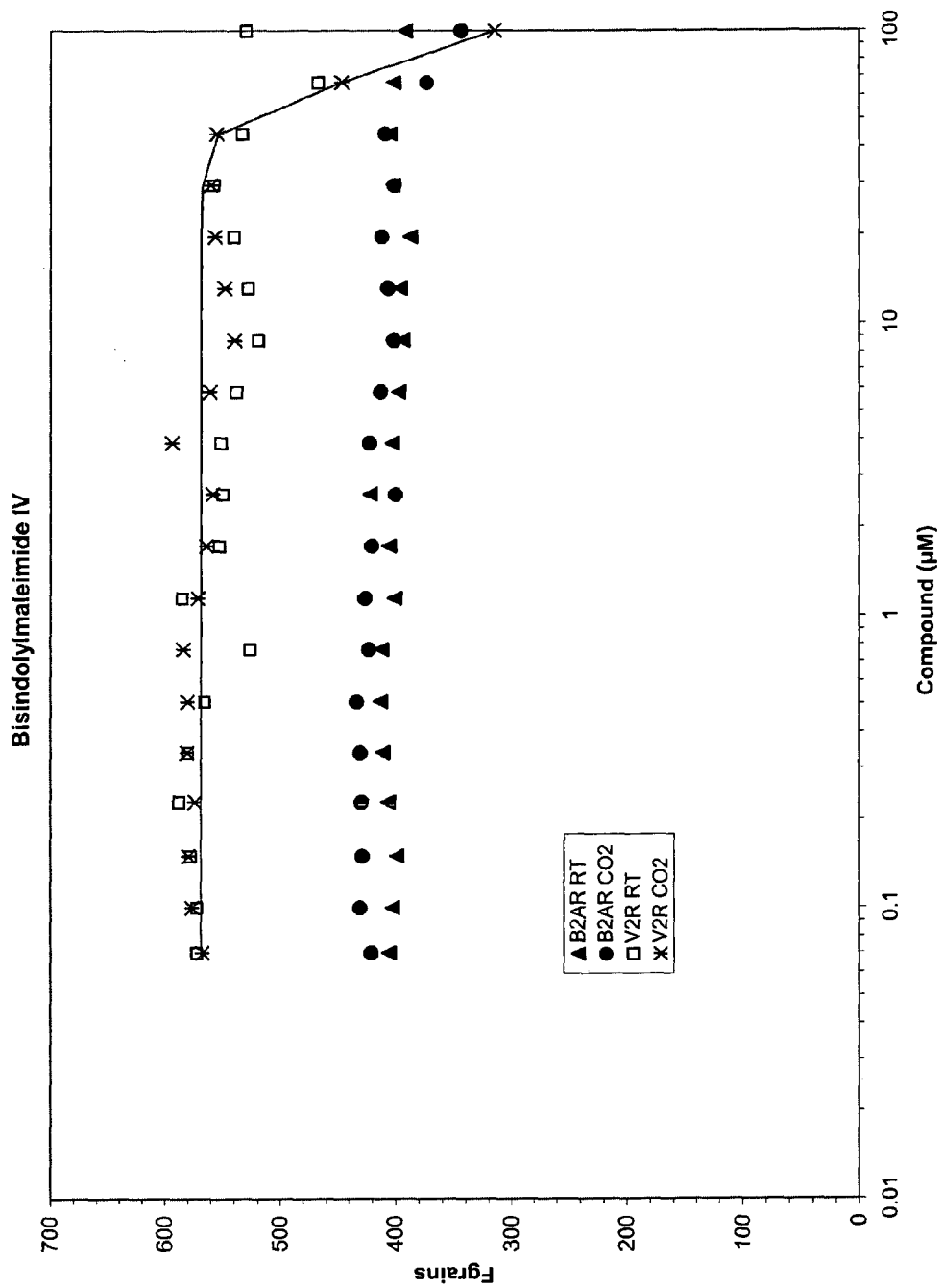
Figure 18:
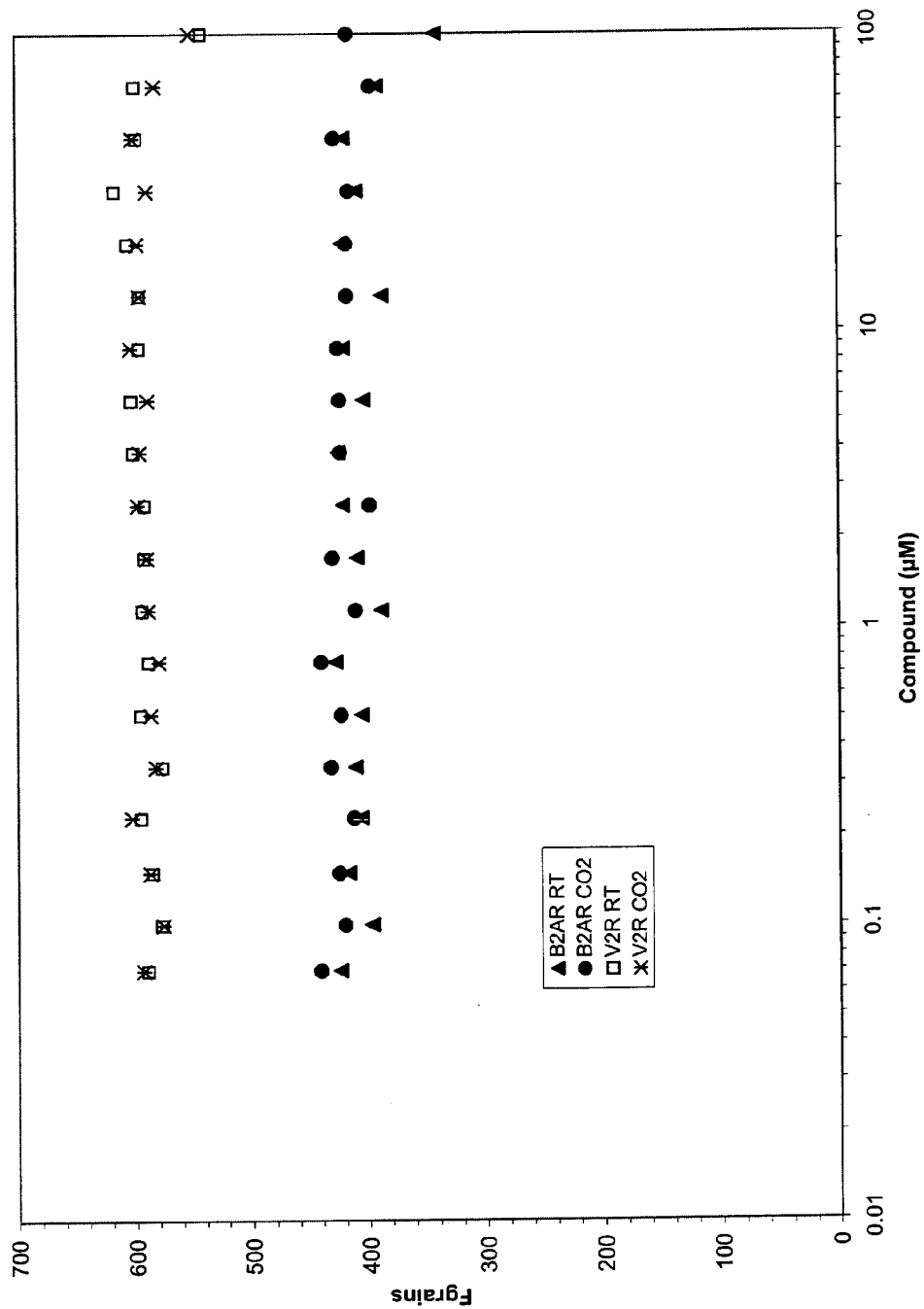
Figure 19:
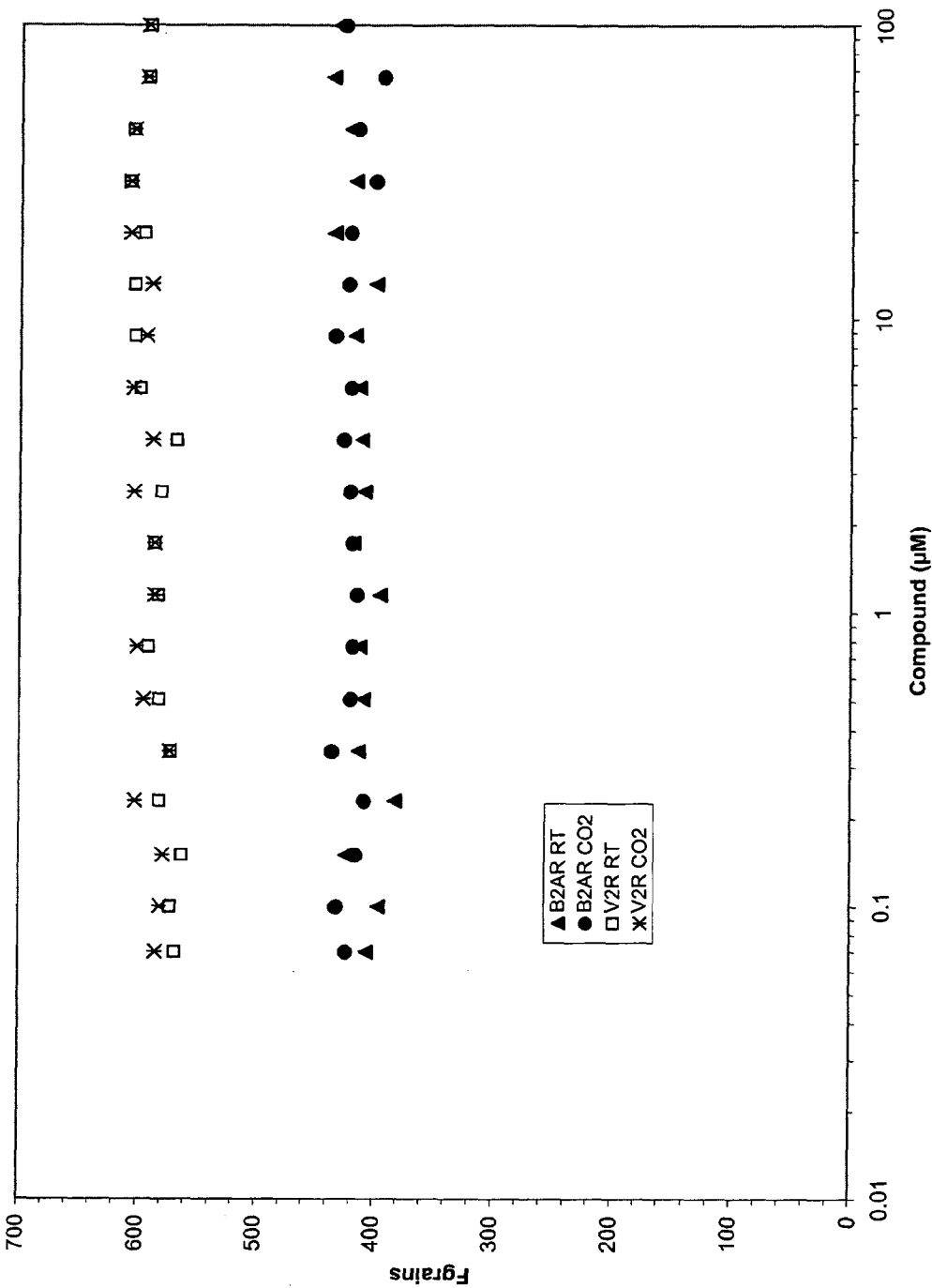
Figure 20:
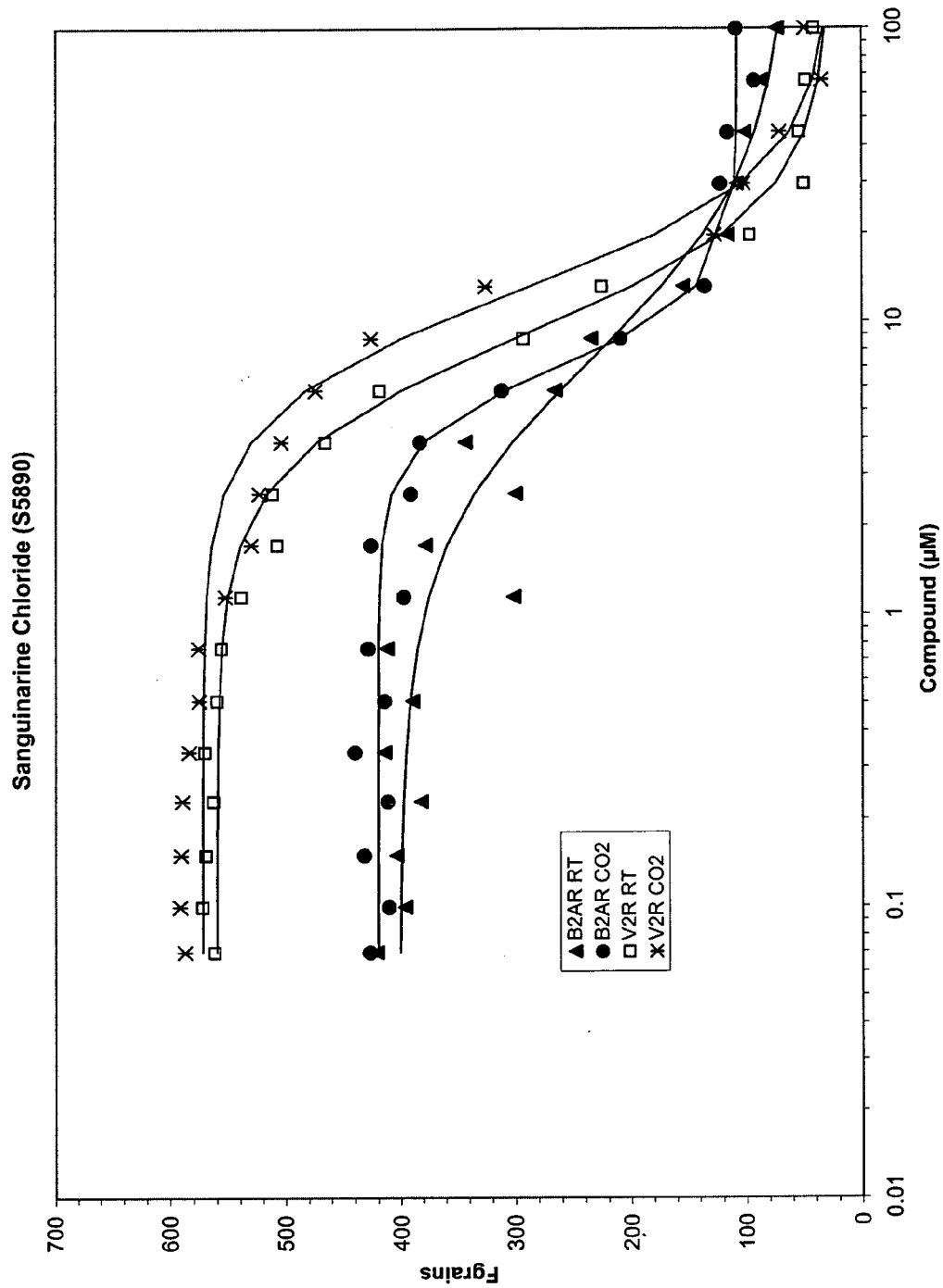
Figure 21:
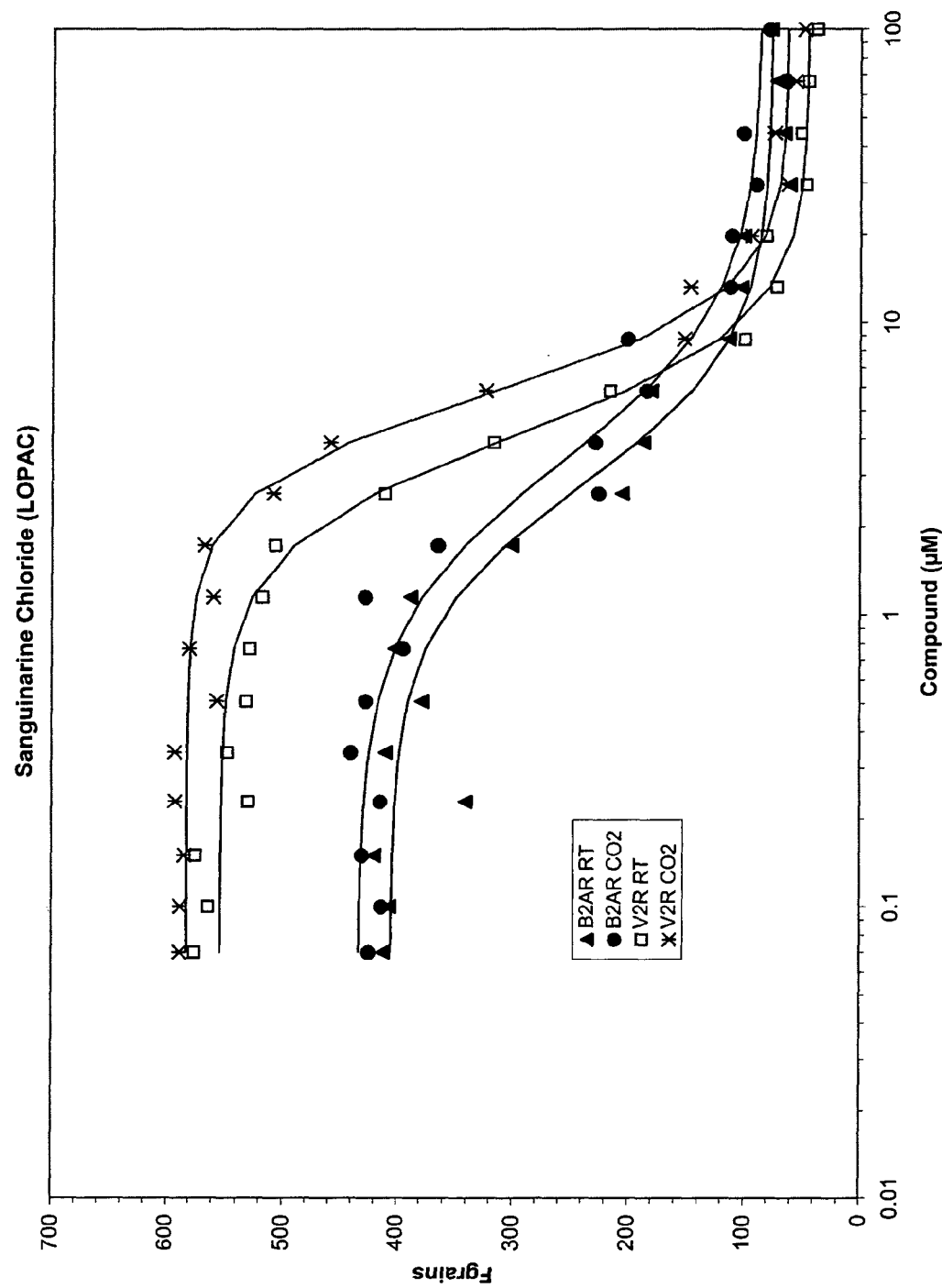
Figure 22:
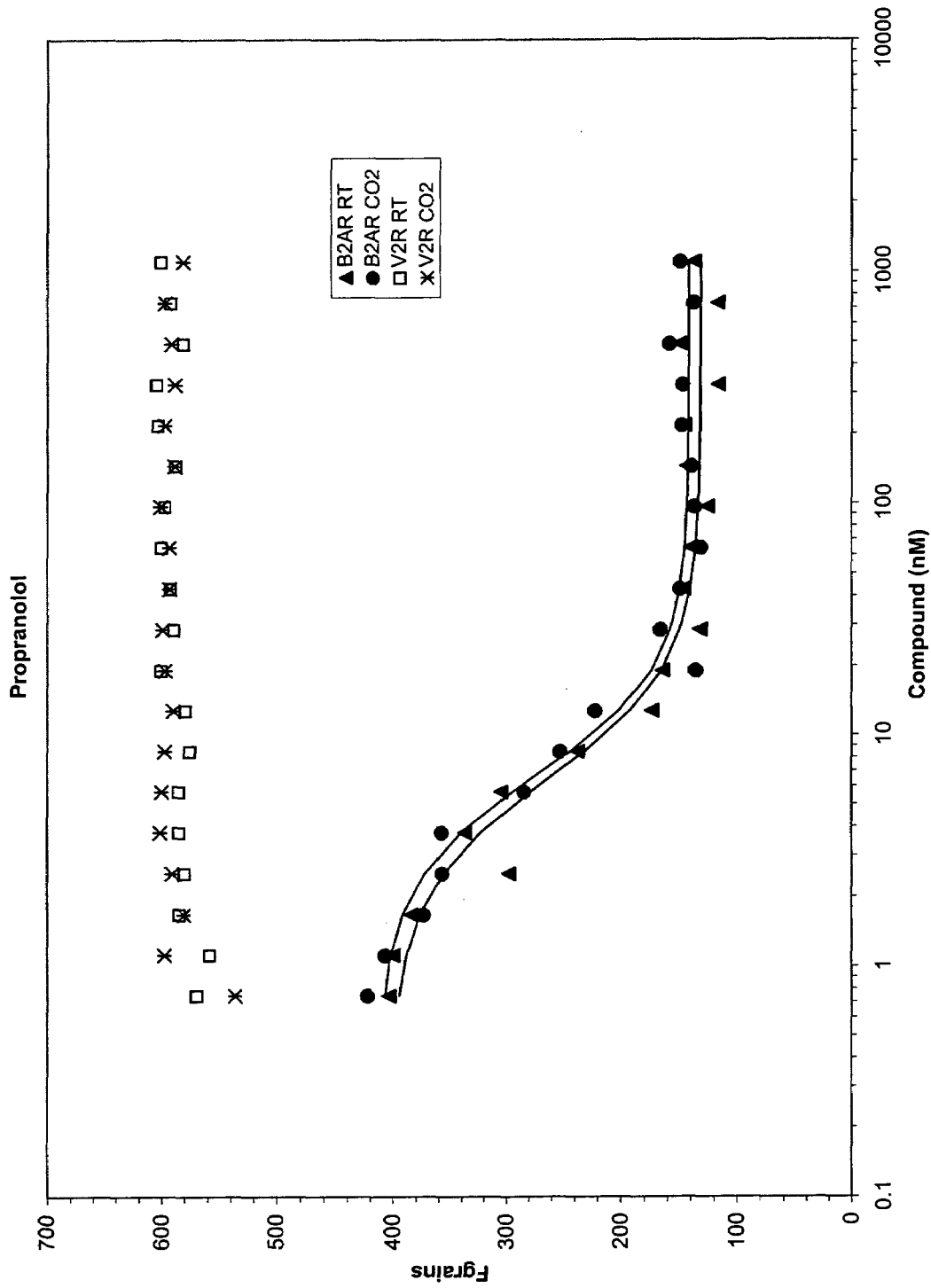

The present invention relates to methods of screening compositions for GPCR desensitization inhibitory activity that is not specific to a particular receptor. Prior to describing this invention in further detail, however, the following terms will first be defined.

Definitions

"Arrestin" means all types of naturally occurring and engineered variants of arrestin, including, but not limited to, visual arrestin (sometimes referred to as Arrestin 1), cone arrestin (sometimes referred to as arrestin-4), β-arrestin 1 (sometimes referred to as Arrestin 2), and β-arrestin 2 (sometimes referred to as Arrestin 3). "Arrestin" also includes biologically active fragments of arrestin.

"Biologically active fragment" of an arrestin means a fragment of arrestin that has the ability to bind a wild-type and/or modified GPCR.

An "antibody" is any immunoglobulin, including antibodies and fragments thereof, that bind a specific epitope.

"Carboxyl-terminal tail" means the carboxyl-terminal tail of a GPCR following membrane span 7. The carboxyl-terminal tail of many GPCRs begins shortly after the conserved NPXXY motif that marks the end of the seventh transmembrane domain (i.e. what follows the NPXXY motif is the carboxyl-terminal tail of the GPCR). The carboxyl-terminal tail may be relatively long (approximately tens to hundreds of amino acids), relatively short (approximately tens of amino acids), or virtually non-existent (less than approximately ten amino acids). As used herein, "carboxyl-terminal tail" shall mean all three variants (whether relatively long, relatively short, or virtually non-existent), and may or may not contain palmitoylated cysteine residue(s).

"Marker molecule" means any molecule capable of detection by spectroscopic, photochemical, biochemical, immunochemical, electrical, radioactive, and optical means, including but not limited to, fluorescence, phosphorescence, and bioluminescence and radioactive decay. Marker molecules include, but are not limited to, GFP, luciferase, β-galactosidase, rhodamine-conjugated antibody, and the like. Marker molecules include radioisotopes, epitope tags, affinity labels, enzymes, fluorescent groups, chemiluminescent groups, and the like. Marker molecules include molecules that are directly or indirectly detected as a function of their interaction with other molecule(s).

"GFP" means Green Fluorescent Protein, which refers to various naturally occurring forms of GFP that may be isolated from natural sources or genetically engineered, as well as artificially modified GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered, including but not limited to, yellow fluorescent proteins (YFP), red fluorescent proteins (RFP), cyan fluorescent proteins (CFP), blue fluorescent proteins, luciferin, UV excitable fluorescent proteins, or any wave-length in between. As used herein, "GFP" shall mean all fluorescent proteins known in the art.

"Downstream" means toward a carboxyl-terminus of an amino acid sequence, with respect to the amino-terminus.

"Upstream" means toward an amino-terminus of an amino acid sequence, with respect to the carboxyl-terminus.

"GPCR" means G protein-coupled receptor and includes GPCRs naturally occurring in nature, as well as GPCRs that have been modified, including the GPCRs described in U.S. patent application Ser. Nos. 09/993,844 and 10/054,616 and the GPCRs described in U.S. Provisional Patent Application No. 60/401,698.

"Desensitized GPCR" means a GPCR that presently does not have ability to respond to agonist and activate conventional G protein signaling.

"Sensitized GPCR" means a GPCR that presently has ability to respond to agonist and activate conventional G protein signaling.

"GPCR desensitization pathway" means any cellular component of the GPCR desensitization process, as well as any cellular structure implicated in the GPCR desensitization process and subsequent processes, including but not limited to, arresting, GRKs, GPCRs, AP-2 protein, clathrin, protein phosphatases, and the like.

"GPCR signaling" means GPCR induced activation of G proteins. This may result in, for example, cAMP production.

"G protein-coupled receptor kinase" (GRK) includes any kinase that has the ability to phosphorylate a GPCR.

An "overexpressed" protein refers to a protein that is expressed at levels greater than wild-type expression levels.

"Restriction enzymes" refers to bacterial enzymes, each of which cut double-stranded DNA at or near a specific nucleotide sequence.

"Unknown Receptor" or "Orphan Receptor" means a GPCR whose endogenous ligand(s) is/are unknown.

A "vector" is a replicon, such as plasmid, phage or cosmid, to which another DNA segment may be attached so as to bring about the replication of the attached segment.

"GPCR desensitization inhibitory activity" of a composition (e.g., compound, solution, etc.) means that the composition is capable of inhibiting GPCR desensitization of at least one specific GPCR.

"Non-receptor-specific GPCR desensitization inhibitory activity" of a composition (e.g., compound, solution, etc.) means that the composition is capable of inhibiting GPCR desensitization of two or more specific GPCRs. In some embodiments, compositions with "non-receptor-specific GPCR desensitization inhibitory activity" may be capable of inhibiting GPCR desensitization in all or a portion of the GPCRs in a specified class (e.g., class A, class B, class I, class II, class III, etc.) and/or a specified family (e.g., serotonin, opioid, adenosine, adrenergic, dopamine, GABA, etc.). Compositions with "non-receptor-specific GPCR desensitization inhibitory activity" may inhibit GPCR desensitization by affecting, either directly or indirectly, one or more cellular components of the GPCR desensitization pathway other than the GPCR itself such as, for example, by inhibiting a GRK or an arrestin protein.

An "indication" of GPCR desensitization inhibitory activity or non-receptor-specific GPCR desensitization inhibitory activity means something (e.g., an event, sign, signal, etc. or the lack thereof) that indicates evidence of such activity.

"Test composition" or "composition" means any solution, compound, or other substance (including, but not limited to, small molecules such as deoxyribonucleotide (DNA) and ribonucleotide (RNA) molecules as well as peptides and proteins) to be screened according to the present invention for non-receptor-specific GPCR desensitization inhibitory activity.

"Desensitization" or "GPCR desensitization" refers generally to the process by which sensitized GPCRs are converted to desensitized GPCRs.

Methods of Screening Compositions

The methods of the present invention allow the screening of a test composition for non-receptor-specific GPCR desensitization inhibitory activity. The methods involve screening a test composition for an indication of GPCR desensitization inhibitory activity against two or more GPCRs that are different from each other. When there is an indication that a particular test composition has GPCR desensitization inhibitory activity with respect to each of the two or more GPCRs that are different from one another, then, according to the present invention, there is an indication that the test composition has non-receptor-specific GPCR desensitization inhibitory activity. Detection methods for determining whether there is an indication that a test composition has GPCR desensitization inhibitory activity are discussed below.

The methods of the present invention may be conducted using one or more cells. In one embodiment, two or more cells are used to screen a test composition for non-receptor-specific GPCR desensitization inhibitory activity. In such an embodiment, each cell expresses at least one GPCR that is different from the GPCR or GPCRs being used to screen the test composition in the other cell or cells. In such an embodiment, each cell must express (or overexpress) a GPCR such that a detection method may be used for determining whether there is an indication that a test composition has GPCR desensitization inhibitory activity with respect to that specific GPCR. The GPCR used in one of the cells to screen a test composition may be absent in the other cells that use different GPCRs for screening, may be present in the other cells that use different GPCRs for screening at a level that does not affect the screening using the different GPCRs, or may be present in the other cells that use different GPCRs for screening at the same level (or a higher or lower level) as in the cell that is using the GPCR for screening when an appropriate detection method is used that may determine an indication of GPCR desensitization inhibitory activity with respect to the appropriate GPCR.

In another embodiment, one cell is used to screen a test composition for non-receptor-specific GPCR desensitization inhibitory activity. In such an embodiment, the cell expresses (or overexpresses) two or more GPCRs that are different from each other such that a detection method may be used for determining whether there is an indication that a test composition has GPCR desensitization inhibitory activity with respect to each of the different GPCRs. As used herein, an embodiment using one cell to screen a test composition for non-receptor-specific GPCR desensitization includes using only one cell as well as using multiple cells expressing the same two or more GPCRs, and details concerning such an embodiment (i.e., using one cell) are not meant to limit the embodiment to using only one cell.

Each cell used in the methods also includes one or more conjugates comprising a marker molecule and a protein associated with the GPCR desensitization pathway of one or more of the GPCRs that are being used in the cell to screen a test composition for GPCR desensitization inhibitory activity. The conjugate or conjugates indicate, through the use of the marker molecule, GPCR desensitization inhibitory activity of a test composition with respect to each of the GPCRs that are being used to screen the test composition. The conjugates of the one or more cells may comprise, for example, an arrestin protein and a marker molecule and/or a GPCR and a marker molecule. In one embodiment, the cell or cells may comprise a conjugate of an arrestin protein and a marker molecule as well as a conjugate of a GPCR and a marker molecule.

When one cell is used to screen a test composition for non-receptor-specific GPCR desensitization inhibitory activity, the cell expresses two or more GPCRs that are different from one another (e.g., a first GPCR and a second GPCR that is different from the first GPCR). The cell also includes one or more conjugates comprising a marker molecule and a protein associated with the GPCR desensitization pathway of one or more of the GPCRs expressed in the cell. The cell will include one or more appropriate conjugates such that, through the use of the marker molecule(s) of the conjugate(s), a detection method or methods can be used to determine whether there is an indication of GPCR desensitization inhibitory activity of a test composition with respect to each GPCR used for screening in the cell.

Methods using one cell to screen a test composition for non-receptor-specific GPCR desensitization inhibitory activity involve using at least a first GPCR and a second GPCR that is different than the first GPCR. Each cell also includes a first conjugate of a marker molecule and a protein associated with the desensitization pathway of the first GPCR and a second conjugate of a marker molecule and a protein associated with the desensitization pathway of the second GPCR. The marker molecules and/or the proteins associated with the desensitization pathways may be the same or different in the first and second conjugates. When both the marker molecule and the protein associated with the desensitization pathway are the same in the first and second conjugates, it is possible to use only one type of conjugate in the cell. It should be noted, however, that other embodiments could use multiple conjugates containing different marker molecules and/or proteins associated with the desensitization pathways of different GPCRs that are being used to screen a test composition. In such embodiments, different conjugates could be used to indicate desensitization inhibitory activity of a composition with respect to different GPCRs being used to screen a test composition. Also in such embodiments, multiple conjugates could be used (in combination or separately) to indicate GPCR desensitization inhibitory activity of a composition with respect to the same GPCR. In methods using one cell, an indication of non-receptor-specific GPCR desensitization inhibitory activity is shown with respect to a test composition when there is an indication that the test composition has GPCR desensitization inhibitory activity with respect to each of the two or more GPCRs in the cell.

When two or more cells are used to screen a test composition for non-receptor-specific GPCR desensitization inhibitory activity, each cell expresses at least one GPCR that is different from the GPCR or GPCRs being used to screen the test composition in the other cell or cells. Each cell also includes one or more conjugates comprising a marker molecule and a protein associated with the GPCR desensitization pathway of one or more of the GPCRs expressed in the cell being used to screen a test composition. The conjugates may be the same or different in each of the two or more cells. As stated above, the conjugate or conjugates indicate, through the use of the marker molecule, GPCR desensitization inhibitory activity of a test composition.

Methods using two (or more) cells involve using a first cell having a first GPCR and a second cell having a second GPCR that is different from the first GPCR. The first cell includes a first conjugate of a protein associated with the GPCR desensitization pathway of the first GPCR (e.g., an arrestin protein, the first GPCR, etc.) and a marker molecule, and the second cell includes a second conjugate of a protein associated with the GPCR desensitization pathway of the second GPCR and a marker molecule. The second conjugate may be the same or different from the first conjugate. That is, the protein associated with the GPCR desensitization pathway may be the same or different in the first conjugate and the second conjugate. The marker molecule may also be the same or different in the first conjugate and the second conjugate. In addition, more than one conjugate may be included in each cell and more than one GPCR may be expressed in each cell to be used to screen a test composition. In methods using two or more cells (where each cell has one or more GPCRs that are different from the GPCR(s) in the other cell or cells), an indication of non-receptor-specific GPCR desensitization inhibitory activity is shown with respect to a test composition when there is an indication that the test composition has GPCR desensitization inhibitory activity with respect to each of the two or more different GPCRs.

As discussed above, an indication that a test composition has non-receptor-specific GPCR desensitization inhibitory activity is shown when there is an indication that the particular test composition has GPCR desensitization inhibitory activity with respect to each of the two or more GPCRs that are different from one another being used to screen the test composition. The indication of non-receptor-specific GPCR desensitization inhibitory activity may be shown with respect to two or more GPCRs that are different from one another that are expressed in one or more cells. In order to determine whether there is an indication that a test composition has non-receptor-specific GPCR desensitization inhibitory activity, the test composition is screened for GPCR desensitization inhibitory activity with respect to each of the two or more GPCRs being used in a specific embodiment.

In order to screen a test composition for GPCR desensitization inhibitory activity in a cell with respect to at least one specific GPCR, the cell expressing the GPCR is placed or held under conditions necessary for GPCR desensitization to occur of at least that specific GPCR and the cell is also exposed to the test composition. The conditions necessary for GPCR desensitization to occur in a cell may vary from cell to cell and from GPCR to GPCR. For example, desensitization of some GPCRs is agonist-dependent, while desensitization of some modified GPCRs (described more fully below) occurs constitutively in an agonist-independent manner. In addition, those GPCRs in which desensitization occurs in an agonist-dependent manner may require different agonists for desensitization depending upon the particular GPCR.

When the GPCR that is being used to screen for GPCR desensitization activity of a test composition is a GPCR that requires agonist for desensitization, the cell expressing the GPCR is exposed to a test composition and to an agonist for the GPCR, either simultaneously or serially in any order. When exposing a cell to a test composition and to an agonist serially, the sequence and the timing in between exposure to the test composition and to the agonist will depend upon the specific embodiment of the present invention being used. A detection method is used to detect for an indication of GPCR desensitization inhibitory activity of the test composition. If the GPCR used to screen for GPCR desensitization activity of a test composition is a modified GPCR that does not require agonist for GPCR desensitization, the cell expressing the GPCR is exposed to a test composition and a suitable detection method is used to detect for an indication of GPCR desensitization inhibitory activity of the test composition. Detection methods useful in the present invention are explained more fully below.

In embodiments using one cell expressing two or more different GPCRs, various formats could be used for screening a composition for non-receptor-specific GPCR desensitization activity. In such embodiments, the methods will generally comprise exposing the cell to a test composition, to an agonist for the first GPCR (when the first GPCR requires agonist for desensitization), and to an agonist for the second GPCR (when the second GPCR requires agonist for desensitization) and determining whether or not the composition has GPCR desensitization inhibitory activity with respect to the first GPCR and with respect to the second GPCR. The specific order of exposing the cell to the test composition and one or more agonists (when needed) may vary based upon various factors such as the desensitization pathway of each GPCR and the conjugate or conjugates used in the cell. In addition, measures may be taken such that indications of GPCR desensitization inhibitory activity with respect to different GPCRs in the cell may be distinguished. For example, a time separation could be used between the screening of a test composition with respect to different GPCRs (e.g., between screening with respect to a first GPCR and screening with respect to a second GPCR) such that indications of GPCR desensitization inhibitory activity of a composition with respect to the different GPCRs may be distinguished. As another example, separate conjugates could be used for the screening of a test composition with respect to each GPCR used in the cell such that each conjugate is included only in the desensitization pathway of one of the GPCRs and such that each conjugate contains different marker molecules that are distinguishable from each other upon detection.

In some embodiments of methods for screening for non-receptor-specific GPCR desensitization inhibitory activity of a test composition using one cell, two or more different GPCRs that require agonist for desensitization or are constitutively desensitized could be used. In general, such methods will comprise exposing the cell to a test composition, to an agonist for the first GPCR (when the first GPCR requires agonist for desensitization), and to an agonist for the second GPCR (when the second GPCR requires agonist for desensitization) and then determining whether or not the composition has GPCR desensitization inhibitory activity with respect to the first GPCR and with respect to the second GPCR. In such embodiments, an indication of GPCR desensitization inhibitory activity with respect to the first GPCR and an indication of GPCR desensitization inhibitory activity with respect to the second GPCR may be distinguished by using a different conjugate for the determination of GPCR desensitization inhibitory activity of the compositions with respect to the different GPCRs. That is, conjugates may be chosen such that the protein of the first conjugate is not included in the desensitization pathway of the second GPCR, the protein of the second conjugate is not included in the desensitization pathway of the first GPCR, and the first and second conjugates contain different marker molecules that are distinguishable from each other upon detection. As an example, a cell could include a first conjugate comprising a first GPCR and a first marker molecule and a second conjugate comprising a second GPCR and a second marker molecule that is different and distinguishable from the first marker molecule. In such an embodiment, it may be possible to expose the cell to the test composition, the agonist for the first GPCR (if needed for desensitization), and the agonist for the second GPCR (if needed for desensitization) simultaneously or non-simultaneously and determine whether the composition has GPCR desensitization inhibitory activity with respect to the first GPCR and the second GPCR.

In other embodiments of methods for screening for non-receptor-specific GPCR desensitization inhibitory activity of a test composition using one cell with two or more GPCRs requiring an agonist for desensitization, a time separation may be used between screening each of the GPCRs in the cell. For example, a cell comprising a first GPCR and a second GPCR could be exposed to an agonist for the first GPCR and then, after a sufficient amount of time, the cell could be exposed to an agonist for the second GPCR such that indications of desensitization inhibitory activity with respect to the first and second GPCRs may be sufficiently distinguished. In such an embodiment, the cell could be exposed to the test composition at various times before, after, or during exposure to the agonist for the first GPCR and the cell could be re-exposed to the test composition before, during, or after exposure to the agonist for the second GPCR. In addition, in such an embodiment, the GPCRs could be chosen such that the agonist for the first GPCR is not an agonist for the second GPCR and the agonist for the second GPCR is not an agonist for the first GPCR such that indications of desensitization inhibitory activity of the test compound could be distinguished with respect to the first GPCR and the second GPCR.

As mentioned above, the marker molecule(s) of the conjugate(s) in each cell is/are used to provide an indication of whether a test composition has GPCR desensitization inhibitory activity in that particular cell with respect to the GPCR or GPCRs being used in that cell to screen the test composition. Based upon the GPCR desensitization pathway, various formats of detection methods may be used as an indication that a test composition has GPCR desensitization inhibitory activity. The format that is used will depend somewhat on the particular protein associated with the desensitization pathway to which the marker molecule is conjugated.

For example, by referring to and describing FIG. 1 (which illustrates an example of a desensitization pathway of a GPCR in response to an agonist), formats of detection methods using conjugates of an arrestin protein and a marker molecule and/or a GPCR and a marker molecule will be better understood. With reference to FIG. 1, after an agonist 10 interacts with a GPCR 2 to activate the GPCR 2 (shown by arrow A), one or more GRKs 15 phosphorylate clusters of serine and threonine residues located in the third intracellular loop 11 or the carboxyl-terminal tail 3 of the GPCR 2 (shown by arrow B). After phosphorylation, an arrestin protein 6 associates with the GRK-phosphorylated GPCR 2 and uncouples the GPCR 2 from its cognate G protein 20 to terminate GPCR signaling and produce a desensitized GPCR. Translocation of the arrestin 6 to the GPCR 2 is shown by arrow C. After the arrestin 6 binds to the GPCR 2, the arrestin/GPCR complex 7 targets to clathrin-coated pits or vesicles 8 (shown by arrow D) for endocytosis. Internalization of the GPCR 2 alone or the arrestin/GPCR complex 7 into endosomes 9 is shown by arrow E. Arrow E' shows internalization of the GPCR 2 into an endosome 9. Arrow E' shows internalization of the arrestin/GPCR complex 7 into an endosome 9. After or during internalization, the GPCR 2 is dephosphorylated and is recycled back to the cell membrane 1 as a resensitized GPCR 2. Recycling of the GPCR 2 that was internalized alone is shown by arrow F'. Recycling of the GPCR 2 that was internalized as the arrestin/GPCR complex 7 is shown by arrow F".

With reference to FIG. 1, when a conjugate of an arrestin protein and a marker molecule is used in a cell, the detection method could detect for any of the following, the lack of which would be an indication that the test composition has GPCR desensitization inhibitory activity: (1) translocation of the arrestin conjugate 6 from the cytosol 5 to the cell membrane 1 (i.e., arrow C); (2) localization of the arrestin conjugate 6 at the plasma membrane 1; (3) translocation of the arrestin conjugate 6 from the cell membrane 1 to clathrin coated pits/vesicles 8, endosomes 9, or the cytosol 5 (i.e., arrows D and E); or (4) localization of the arrestin conjugate 6 at clathrin coated pits/vesicles 8, endosomes 9, or the cytosol 5. As another example, when a conjugate of a GPCR and a marker molecule is used in a cell, the detection method could look for any of the following, the lack of which would be an indication that the test composition has GPCR desensitization inhibitory activity: (1) translocation of the GPCR conjugate 2 from the cell membrane 1 to clathrin coated pits/vesicles 8, endosomes 9, or the cytosol 5 (i.e., arrows D and E); or (2) localization of the GPCR conjugate 2 at clathrin coated pits/vesicles 8, endosomes 9, or the cytosol 5. As yet another example, when both a conjugate of an arrestin protein and a marker molecule and a conjugate of a GPCR and a marker molecule are used in a cell, the detection method could look for any of the items/events listed above as well as for localization of the arrestin conjugate with the GPCR conjugate, the lack of which would be an indication that the test composition has GPCR desensitization inhibitory activity. Although the formats of detection methods above are described with respect to FIG. 1, which includes addition of an agonist for GPCR desensitization, these formats are not meant to be limited to the use of an agonist, and also apply to other embodiments such as, for example, embodiments using one or more GPCRs that are constitutively desensitized.

Detection for each of the items/events discussed above could be conducted at one point in time, over a period of time, at two or more points in time for comparison (e.g., before and after exposure to a test composition), etc. An indication of GPCR desensitization inhibitory activity could be determined by detecting for one or more of the items/events discussed above in a cell exposed to the test composition and comparing the results to those obtained by detecting for the same item(s)/event(s) in a control cell, by comparing the results to a predetermined value, or without reference to a predetermined level or a control cell. Therefore, in addition to using a lack of certain items/events as indications of GPCR desensitization inhibitory activity, a decrease in the level of any of the same items/events discussed above after exposure to a test composition could be used as an indication of GPCR desensitization activity of the test composition. Detecting for a decrease in the level of the items/events discussed above (e.g., as compared to a control cell not being exposed to the test composition, as compared to a predetermined level, or as compared to a level before exposure to the test composition) may be useful in embodiments where a test composition is added when desensitization is already occurring such as, for example, in embodiments using a cell expressing a constitutively desensitized GPCR or in embodiments where a test composition is added after the cell has been exposed to an agonist.

G-Protein Coupled Receptors (GPCRs)

Any G-protein coupled receptor (GPCR) may be used in the methods of the present invention that is capable of participating in the GPCR desensitization pathway such that GPCR desensitization inhibitory activity of a test composition may be determined. An illustrative, non-limiting list of known GPCRs with which the present invention may be used is contained in FIG. 2. The receptors are grouped according to classical divisions based on structural similarities and ligands. GPCRs that may be used in the present invention include known GPCRs, unknown or orphan GPCRs, and chimeric or modified GPCRs (described more fully below). Modified GPCRs include GPCRs that have one or more modifications in the carboxyl-terminal tail, modifications in the intracellular loop(s), and/or in the cytoplasmic end of the transmembrane region.

By way of example, three major classes of GPCRs for known receptors have been identified: Class A receptors, Class B receptors, and receptors with virtually non-existent carboxyl-terminal tails. The receptors are classified accordingly based on their interactions with an affinity for rat β-arrestin-2 in HEK-293 cells and may be predicted based on the amino acid residues in their carboxyl-terminal tail and the length of their carboxyl-terminal tail. A Class B receptor is a GPCR that has one or more sites of phosphorylation (e.g., clusters of phosphorylation sites) properly positioned in its carboxyl-terminal tail such that it does recruit rat β-arrestin-2 to endosomes in HEK-293 cells under conditions as described in U.S. Pat. No. 5,891,646, Oakley, et al. "Differential Affinities of Visual Arrestin, βArrestin1, and βArrestin2 for G Protein-coupled Receptors Delineate Two Major Classes of Receptors," *Journal of Biological Chemistry*, Vol 275, No. 22, pp 17201–17210, Jun. 2, 2000, and Oakley et al., "Molecular Determinants Underlying the Formation of Stable Intracellular G Protein-coupled Receptor-β-Arrestin Complexes after Receptor Endocytosis," *Journal of Biological Chemistry*, Vol. 276, No. 22, pp 19452–19460, 2001, the contents of which are hereby incorporated by reference in their entirety. A Class A receptor is a GPCR that does not have one or more sites of phosphorylation (e.g., clusters of phosphorylation sites) properly positioned in its carboxyl-terminal tail such that it does not recruit rat β-arrestin-2 to endosomes in HEK-293 cells under conditions as described above for Class B receptors. Receptors with virtually non-existent carboxyl-terminal tails include, for example, olfactory and taste receptors.

FIG. 3 is an illustrative, non-limiting list of known receptors, including the amino acid sequence for their carboxyl terminal tails and appropriate classification. For the Class B receptor examples, the residues that may function as clusters of phosphorylation sites are shown in bolded italics.

After agonists bind and activate GPCRs, G protein-coupled receptor kinases (GRKs) phosphorylate clusters of serine and threonine residues located in the third intracellular loop or the carboxyl-terminal tail of the GPCRs. After phosphorylation, an arrestin protein associates with the GRK-phosphorylated receptor and uncouples the receptor from its cognate G protein. The interaction of the arrestin with the phosphorylated GPCR terminates GPCR signaling and produces a non-signaling, desensitized receptor.

The arrestin bound to the desensitized GPCR targets the GPCR to clathrin-coated pits for endocytosis by functioning as an adaptor protein, which links the GPCR to components of the endocytic machinery, such as adaptor protein-2 (AP-2) and clathrin. The internalized GPCRs are dephosphorylated and are recycled back to the cell surface resensitized.

The stability of the interaction of arrestin with the GPCR dictates the rate of GPCR dephosphorylation, recycling, and resensitization. When the GPCR has an enhanced affinity for arrestin, the GPCR/arrestin complex is stable, remains intact and is internalized into endosomes. When the GPCR does not have an enhanced affinity for arrestin, the GPCR/arrestin complex tends not to be stable and arrestin is not recruited into endosomes with the GPCR. When the GPCR has an enhanced affinity for arrestin, the GPCR/arrestin complex remains intact, and the GPCR dephosphorylates, recycles and resensitizes slowly. In contrast, GPCRs that dissociate from arrestin at or near the plasma membrane dephosphorylate and recycle rapidly.

The ability of the arrestin to remain associated with the GPCRs is mediated by one or more sites of phosphorylation (e.g., clusters of phosphorylation sites) properly positioned within the carboxyl-terminal tail. These clusters of phosphorylation sites are may be serine and threonine residues located in the carboxyl-terminal tail of the GPCR. These clusters are remarkably conserved in their position within the carboxyl-terminal tail domain and serve as primary sites of agonist-dependent phosphorylation.

Modified GPCRs

1. Constitutively Desensitized GPCRs

The modified GPCRs of the present invention include GPCRs comprising a modified DRY motif as described in U.S. patent application Ser. No. 10/054,616, filed Jan. 22, 2002, the content of which is hereby incorporated by reference herein in its entirety. A DRY motif is a highly conserved GPCR motif located near the cytoplasmic boundary of the third transmembrane region and the second intracellular loop. The DRY motif is typically a three amino acid motif: Aspartate-Arginine-Tyrosine (DRY). A modified DRY motif refers to a DRY motif of a GPCR that has one or modifications resulting in an amino acid sequence other than the DRY motif. In one embodiment, the modified DRY motif consists of an amino acid other than arginine as the second amino acid. The second amino acid of the modified DRY motif is typically Alanine, Aspartate, Glutamate, Histidine, or Asparagine, but may be any amino acid other than arginine or Lysine. This modified DRY motif results in a constitutively desensitized GPCR. As described herein, the DRY motif of any GPCR can be modified as described, resulting in a constitutively desensitized GPCR. This modification may allow the modified GPCR to bind arrestin in the absence of agonist.

A wild-type GPCR cycles between being (1) sensitized, which means presently able to respond to agonist and activate conventional G protein signaling, (2) desensitized, which means presently unable to respond to agonist and activate conventional G protein signaling, and (3) resensitized, which means again presently able to respond to agonist and activate conventional G protein signaling. This balance can be disrupted, resulting, for example, in a constitutively desensitized GPCR. A constitutively desensitized GPCR does not cycle as above. Under wild-type conditions, a GPCR is desensitized subsequent to agonist activation of the sensitized GPCR; whereas, a constitutively desensitized GPCR forms independent of agonist stimulation of the sensitized GPCR. In a particular embodiment, the modified GPCRs of the present invention include GPCRs that have been modified so that they localize to endocytic vesicles or endosomes in an agonist-independent manner.

In a constitutively desensitized GPCR, the equilibrium between having the ability, versus inability, to properly activate conventional G protein signaling is shifted toward the inability to properly activate conventional G protein signaling. Additionally, the constitutively desensitized GPCRs of the present invention are constitutively phosphorylated, constitutively bind arrestin, constitutively localize in clathrin-coated pits, and/or constitutively localize to endocytic vesicles or endosomes. Constitutively desensitized receptors lack ability to properly respond to agonist and may be desensitized even in the absence of agonist. Constitutively desensitized GPCRs form independent of agonist stimulation of the sensitized GPCR. Constitutively desensitized GPCRs may include a host of degrees of inappropriate signaling and a constitutively desensitized receptor may or may not signal at some point during its lifetime.

The modified GPCRs of the present invention may comprise one or more modifications in the DRY motif. The DRY motif may be modified in one or more of the three amino acids, but must be modified at least in the second position (i.e., Arginine). The DRY motif may be modified in whole or in part. Modifications of this motif can form a constitutively desensitized receptor.

By way of example, the V2R has a DRY motif at amino acids 136–138. Modifications of the DRY motif may promote agonist-independent formation of a GPCR/arrestin complex and constitutive localization to the endocytic vesicles or endosomes. The $\alpha_{1B}$-AR receptor comprises a DRY motif at amino acids 142–144 that promotes formation of a GPCR/arrestin complex and localizes to endocytic vesicles or endosomes. The $AT_{1A}R$ receptor comprises a DRY motif at amino acids 125–127 that also promotes formation of a GPCR/arrestin complex and localizes to the endocytic vesicles or endosomes. FIG. 4 illustrates the amino acid sequences of the following GPCRs in which the DRY motif has been modified: V2R, $\alpha_{1B}$-AR, and $AT_{1A}R$.

The modified GPCRs of the present invention include GPCRs that have been modified in the DRY motif to localize to endocytic vesicles or endosomes in an agonist-independent manner. The polypeptide sequences of the modified GPCRs of the present invention include sequences having one or more additions, deletions, substitutions, or mutations. These mutations may be substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention should be considered to include sequences containing conservative changes that do not significantly alter the activity or binding characteristics of the resulting protein. The present invention should also be considered to include sequences containing non-conservative changes that do not significantly alter the activity or binding characteristics of the resulting protein.

To create a modified GPCR containing a modified DRY motif according to the present invention, a GPCR comprising a DRY motif may have one or more additions, substitutions, deletions, or mutations of amino acid residues in its DRY motif such that the modified GPCR is a constitutively desensitized receptor. By way of example, discrete point mutations of the amino acid residues may be made to provide a modified GPCR. By way of example, three consecutive amino acids may be mutated to provide a modified GPCR. By way of example, the Arginine may be mutated to any amino acid other than Lysine such as, for example, Alanine, Glutamate, Aspartate, Asparagine, or Histidine, to provide a modified GPCR.

In addition, to create a modified GPCR containing a modified DRY motif, mutations may be made in a nucleic acid sequence of a GPCR such that a particular codon is changed to a codon that codes for a different amino acid. Such a mutation is generally made by making the fewest nucleotide changes possible. A substitution mutation of this sort can be made to change an amino acid in the resulting protein to create a modified DRY motif forming a constitutively desensitized receptor. Also by way of example, discrete point mutations of the nucleic acid sequence may be made.

Furthermore, to provide modified GPCRs of the present invention, a GPCR that binds arrestin in an agonist-dependent manner may also have its DRY motif, in whole or in part, exchanged with that of a GPCR having a modified DRY motif that forms a constitutively desensitized receptor. For example, the DRY motif of a GPCR that binds arrestin in an agonist-dependent manner may be exchanged at an amino acid residue in close proximity to the DRY motif.

Modified GPCRs may be generated by molecular biological techniques standard in the genetic engineering art, including but not limited to, polymerase chain reaction (PCR), restriction enzymes, expression vectors, plasmids, and the like. By way of example, vectors may be designed to enhance the agonist-independent affinity of a GPCR for arrestin. PCR amplified DNA fragments of a GPCR to be modified may be digested by appropriate restriction enzymes and subcloned into the vector, such as pcDNA3.1/zeo or pEGFP-N3. Modifications of the DNA may be introduced by standard molecular biological techniques as described above.

As may be shown by standard receptor binding assays, the modified GPCRs are essentially indistinguishable from their wild-type counterparts except for an agonist-independent affinity for arrestin, and thus, constitutive endosomal localization. For example, the modified GPCRs possess similar affinity for antagonists or inverse agonists, and the like.

By way of example, V2R may have a modification R137H (FIG. 3) resulting in modified endocytic targeting. The modified DRY motif of the V2R R137H can be used to replace the DRY motif of other GPCRs. This three amino acid sequence may be located near the cytoplasmic boundary of the third transmembrane region and the second intracellular loop. Modified GPCRs containing a mutation of the R of the DRY motif have an increased affinity for arrestin and colocalize with arrestin in endocytic vesicles or endosomes in an agonist-independent manner.

2. GPCRs with Increased Phosphorylation Sites

GPCRs that do not naturally recruit arrestin to endosomes or do not even naturally recruit arrestin to the plasma membrane may be modified to comprise one or more sites of phosphorylation (e.g., clusters of phosphorylation sites) properly positioned in their carboxyl-terminal tail or properly positioned at other positions in the amino acid sequence (e.g., in the third intracellular loop). This modification allows the modified GPCR to form a stable complex with an arrestin that will internalize into endosomes.

The modified GPCRs of the present invention include GPCRs comprising one or more modifications in their carboxyl-terminal tail. These modifications may comprise inserting one or more sites of phosphorylation (e.g., clusters of phosphorylation sites) within certain regions of the carboxyl-terminal tail, as described in U.S. patent application Ser. No. 09/993,844, filed Nov. 5, 2001, the content of which is hereby incorporated by reference herein in its entirety. As such, the carboxyl-terminal tail may be modified in whole or in part. The carboxyl-terminal tail of many GPCRs begins shortly after a conserved NPXXY motif that marks the end of the seventh transmembrane domain (i.e. what follows the NPXXY motif is the carboxyl-terminal tail of the GPCR). The carboxyl-terminal tail of many GPCRs comprises a putative site of palmitoylation approximately 10 to 25 amino acid residues (e.g., 15 to 20 amino acid residues) downstream of the NPXXY motif. This site is typically one or more cysteine residues. The carboxyl-terminal tail of a GPCR may be relatively long, relatively short, or virtually non-existent. The carboxyl-terminal tail of a GPCR determines the affinity of arrestin binding.

Specific amino acid motifs in the carboxyl-terminal tail promote formation of a stable GPCR/arrestin complex and thus ultimately may promote recruitment of arrestin to endosomes. These amino acid motifs comprise one or more amino acids (e.g., clusters of phosphorylation sites) that may be efficiently phosphorylated and thus readily function as phosphorylation sites. The clusters of amino acids may occupy two out of two, two out of three, three out of three, three out of four positions, four out of four, four out of five positions, five out of five, and the like consecutive amino acid positions. Accordingly, the clusters of amino acids that promote formation of a stable GPCR/arrestin complex are "clusters of phosphorylation sites." These clusters of phosphorylation sites may be clusters of serine and threonine residues.

GPCRs that form stable complexes with arrestin comprise one or more sites of phosphorylation (e.g., clusters of phosphorylation sites). In addition to the presence of the one or more sites of phosphorylation (e.g., clusters of phosphorylation sites) the sites must be properly positioned within the carboxyl-terminal tail to promote formation of a stable GPCR/arrestin complex. To promote formation of a stable GPCR/arrestin complex, the one or more sites of phosphorylation (e.g., one or more clusters of phosphorylation) may be approximately 15 to 35 (e.g., 15 to 25) amino acid residues downstream of a putative site of palmitoylation of the GPCR. In addition, the one or more sites of phosphorylation (e.g., one or more clusters of phosphorylation, may be approximately 20 to 55 (e.g., 30 to 45) amino acid residues downstream of the NPXXY motif of the GPCR. GPCRs containing one or more sites of phosphorylation (e.g., clusters of phosphorylation sites) properly positioned are typically Class B receptors.

By way of example, it has been discovered that the V2R receptor comprises a cluster of phosphorylation sites (SSS) that promotes formation of a stable GPCR/arrestin complex at 19 amino acid residues downstream of the putative site of palmitoylation and 36 amino acid residues downstream of the NPXXY motif. The NTR-2 receptor comprises a cluster of phosphorylation sites (STS) that promotes formation of a stable GPCR/arrestin complex at 26 amino acid residues downstream of the putative site of palmitoylation and 45 amino acid residues downstream of the NPXXY motif. The oxytocin receptor (OTR) receptor comprises two clusters of phosphorylation sites (SSLST and STLS) that promote formation of a stable GPCR/arrestin complex, one at 20 amino acid residues downstream of the putative site of palmitoylation and 38 amino acid residues downstream of the NPXXY motif, and the other at 29 amino acid residues downstream of the putative site of palmitoylation and 47 amino acid residues downstream of the NPXXY motif. The substance P receptor (SPR, also known as the neurokinin-1 receptor) comprises a cluster of phosphorylation sites (TTIST) that promotes formation of a stable GPCR/arrestin complex at 32 amino acid residues downstream of the putative site of palmitoylation and 50 amino acid residues downstream of the NPXXY motif.

GPCRs that lack one or more sites of phosphorylation (e.g., clusters of phosphorylation sites) properly positioned within the carboxyl terminal tail form GPCR/arrestin complexes that are less stable and dissociate at or near the plasma membrane. These GPCRs are typically Class A receptors, olfactory receptors, taste receptors, and the like. However, stable GPCR/arrestin complexes may be achieved with GPCRs naturally lacking one or more sites of phosphorylation and having a lower affinity for arrestin by modifying the carboxyl-terminal tails of these receptors. The carboxyl-terminal tails may be modified to include one or more sites of phosphorylation (e.g., one or more clusters of phosphorylation sites) properly positioned within the carboxyl terminal tail.

The modified GPCRs of the present invention include GPCRs that have been modified to have one or more sites of phosphorylation (e.g., one or more clusters of phosphorylation) properly positioned in their carboxyl terminal tails. The polypeptide sequences of the modified GPCRs of the present invention also include sequences having one or more additions, deletions, substitutions, or mutations. These mutations may be substitution mutations made in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The present invention should be considered to include sequences containing conservative changes that do not significantly alter the activity or binding characteristics of the resulting protein.

The modified GPCRs of the present invention include GPCRs containing a NPXXY motif, a putative site of palmitoylation approximately 10 to 25 amino acid residues (e.g., 15 to 20 amino acids) downstream of the NPXXY motif, and a modified carboxyl-terminal tail. The modified carboxyl-terminal tail has one or more sites of phosphorylation (e.g., one or more clusters of phosphorylation sites) such that the phosphorylation sites are approximately 15 to 35 (e.g., 15 to 25) amino acid residues downstream of the putative site of palmitoylation of the modified GPCR. The modified carboxyl-terminal tail may have one or more sites of phosphorylation (e.g., one or more clusters of phosphorylation sites) such that the phosphorylation sites are approximately 20 to 55 (e.g., 30 to 45) amino acid residues downstream of the NPXXY of the modified GPCR.

To create a modified GPCR containing a modified carboxyl-terminus region according to the present invention, a GPCR lacking phosphorylation sites or clusters of phosphorylation sites or with a lower or unknown affinity for arrestin may have one or more additions, substitutions, deletions, or mutations of amino acid residues in its carboxyl-terminal tail. These additions, substitutions, deletions, or mutations are performed such that the carboxyl-terminal tail is modified to comprise one or more sites of phosphorylation (e.g., clusters of phosphorylation sites). By way of example, discrete point mutations of the amino acid residues may be made to provide a modified GPCR. By way of example, three consecutive amino acids may be mutated to serine residues to provide a modified GPCR. These mutations are made such that the one or more sites of phosphorylation (e.g., clusters of phosphorylation sites) are properly positioned within the carboxyl terminal tail.

In addition, to create a modified GPCR containing a modified carboxyl-terminal tail region, mutations may be made in a nucleic acid sequence of a GPCR lacking sites of phosphorylation or clusters of phosphorylation sites or with a lower or unknown affinity for arrestin such that a particular codon is changed to a codon that codes for a different amino acid (e.g., a serine or threonine). Such a mutation is generally made by making the fewest nucleotide changes possible. A substitution mutation of this sort can be made to change an amino acid in the resulting protein to create one or more sites of phosphorylation (e.g., clusters of phosphorylation sites). Also by way of example, discrete point mutations of the nucleic acid sequence may be made. The phosphorylation sites are positioned such that they are located approximately 15 to 35 amino acid residues downstream of the putative site of palmitoylation of the modified GPCR.

Furthermore, to provide modified GPCRs of the present invention, a GPCR lacking properly positioned phosphorylation sites or with a lower or unknown affinity for arrestin may also have its carboxyl-terminal tail, in whole or in part, exchanged with that of a GPCR having properly positioned clusters of phosphorylation sites. The site of exchange may be after or including the conserved NPXXY motif. As an alternative, a putative site of palmitoylation of a GPCR may be identified at approximately 10 to 25 (e.g., 15 to 20) amino acid residues downstream of the conserved NPXXY motif, and the site of exchange may be after or including the palmitoylated cysteine(s). As discussed below, if a putative site of palmitoylation does not exist, one may be introduced in the GPCR. The carboxyl-terminal tail of a GPCR lacking properly positioned clusters of phosphorylation sites or with a lower or unknown affinity for arrestin may be exchanged at an amino acid residue in close proximity to a putative site of palmitoylation. In one embodiment, the carboxyl-terminal tail of a GPCR lacking properly positioned clusters of phosphorylation sites or with a lower or unknown affinity for arrestin is exchanged at a putative site of palmitoylation approximately 10 to 25 (e.g., 15 to 20) amino acid residues downstream of the NPXXY motif, such that the palmitoylated cysteine residue is maintained. The carboxyl-terminal tail of a GPCR lacking properly positioned clusters of phosphorylation sites may be exchanged in a manner allowing the clusters of phosphorylation sites to be properly positioned within the carboxyl-terminal tail of the modified GPCR. The tails may be exchanged and the modified GPCRs may be constructed accordingly by manipulation of the nucleic acid sequence or the corresponding amino acid sequence.

In a further alternative, the carboxyl-tail of a GPCR, for example a GPCR not containing the NPXXY motif, may be predicted from a hydrophobicity plot and the site of exchange may be selected accordingly. Based on a hydrophobicity plot, one of skill in the art may predict a site where it is expected that the GPCR may anchor in the membrane and then predict where to introduce a putative site of palmitoylation accordingly. Using this technique GPCRs having neither a NPXXY motif nor a putative site of palmitoylation may be modified to create a point of reference (e.g. a putative site of palmitoylation). The introduced putative site of palmitoylation may then be used to position a tail exchange.

The carboxyl-terminal tail used for the exchange may be from a second GPCR having one or more properly positioned clusters of phosphorylation sites and having a putative site of palmitoylation approximately 10 to 25 (e.g., 15 to 20) amino acid residues downstream of a NPXXY motif. The tail as identified may be exchanged, after or including the conserved NPXXY motif. As an alternative, a putative site of palmitoylation of a GPCR may be identified at approximately 10 to 25 (e.g., 15 to 20) amino acid residues downstream of the conserved NPXXY motif, and the tail may be exchanged after or including the palmitoylated cysteine(s). The carboxyl-terminal tail of a GPCR having clusters of phosphorylation sites may be exchanged at an amino acid residue in close proximity to a putative site of palmitoylation. In one embodiment, the carboxyl-terminal tail of a GPCR having clusters of phosphorylation sites is exchanged at a putative site of palmitoylation approximately 10 to 25 (e.g., 15 to 20) amino acid residues downstream of the NPXXY motif, such that the portion of the carboxyl-terminal tail containing the clusters of phosphorylation sites begins at the amino acid residue immediately downstream of the palmitoylated cysteine residue. The carboxyl-terminal tail having clusters of phosphorylation sites used for the exchange may have a marker molecule conjugated to the carboxyl-terminus. The tails may be exchanged and the modified GPCRs may be constructed accordingly by manipulation of the nucleic acid sequence or the corresponding amino acid sequence.

In addition, the carboxyl-terminal tail portion used for the exchange may originate from a polypeptide synthesized to have an amino acid sequence corresponding to an amino acid sequence from a GPCR having one or more sites of phosphorylation (e.g., one or more clusters of phosphorylation sites). The synthesized polypeptide may have a putative site of palmitoylation approximately 10 to 25 (e.g., 15 to 20) amino acid residues downstream of a NPXXY motif. The synthesized polypeptide may have one or more additions, substitutions, mutations, or deletions of amino acid residues that does not affect or alter the overall structure and function of the polypeptide.

Furthermore, the carboxyl-terminal tail portion used for the exchange may originate from a naturally occurring polypeptide recognized to have an amino acid sequence corresponding to an amino acid sequence from a GPCR having one or more clusters of phosphorylation sites. The polypeptide may have a putative site of palmitoylation approximately 10 to 25 (e.g., 15 to 20) amino acid residues downstream of a NPXXY motif. The polypeptide may have one or more additions, substitutions, mutations, or deletions of amino acid residues that does not affect or alter the overall structure and function of the polypeptide.

A modified GPCR containing a modified carboxyl-terminus region may be created by fusing a first carboxyl-terminal tail portion of a GPCR lacking properly positioned clusters of phosphorylation sites or with a lower or unknown affinity for arrestin with a second carboxyl-terminal tail portion of a GPCR or polypeptide having one or more clusters of phosphorylation sites. The second GPCR or polypeptide used for the exchange may have a putative site of palmitoylation approximately 10 to 25 (e.g., 15 to 20) amino acid residues downstream of a NPXXY motif. Accordingly, the modified carboxyl-terminus region of the modified GPCR comprises a portion of a carboxyl-terminal tail from a GPCR lacking properly positioned clusters of phosphorylation sites or with a lower or unknown affinity for arrestin fused to a portion of a carboxyl-terminal tail of a GPCR or polypeptide having clusters of phosphorylation sites. The tail of a GPCR lacking properly positioned clusters of phosphorylation sites may be exchanged after or including the conserved NPXXY motif, and fused to a carboxyl-terminal tail containing clusters of phosphorylation sites, after or including the conserved NPXXY motif. As an alternative, the tail of a GPCR lacking properly positioned clusters of phosphorylation sites may be exchanged after or including the palmitoylated cysteine(s), and fused to a tail containing clusters of phosphorylation sites, after or including the palmitoylated cysteine(s). The tails may be exchanged and the modified GPCRs may be constructed accordingly by manipulation of the nucleic acid sequence or the corresponding amino acid sequence.

In a further alternative, the carboxyl-tail of a GPCR, for example a GPCR not containing the NPXXY motif, may be predicted from a hydrophobicity plot and exchanged accordingly. The site of exchange may be selected according to the hydrophobicity plot. Based on a hydrophobicity plot, one of skill in the art may predict a site where it is expected that the GPCR may anchor in the membrane and then predict where to introduce a putative site of palmitoylation accordingly. Using this technique GPCRs having neither a NPXXY motif nor a putative site of palmitoylation may be modified to create a point of reference (e.g. a putative site of palmitoylation). The introduced putative site of palmitoylation may be then used to position a tail exchange. After introduction of a putative site of palmitoylation, the resulting tail may be fused with a second carboxyl-terminal tail portion of a GPCR or polypeptide having one or more clusters of phosphorylation sites and having a putative site of palmitoylation approximately 10 to 25 (e.g., 15 to 20) amino acid residues downstream of a NPXXY motif.

The modified carboxyl-terminus region of the modified GPCR may be fused at amino acid residues in close proximity to a putative site of palmitoylation. In one embodiment, the modified carboxyl-terminus region of the modified GPCR is fused such that the portion from the first GPCR with a lower affinity for arrestin comprises amino acid residues from the NPXXY motif through a putative site of palmitoylation approximately 10 to 25 (e.g., 15 to 20) amino acid residues downstream of the NPXXY motif and the portion from the second GPCR having clusters of phosphorylation sites and a putative site of palmitoylation approximately 10 to 25 (e.g., 15 to 20) amino acid residues downstream of a NPXXY motif comprises amino acid residues beginning with an amino acid residue immediately downstream of the putative site of palmitoylation of the second GPCR extending to the end of the carboxyl-terminus. Such a fusion allows the clusters of phosphorylation sites to be properly positioned within the carboxyl-terminal tail and allows the modified GPCR to maintain its structure and ability to function.

By way of example, a Class A receptor or an orphan receptor may have a portion of its carboxyl-terminal tail exchanged with a portion of a carboxyl-terminal tail from a known Class B receptor. Further, receptors having virtually non-existent carboxyl-terminal tails, for example, olfactory receptors and taste receptors, may have a portion of their carboxyl-terminal tails exchanged with a portion of a carboxyl-terminal tail from a known Class B receptor. The Class B receptor tail used for these exchanges may have a marker molecule fused to the carboxyl-terminus.

Modified GPCRs may be generated by molecular biological techniques standard in the genetic engineering art, including but not limited to, polymerase chain reaction (PCR), restriction enzymes, expression vectors, plasmids, and the like. By way of example, vectors, such as a pEArrB (enhanced arrestin binding, described in U.S. patent application Ser. No. 09/993,844), may be designed to enhance the affinity of a GPCR lacking clusters of phosphorylation sites for arrestin. To form a vector, such as a pEArrB vector, PCR amplified DNA fragments of a GPCR carboxyl-terminus, which forms stable complexes with arrestin, may be digested by appropriate restriction enzymes and cloned into a plasmid. The DNA of a GPCR, which is to be modified, may also be PCR amplified, digested by restriction enzymes at an appropriate location, and subcloned into the vector, such as pEArrB. When expressed, the modified GPCR will contain a polypeptide fused to the carboxyl-terminus. The polypeptide will comprise clusters of phosphorylation sites. In one embodiment, the polypeptide originates from the GPCR carboxyl-terminus of a receptor that forms stable complexes with arrestin.

Such modified GPCRs may also occur naturally as the result of aberrant gene splicing or single nucleotide polymorphisms. Such naturally occurring modified GPCRs would be predicted to have modified endocytic targeting.

As shown in FIG. 6A, a portion of a $\beta_2$AR, a Class A receptor, may be fused to a portion of a V2R receptor (a Class B receptor). As shown in the figure, the first 341 amino acids of the $\beta_2$AR, Met-1 through Cys-341 (a putative site of palmitoylation) may be fused to the last 29 amino acids of the V2R carboxyl-terminus (Ala-343 through Ser-371;

Ala-343 is immediately following a palmitoylated cysteine). This fusion properly positions the V2R cluster of phosphorylation sites (SSS) within the modified GPCR's tail.

As shown in FIG. 6B, a portion of a mu opioid receptor (MOR), a Class A receptor, may be fused to a portion of a V2R receptor (a Class B receptor). As shown in the figure, the first 351 amino acids of the MOR, Met-1 through Cys-351 (a palmitoylated cysteine residue), may be fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

Also as shown in FIG. 6C, a portion of a dopamine D1A receptor (D1AR), a Class A receptor, may be fused to a portion of a V2R receptor. As shown in the figure, the first 351 amino acids of the DIAR, Met-1 through Cys-351 (a palmitoylated cysteine) may be fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

Further as shown in FIG. 6D, a portion of a 5-hydroxytryptamine 1A receptor (5HT1AR), a Class A receptor, may be fused to a portion of a V2R receptor (a Class B receptor). As shown in the figure, the first 420 amino acids of the 5HT1AR, Met-1 through Cys-420 (a palmitoylated cysteine) may be fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

As shown in FIG. 6E, a portion of a β3-adrenergic receptor (β3AR), a Class A receptor, may be fused to a portion of a V2R receptor (a Class B receptor). As shown in the figure, the first 363 amino acids of the β3AR, Met-1 through Cys-363 (a palmitoylated cysteine) may be fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

Finally as shown in FIG. 6F, a portion of a endothelial differentiation, sphingolipid GPCR 1 (Edg1R), a Class A receptor, may be fused to a portion of a V2R receptor (a Class B receptor). As shown in the figure, the first 331 amino acids of the Edg1R, Met-1 through Cys-331 (a palmitoylated cysteine) may be fused to the last 29 amino acid of the V2R carboxyl-terminus (Ala-343 through Ser-371; Ala-343 is immediately following a palmitoylated cysteine). This fusion properly positions the V2R cluster of phosphorylation sites (SSS) within the modified GPCR's tail.

The modified GPCRs described in U.S. Provisional Patent Application No. 60/401,698, filed August 7, 2002, the content of which is hereby incorporated by reference herein in its entirety, may also be used in the present invention. The GPCRs described in U.S. Provisional Patent Application No. 60/401,698 include the following receptors that have enhanced affinity for arrestin: hGPR3E, hGPR6E, hGPR12E, hGPR8E, hGPR22E, hSREB2E, and hSREB3E. The "E" stands for "enhanced arrestin binding". Each of these modified GPCRs contains a properly positioned cluster of phosphorylation sites (SSS) within the modified GPCR's tail. FIG. 5 lists the amino acid and nucleic acid sequences for these GPCRs.

As may be shown by standard receptor binding assays, the modified receptors are essentially indistinguishable from their wild-type counterparts except for an increased affinity for arrestin and thus an increased stability of their complex with arrestin and in their ability to traffic with arrestin and in their ability to recycle and resensitize. For example, the modified receptors are appropriately expressed at the membrane and possess similar affinity for agonists or ligands.

3. Other Modified GPCRs

Other modified GPCRs may also be used in the present invention so long as the modified GPCRs are capable of participating in the GPCR desensitization pathway such that GPCR desensitization inhibitory activity of a test composition may be determined. For example, the human $β_2$AR-E-Y326A containing a point mutation (i.e., the Tyrosine residue 326 converted to Alanine) may be used in the present invention. $β_2$AR-E-Y326A is described in U.S. Provisional Patent Application No. 60/401,698. The "E" indicates that the GPCR has been modified as described above to have enhanced affinity for arrestin. The Y326A mutation causes the GPCR to be dependent on overexpressed GRK for phosphorylation and subsequent desensitization.

Cells

Cells useful in the present invention include eukaryotic and prokaryotic cells, including, but not limited to, bacterial cells, yeast cells, fungal cells, insect cells, nematode cells, plant cells, and animal cells. Suitable animal cells include, but are not limited to, HEK cells, HeLa cells, COS cells, U20S cells, CHO-K1 cells, and various primary mammalian cells. An animal model expressing one or more conjugates described above (e.g., a conjugate of an arrestin and a marker molecule) throughout its tissues or within a particular organ or tissue type, may be useful in the methods of the present invention.

Cells useful in the present invention include those that express a known GPCR, a variety of known GPCRs, an unknown GPCR, a variety of unknown GPCRs, a modified GPCR, a variety of modified GPCRs, and combinations thereof. A cell that expresses a GPCR is one that contains the GPCR as a functional receptor in its cell membrane. The cells may naturally express the GPCRs, may be genetically engineered to express the GPCRs at varying levels of expression, or may be genetically engineered to inducibly express the GPCRs. As one skilled in the art readily would understand, the cells may be genetically engineered to express GPCRs by molecular biological techniques standard in the genetic engineering art.

Conjugates

In the methods of the present invention, each of the cells comprises one or more conjugates of a marker molecule and a protein associated with the GPCR desensitization pathway of one or more GPCRs that are being used in the cell to screen a test composition for GPCR desensitization inhibitory activity. For example, one or more of the cells may comprise a conjugate of an arrestin protein and a marker molecule and/or a conjugate of a GPCR and a marker molecule.

All forms of arrestin, both naturally occurring and engineered variants, including but not limited to, visual arrestin, β-arrestin 1 and β-arrestin 2, may be used in the present invention.

Marker molecules that may be used to conjugate with the arrestin include, but are not limited to, molecules that are detectable by spectroscopic, photochemical, radioactivity, biochemical, immunochemical, colorimetric, electrical, and optical means, including but not limited to, bioluminescence, phosphorescence, and fluorescence. These marker molecules should be biologically compatible molecules and should not compromise the ability of the arrestin to interact with the GPCR system, and the interaction of the arrestin with the GPCR system must not compromise the ability of the marker molecule to be detected. Marker molecules include radioisotopes, epitope tags, affinity labels, enzymes, fluorescent groups, chemiluminescent groups, and the like. Marker molecules include molecules that are directly or indirectly detected as a function of their interaction with other molecule(s) as well as molecules detected as a function of their location or translocation. In some embodiments, the marker molecules are optically detectable marker molecules, including optically detectable proteins, such that they may be excited chemically, mechanically, electrically, or radioactively to emit fluorescence, phosphorescence, or bioluminescence. Optically detectable marker molecules include, for example, beta-galactosidase, firefly luciferase, bacterial luciferase, fluorescein, Texas Red, horseradish peroxidase, alkaline phosphatase, and rhodamine-conjugated antibody. In other embodiments, the optically detectable marker molecules are inherently fluorescent molecules, such as fluorescent proteins, including, for example, Green Fluorescent Protein (GFP).

The marker molecule may be conjugated to the arrestin protein by methods as described in U.S. Pat. Nos. 5,891,646 and 6,110,693. The marker molecule may be conjugated to the arrestin at the front-end, at the back-end, or in the middle. In some embodiments, the marker molecules are molecules that are capable of being synthesized in the cell. The cell can be transfected with DNA so that the conjugate of arrestin and a marker molecule is produced within the cell. As one skilled in the art readily would understand, cells may be genetically engineered to express the conjugate of arrestin and a marker molecule by molecular biological techniques standard in the genetic engineering art.

The GPCRs used in the present invention may also be conjugated with a marker molecule. In some embodiments, the carboxyl-terminus of the GPCR is conjugated with a marker molecule. A carboxyl-terminal tail conjugated or attached to a marker molecule can be used in a carboxyl-terminal tail exchange to provide a modified GPCR.

If the GPCR is conjugated with a marker molecule, proximity of the GPCR with the arrestin may be readily detected. In addition, if the GPCR is conjugated with a marker molecule, compartmentalization of the GPCR with the arrestin may be readily confirmed. The marker molecule used to conjugate with the GPCRs may include those as described above, including, for example, optically detectable marker molecules, such that they may be excited chemically, mechanically, electrically, or radioactively to emit fluorescence, phosphorescence, or bioluminescence. Optically detectable marker molecules may be detected by, for example, immunofluorescence, luminescence, fluorescence, and phosphorescence.

For example, the GPCRs may be antibody labeled with an antibody conjugated to an immunofluorescence molecule or the GPCRs may be conjugated with a luminescent donor. In particular, the GPCRs may be conjugated with, for example, luciferase, for example, *Renilla* luciferase, or a rhodamine-conjugated antibody, for example, rhodamine-conjugated anti-HA mouse monoclonal antibody. The carboxyl-terminal tail of the GPCR may be conjugated with a luminescent donor, for example, luciferase. The GPCR also may be conjugated with GFP (e.g., at the carboxyl-terminal tail of the GPCR) as described in L. S. Barak et al. "Internal Trafficking and Surface Mobility of a Functionally Intact $\beta_2$-Adrenergic Receptor-Green Fluorescent Protein Conjugate", *Mol. Pharm*. (1997) 51, 177–184.

Modifications to Other Proteins

Other proteins may also be modified for use in the screening methods described herein. For example, an arrestin may have one or more modifications (e.g., genetic mutations or other functional alterations) in any part thereof that either enhances or reduces the affinity of the arrestin for the GPCR. In addition, AP-2 protein and clathrin may have one or more modifications in any part thereof that either enhances or reduces the ability of arrestins bound to a receptor to remain bound. The altered affinity of arrestin for the GPCR may lead to a constitutively desensitized GPCR. Additionally, the expression of arrestin may be increased with respect to wild-type, which may lead to a constitutively desensitized GPCR.

Further, a G protein-coupled receptor kinase (GRK) may have one or more modifications in any part thereof that either enhances phosphorylation of a GPCR (leading to enhanced affinity of the GPCR for arrestin) or reduces phosphorylation of a GPCR. The modified GRK may lead to constitutive desensitization. One such modified GRK includes GRK-C20, described in U.S. Provisional Patent Application No. 60/401,698. Additionally, the expression of GRKs may be increased with respect to wild-type, which may lead to a constitutively desensitized GPCR.

In addition, a protein phosphatase may have one or more modifications in any part thereof that either enhances or reduces dephosphorylation of a GPCR, leading to enhanced or reduced affinity of the GPCR for arrestin. Modification(s) in a protein phosphatase may lead to constitutive desensitization. Protein phosphatases that may be involved in the GPCR signaling pathway, include, for example, calcium regulated serine threonine phosphatases. Examples of Ca-regulated serine threonine phosphatases include the PPEF1/PPEF2 family of phosphatases.

Methods of Detection

Methods of detecting the intracellular location, concentration, or translocation of a conjugate of a protein associated with the GPCR desensitization pathway (e.g., an arrestin protein or a GPCR) and a marker molecule or interaction of the conjugate with another molecule (e.g., interaction of an arrestin protein with a GPCR) will vary depending upon the marker molecule(s) used. For example, the methods of detecting the intracellular location, concentration, or translocation of the conjugate of an arrestin protein and a marker molecule or of a conjugate of a GPCR and a marker molecule, including for example, the concentration of arrestin at a cell membrane, colocalization of arrestin with GPCR in endocytic vesicles or endosomes, and concentration of arrestin in clathrin-coated pits, and the like, will vary depending on the marker molecule(s) used. One skilled in the art readily will be able to devise detection methods suitable for the marker molecule(s) used. For optically marker molecules, any optical method may be used where a change in the fluorescence, bioluminescence, or phosphorescence may be measured due to a redistribution or reorientation of emitted light. Such methods include, for example, polarization microscopy, bioluminescence resonance energy transfer (BRET), fluorescence resonance energy transfer (FRET), evanescent wave excitation microscopy, and standard or confocal microscopy.

In one embodiment, an arrestin protein may be conjugated to a GFP and the arrestin-GFP conjugate may be detected by confocal microscopy. In another embodiment, an arrestin protein may be conjugated to a GFP and a GPCR may be conjugated to an immunofluorescent molecule; the conjugates may be detected by confocal microscopy. In an additional embodiment, an arrestin protein may be conjugated to a GFP, and the carboxy-terminus of a GPCR may be conjugated to a luciferase. These conjugates can be detected by BRET. In a further embodiment, an arrestin protein may be conjugated to a luciferase, and a GPCR may be conjugated to a GFP. The luciferase/GFP conjugates may be detected by BRET.

Methods of detection that may be used with the methods of the present invention are also described in U.S. patent application Ser. No. 10/095,620, U.S. Pat. No. 5,891,646 and U.S. Pat. No. 6,110,693, the contents of which are hereby incorporated by reference herein in their entirety.

Secondary Assays

After receiving an indication of non-receptor-specific GPCR desensitization inhibitory activity for a particular test composition using one or more of the methods for screening described above, various secondary assays may be performed to further characterize the activity of the test composition and/or to confirm (i.e., give a further indication) that the GPCR desensitization inhibitory activity of the test composition is not receptor specific. Assays that may be used to further characterize the activity of the test composition include, but are not limited to in vivo and/or in vitro kinase activity assays, including GRK activity assays. Assays that may be used to confirm that the GPCR desensitization inhibitory activity of the test composition is not receptor specific include, but are not limited to, GPCR ligand binding assays. In addition, any other assays known to those skilled in the art may also be used to characterize the activity, confirm the non-receptor specificity, or characterize other properties of a test composition that has been indicated to have non-receptor-specific GPCR desensitization inhibitory activity. Kinase assays and GPCR ligand binding assays are described more fully below.

1. Kinase Assays

Kinase assays (e.g., whole cell phosphorylation or in vitro phosphorylation assays) may be used to further characterize a test composition that has given an indication of non-receptor-specific GPCR desensitization inhibitory activity to determine if the test composition is a kinase inhibitor. Such a determination may be made by assaying for the ability of the test composition to inhibit phosphorylation by a specific kinase (e.g., a specific GRK). In addition, multiple kinase assays could be performed to further characterize the test composition to determine which, if any, kinases the composition inhibits. In one particular embodiment, a GRK assay is performed using a specific GRK and a GPCR for which the GRK is specific (as the substrate for phosphorylation) to determine whether the composition is an inhibitor of that specific GRK. Kinase phosphorylation assays are known in the art. For example, U.S. Pat. No. 6,096,705 describes an assay for βAR kinase activity.

2. GPCR Ligand Binding Assays

GPCR ligand binding assays may be used to confirm (i.e., give a further indication) that the GPCR desensitization inhibitory activity of a test composition is not receptor specific. A known ligand of a specific GPCR is labeled, and then the labeled ligand and a test composition are assayed with the specific GPCR. Any suitable label may be used such as for example, radioactive labels such as $^3$H, $^{32}$P, etc., and nonradioactive labels. The label may comprise any marker molecule as defined above. The labeled ligand (e.g., radiolabeled ligand) and the test composition are allowed to compete for binding with the specific GPCR. The assay may be conducted using cells comprising the specific GPCR or may be conducted using a cell-free format (e.g., using membrane preparations containing the specific GPCR). After the test composition and the labeled ligand are allowed to compete for binding with the specific GPCR, the amount of labeled ligand bound to the GPCR is measured. Based on the amount of ligand bound to the GPCR, a determination may be made as to whether the test composition competitively binds to the GPCR. The measurement may be compared to a control assay where only the labeled ligand is allowed to bind with the GPCR.

The specific GPCR used in the ligand binding assay may be one of the GPCRs used in the method of screening the composition. In addition, multiple GPCR ligand binding assays may be conducted in order to test each GPCR used in the method of screening the composition. For example, where three cells are used in a method of screening a composition for non-receptor-specific GPCR desensitization inhibitory activity (e.g., a first cell having a first GPCR, a second cell having a second GPCR different from the first GPCR, and a third cell having a third GPCR different from the first and second GPCRs), a separate GPCR ligand binding assay may be conducted for each GPCR to verify that the test composition is not specific for any of the receptors.

EXAMPLE

The invention will be further explained by the following illustrative example that is intended to be non-limiting.

Introduction

Fifteen compounds were evaluated for their ability to inhibit desensitization in a non-receptor-specific manner (i.e., the fifteen compounds were screened for non-receptor-specific GPCR desensitization inhibitory activity). Each of the fifteen compounds was separately screened for GPCR desensitization inhibitory activity against HA-tagged human $\beta_2$-adrenergic receptor ($\beta_2$AR) and against human vasopressin $V_2$ receptor (V2R). In addition, the effects of temperature and carbon dioxide ($CO_2$) were evaluated with respect to each compound.

Cells

The assay was carried out using two different "double stable" human osteosarcoma cell (U2OS) lines. One cell line (U2OS-$\beta_2$AR/ArrGFP) stably expressed $\beta_2$AR and an arrestin-GFP conjugate of the *Renilla* reniformis green fluorescent protein fused in frame to the carboxyl terminus of rat β-arrestin2. The other cell line (U2OS-V2R/ArrGFP) stably expressed V2R and the same arrestin-GFP conjugate.

The double stable cell lines were generated using plasmid DNA constructs as described in Oakley et al., "The Cellular Distribution of Fluorescently Labeled Arrestins Provides a Robust, Sensitive, and Universal Assay for Screening G Protein-Coupled Receptors", *Assay and Drug Development Technologies*, Volume 1, Number 1-1, pp. 21–30, 2002.

Test Compounds

The fifteen test compounds used for screening in the example are listed below in Table 1. The table lists the compound name, the vendor of the compound, the vendor product number of the compound, the identifier used herein to refer to the compound, and the Chemical Abstract Service number (CAS#) of the compounds.

TABLE 1

Test compounds

| Compound name | Vendor (vendor product #) | CAS # |
|---|---|---|
| Ketotifen fumarate salt | SIGMA-RBI (K2628) | 34580-13-7 |
| 3-tert-Butyl-2-propionyl-2H-indeno[1,2-c]pyrazol-4-one | Menai (E343) | 437710-47-9 |
| 5-[2-(5-Nitro-furan-2-yl)-vinyl]-furan-2-carboxylic acid methyl ester | Maybridge (NRB 00507) | 18873-34-2 |
| 4-amino-2-methyl-N-[2-[(2-nitrophenyl)thio]phenyl]-5-Pyrimidinemethanamine | not commercially available | 403514-61-4 |
| RO-31-7549 | Calbiochem (557508) | 125313-65-7 |
| RO-31-8425 | Calbiochem (557514) | 131848-97-0 |
| Bisindolylmaleimide III | Alexis (270-051-M005) | 137592-43-9 |
| Bisindolylmaleimide VI | Alexis (270-054-M005) | 137592-46-2 |
| Bisindolylmaleimide VII | Alexis (270-055-M005) | 137592-47-3 |
| Bisindolylmaleimide II | Calbiochem (203292) | 137592-45-1 |
| Bisindolylmaleimide III, Hydrochloride | Calbiochem (203294) | |
| Bisindolylmaleimide IV | Calbiochem (203297) | 119139-23-0 |
| 6-Fluoronorepinephrine, Hydrochloride | Sigma-Aldrich (B-012) | 70952-50-0 |
| Sanguinarine Chloride (S5890) | Sigma-Aldrich (S5890) | 2447-54-3 |
| Sanguinarine Chloride (LOPAC) | Sigma-Aldrich (obtained from Sigma as part of the LOPAC Library of Pharmacologically Active Compounds as a solution in DMSO) | 2447-54-3 |

Methods

The two cell lines (U20S-$\beta_2$AR/ArrGFP and U20S-V2R/ArrGFP) were separately plated at 7000 cells/well on 384 well glass bottom plates. Two plates of U20S-$\beta_2$AR/ArrGFP cells were prepared and two plates of U20S-V2R/ArrGFP cells were prepared. The cells were then incubated in a humidified environment at 37° C. in 5% $CO_2$/95% $O_2$ for 24 hours prior to screening.

Growth media was replaced with serum free media (i.e., Eagle's minimum essential medium (EMEM) buffered with 10 mM HEPES (N-2-Hydroxyethylpiperazine-N'-2-ethanesulfonic acid)) 24 hours after plating of the cells. One plate for each cell line was incubated for 10 minutes at room temperature and atmospheric $CO_2$ (referred to as the "$\beta_2$AR RT" and "V2R RT" plates) and the other plate for each cell line was incubated for 10 minutes at 37° C. and 5% $CO_2$/95% $O_2$ (referred to as the "$\beta_2$AR CO2" and "V2R CO2" plates).

Each test compound was solvated using 100% dimethyl sulfoxide (DMSO). Multiple solutions of each compound were prepared at varying concentrations for testing in separate wells of each plate. If needed, the solutions were sonicated and heated to increase solubility. After preparation of the compound solutions, they were shielded from light.

Each of the solutions of varying concentrations of the fifteen compounds was added to a well on each of the four plates. The $\beta_2$AR RT and V2R RT plates were incubated for 30 minutes at room temperature and atmospheric $CO_2$. The $\beta_2$AR CO2 and V2R CO2 plates were incubated for 30 minutes at 37° C. and 5% $CO_2$/95% $O_2$.

Agonist was then added to each well. 100 nM isoproterenol (0.4% weight/volume ascorbic acid) was used for the $\beta_2$AR plates and 100 nM arginine vasopressin was used for the V2R plates. The $\beta_2$AR RT and V2R RT plates were incubated for 30 minutes at room temperature and atmospheric $CO_2$. The $\beta_2$AR CO2 and V2R CO2 plates were incubated for 30 minutes at 37° C. and 5% $CO_2$/95% $O_2$.

Each assay was then terminated using 1% paraformaldehyde containing 1 μM DRAQ5 DNA probe to fix the cells. The cells were analyzed using a pre-production model (alpha unit) of the IN Cell Analyzer 3000 (Amersham Biosciences), which is a line scanning, confocal imaging system. The IN Cell Analyzer 3000 was used to quantitate the localization of the arrestin-GFP conjugate for the cells in each well using the Amersham Biosciences granularity analysis GRNO algorithm. This algorithm finds the nucleus of cells and then dilates out a specified distance in which fluorescent spots or "grains" of arrestin-GFP localization are identified based on size and fluorescent intensity. The average of the fluorescent intensity of the identified grains per cell in an acquired image (i.e., Fgrains) was determined for each well on the plates.

Controls

Control wells were used on each plate to determine the basal level of Fgrains for the cells on the different plates (Basal) as well as to determine the maximally stimulated level of Fgrains for the cells on the different plates (Stimulated). The cells in the Basal control wells were subjected to the method described above, but no test compound or agonist was added to the wells. The cells in the Stimulated control wells were subjected to the method described above, including the addition of agonist, but no test compound was added to the wells.

As a positive control, concentration-response curves of propanolol (an antagonist of $\beta_2$AR) were run in parallel as well as a block of maximal concentration (1100 nM).

Results

The Fgrains results for the assays of each of the test compounds and the assays for propanolol were plotted versus the concentrations of the respective compounds. Then, using a curve-fitting program, a concentration-response curve was plotted on the graph for compounds that showed inhibitory activity. No concentration-response curve was plotted on the assays that showed little or no inhibitory activity. The graphs for each compound as well as for the propanolol control are illustrated in FIGS. 7–22.

Based on the results of the concentration-response curves, the following data was also obtained for the assays in which curves were plotted: the change between the fitted maximum and fitted minimum Fgrains value for each compound (i.e., Max Rsp); the compound concentration that caused the half-maximal response (i.e., EC50); the negative log of EC50 (i.e., pEC50); the minimum Fgrains value for each compound as determined by the curve-fitting program (i.e., Min); and the slope of the calculated concentration-response curve. The curve-fitting program allowed the minimum and maximum values as well as the slope and EC50 values to vary rather than fixing the values to specified or collected values. The data obtained for each compound and the propanolol control is listed below in Tables 2–13.

TABLE 2

Bisindolylmaleimide III

| Test compound | Plate | Max Rsp | EC50 (μM) | pEC50 | Min | slope |
|---|---|---|---|---|---|---|
| Bisindolylmaleimide III | B2AR RT | 232 | 22.4 | 4.7 | 212 | 1.2 |
| Bisindolylmaleimide III | B2AR CO2 | 194 | 11.1 | 5.0 | 243 | 1.8 |
| Bisindolylmaleimide III | V2R RT | 361 | 19.3 | 4.7 | 225 | 0.9 |
| Bisindolylmaleimide III | V2R CO2 | 298 | 6.0 | 5.2 | 291 | 1.9 |

TABLE 3

Bisindolylmaleimide VI

| Test compound | Plate | Max Rsp | EC50 (μM) | pEC50 | Min | slope |
|---|---|---|---|---|---|---|
| Bisindolylmaleimide VI | B2AR RT | 210 | 9.0 | 5.0 | 213 | 4.4 |
| Bisindolylmaleimide VI | B2AR CO2 | 270 | 12.7 | 4.9 | 170 | 2.4 |
| Bisindolylmaleimide VI | V2R RT | 696 | 18.3 | 4.7 | −118 | 1.2 |
| Bisindolylmaleimide VI | V2R CO2 | 499 | 24.6 | 4.6 | 94 | 0.8 |

TABLE 4

Bisindolylmaleimide VII

| Test compound | Plate | Max Rsp | EC50 (μM) | pEC50 | Min | slope |
|---|---|---|---|---|---|---|
| Bisindolylmaleimide VII | B2AR RT | 281 | 24.9 | 4.6 | 148 | 2.2 |
| Bisindolylmaleimide VII | B2AR CO2 | 278 | 21.2 | 4.7 | 167 | 2.3 |
| Bisindolylmaleimide VII | V2R RT | 717 | 36.6 | 4.4 | −130 | 1.1 |
| Bisindolylmaleimide VII | V2R CO2 | 336 | 9.3 | 5.0 | 250 | 2.4 |

TABLE 5

RO-31-7549

| Test compound | Plate | Max Rsp | EC50 (μM) | pEC50 | Min | slope |
|---|---|---|---|---|---|---|
| RO-31-7549 | B2AR RT | 423 | 31.1 | 4.5 | 4 | 0.8 |
| RO-31-7549 | B2AR CO2 | 243 | 9.4 | 5.0 | 193 | 1.2 |
| RO-31-7549 | V2R RT | 320 | 3.3 | 5.5 | 250 | 1.5 |
| RO-31-7549 | V2R CO2 | 357 | 2.7 | 5.6 | 240 | 1.0 |

TABLE 6

RO-31-8425

| Test compound | Plate | Max Rsp | EC50 (μM) | pEC50 | Min | slope |
|---|---|---|---|---|---|---|
| RO-31-8425 | B2AR RT | 359 | 23.2 | 4.6 | 60 | 1.3 |
| RO-31-8425 | B2AR CO2 | 203 | 8.8 | 5.1 | 233 | 2.1 |
| RO-31-8425 | V2R RT | 342 | 6.9 | 5.2 | 241 | 1.5 |
| RO-31-8425 | V2R CO2 | 532 | 13.9 | 4.9 | 60 | 1.0 |

TABLE 7

3-tert-Butyl-2-propionyl-2H-indeno[1,2-c]pyrazol-4-one

| Test compound | Plate | Max Rsp | EC50 (μM) | pEC50 | Min | slope |
|---|---|---|---|---|---|---|
| 3-tert-Butyl-2-propionyl-2H-indeno[1,2-c]pyrazol-4-one | B2AR CO2 | 129 | 46.9 | 4.3 | 307 | 3.2 |

TABLE 8

Bisindolylmaleimide II

| Test compound | Plate | Max Rsp | EC50 (μM) | pEC50 | Min | slope |
|---|---|---|---|---|---|---|
| Bisindolylmaleimide II | B2AR RT | 924 | 87.3 | 4.1 | −508 | 1.7 |
| Bisindolylmaleimide II | B2AR CO2 | 502 | 62.1 | 4.2 | −70 | 1.7 |
| Bisindolylmaleimide II | V2R RT | 576 | 35.0 | 4.5 | −7 | 1.1 |
| Bisindolylmaleimide II | V2R CO2 | 420 | 29.2 | 4.5 | 159 | 1.2 |

TABLE 9

Bisindolylmaleimide III, Hydrochloride

| Test compound | Plate | Max Rsp | EC50 (μM) | pEC50 | Min | slope |
|---|---|---|---|---|---|---|
| Bisindolylmaleimide III, Hydrochloride | B2AR RT | 171 | 34.9 | 4.5 | 237 | 3.5 |
| Bisindolylmaleimide III, Hydrochloride | B2AR CO2 | 998 | 232.6 | 3.6 | −568 | 1.1 |
| Bisindolylmaleimide III, Hydrochloride | V2R RT | 690 | 51.2 | 4.3 | −118 | 1.2 |
| Bisindolylmaleimide III, Hydrochloride | V2R CO2 | 455 | 27.2 | 4.6 | 129 | 1.4 |

TABLE 10

Bisindolylmaleimide IV

| Test compound | Plate | Max Rsp | EC50 (μM) | pEC50 | Min | slope |
|---|---|---|---|---|---|---|
| Bisindolylmaleimide IV | V2R CO2 | 277 | 69.2 | 4.2 | 292 | 6.5 |

TABLE 11

Sanguinarine Chloride (S5890)

| Test compound | Plate | Max Rsp | EC50 (μM) | pEC50 | Min | slope |
|---|---|---|---|---|---|---|
| Sanguinarine Chloride (S5890) | B2AR RT | 340 | 7.7 | 5.1 | 61 | 1.3 |
| Sanguinarine Chloride (S5890) | B2AR CO2 | 312 | 7.0 | 5.2 | 108 | 3.3 |
| Sanguinarine Chloride (S5890) | V2R RT | 533 | 9.0 | 5.0 | 27 | 2.0 |
| Sanguinarine Chloride (S5890) | V2R CO2 | 546 | 12.7 | 4.9 | 27 | 2.1 |

TABLE 12

Sanguinarine Chloride (LOPAC)

| Test compound | Plate | Max Rsp | EC50 (μM) | pEC50 | Min | slope |
|---|---|---|---|---|---|---|
| Sanguinarine Chloride (LOPAC) | B2AR RT | 330 | 2.8 | 5.6 | 76 | 1.8 |
| Sanguinarine Chloride (LOPAC) | B2AR CO2 | 350 | 3.3 | 5.5 | 85 | 1.6 |
| Sanguinarine Chloride (LOPAC) | V2R RT | 508 | 4.1 | 5.4 | 45 | 2.3 |
| Sanguinarine Chloride (LOPAC) | V2R CO2 | 519 | 5.7 | 5.2 | 63 | 2.6 |

TABLE 13

| | | Propanolol | | | | |
|---|---|---|---|---|---|---|
| Antagonist | Plate | Max Rsp | EC50 (nM) | pEC50 | Min | slope |
| Propranolol | B2AR RT | 270 | 6.3 | 8.2 | 131 | 1.8 |
| Propranolol | B2AR CO2 | 270 | 6.5 | 8.2 | 141 | 1.9 |

Table 14 below lists the mean Fgrains value for the cells in the Basal and Stimulated control wells on each plate and the standard error of the mean (S.E.M.) of each value.

TABLE 14

| | Basal and Stimulated Control Wells | | | |
|---|---|---|---|---|
| Plate | Basal | S.E.M. | Stimulated | S.E.M. |
| B2AR RT | 118 | 7 | 406 | 5 |
| B2AR CO2 | 139 | 5 | 431 | 1 |
| V2R RT | 77 | 6 | 568 | 1 |
| V2R CO2 | 81 | 5 | 572 | 1 |

As indicated by the Fgrains values for the cells in the Basal and Stimulated control wells, the Fgrains value determined by the IN Cell Analyzer 3000 in this example was functionally a measure of the average extent of desensitization in the cells in each well. By comparing the Fgrains level of the cells in the control wells for each plate (especially the Stimulated control) to the concentration-response curves of the test compounds in the two stable cell lines expressing different receptors, several compounds show an indication of GPCR desensitization inhibitory activity for one or both receptors. Those test compounds showing GPCR desensitization inhibitory activity for both receptors therefore also show an indication that the test compounds have non-receptor-specific GPCR desensitization inhibitory activity (i.e., Bisindolylmaleimide III; Bisindolylmaleimide VI; Bisindolylmaleimide VII; RO-31-7549; RO-31-8425; Bisindolylmaleimide II; Bisindolylmaleimide III, Hydrochloride; Sanguinarine Chloride (S5890); and Sanguinarine Chloride (LOPAC)). The propanolol control illustrated an indication of GPCR desensitization inhibitory activity with respect to the $\beta_2$AR but not the V2R.

While the invention has been described in detail and with reference to specific embodiments thereof, it will be apparent to one skilled in the art that various changes and modifications can be made without departing from the spirit and scope of the invention.

What is claimed is:

1. A method of screening a composition for non-receptor-specific G-protein coupled receptor (GPCR) desensitization inhibitory activity comprising the steps of:
   (a) providing a first cell comprising a first GPCR and a first conjugate of a marker molecule and a protein associated with the desensitization pathway of the first GPCR, the first GPCR being a GPCR that requires an agonist for desensitization or being a constitutively desensitized GPCR;
   (b) exposing the first cell to a test composition and, when the first GPCR requires agonist for desensitization, to an agonist for the first GPCR;
   (c) determining, through detection of the marker molecule in the first conjugate, whether or not the composition gives an indication of GPCR desensitization inhibitory activity with respect to the first GPCR;
   (d) providing a second cell comprising a second GPCR different from the first GPCR and a second conjugate of a marker molecule and a protein associated with the desensitization pathway of the second GPCR, the second conjugate being the same or different from the first conjugate, the second GPCR being a GPCR that requires an agonist for desensitization or being a constitutively desensitized GPCR;
   (e) exposing the second cell to the test composition and, when the second GPCR requires agonist for desensitization, to an agonist for the second GPCR;
   (f) determining, through detection of the marker molecule in the second conjugate, whether or not the composition gives an indication of GPCR desensitization inhibitory activity with respect to the second GPCR; wherein an indication of GPCR desensitization inhibitory activity for the test composition in both step (c) and step (f) being an indication that the test composition has non-receptor-specific GPCR desensitization inhibitory activity.

2. The method of claim 1, wherein the protein in the first conjugate associated with the desensitization pathway of the first GPCR is selected from the group consisting of an arrestin protein and the first GPCR and wherein the protein in the second conjugate associated with the desensitization pathway of the second GPCR is selected from the group consisting of an arrestin protein and the second GPCR.

3. The method of claim 1, wherein the marker molecule of the first conjugate and the marker molecule of the second conjugate are independently selected from the group consisting of radioisotope, epitope tag, affinity label, enzyme, fluorescent group, and chemiluminescent group.

4. The method of claim 2, wherein the marker molecule of the first conjugate and the marker molecule of the second conjugate are independently selected from the group consisting of radioisotope, epitope tag, affinity label, enzyme, fluorescent group, and chemiluminescent group.

5. The method of claim 1, wherein: step (c) comprises detecting for translocation or localization of the first conjugate, a lack of translocation or localization being an indication that the composition has GPCR desensitization inhibitory activity; and step (f) comprises detecting for translocation or localization of the second conjugate, a lack of translocation or localization being an indication that the composition has GPCR desensitization inhibitory activity.

6. The method of claim 1, wherein: step (c) comprises detecting for translocation or localization of the first conjugate, a decrease in translocation or localization after exposure to the test composition being an indication that the composition has GPCR desensitization inhibitory activity; and step (f) comprises detecting for translocation or localization of the second conjugate, a decrease in translocation or localization after exposure to the test composition being an indication that the composition has GPCR desensitization inhibitory activity.

7. The method of claim 1, wherein: step (c) comprises detecting for translocation or localization of the first conjugate, a decreased level of translocation or localization with respect to a level of translocation or localization determined in a control cell not exposed to the test composition being an indication that the composition has GPCR desensitization inhibitory activity, the control cell comprising the first GPCR and the first conjugate and being exposed to agonist if the first GPCR requires agonist for desensitization; and step (f) comprises detecting for translocation or localization of the second conjugate, a decreased level of translocation or localization with respect to a level of translocation or localization determined in a control cell not exposed to the test composition being an indication that the composition has GPCR desensitization inhibitory activity, the control cell comprising the second GPCR and the second conjugate and being exposed to agonist if the second GPCR requires agonist for desensitization.

8. The method of claim 1, wherein: the first GPCR is a GPCR that requires agonist for desensitization; in step (b), the first cell is exposed to the test composition first and then is exposed to the agonist for the first GPCR; the second GPCR is a GPCR that requires agonist for desensitization; and in step (e), the second cell is exposed to the test composition first and then is exposed to the agonist for the second GPCR.

9. The method of claim 1, wherein: the first GPCR is a GPCR that requires agonist for desensitization; in step (b), the first cell is exposed to the agonist for the first GPCR and then is exposed to the test composition; the second GPCR is a GPCR that requires agonist for desensitization; and in step (e), the second cell is exposed to the agonist for the second GPCR and then is exposed to the test composition.

10. The method of claim 1, wherein: in the first conjugate, the protein associated with the desensitization pathway of the first GPCR comprises an arrestin protein and the marker molecule comprises a GFP; in the second conjugate, the protein associated with the desensitization pathway of the second GPCR comprises an arrestin protein and the marker molecule comprises a GFP; the first GPCR is a GPCR that requires agonist for desensitization; the second GPCR is a GPCR that requires agonist for desensitization; in step (b), the first cell is exposed to the test composition first and then is exposed to the agonist for the first GPCR; step (c) comprises detecting for translocation or localization of the first conjugate, a lack of translocation or localization being an indication that the composition has GPCR desensitization inhibitory activity; in step (e), the second cell is exposed to the test composition first and then is exposed to the agonist for the second GPCR; and step (f) comprises detecting for translocation or localization of the second conjugate, a lack of translocation or localization being an indication that the composition has GPCR desensitization inhibitory activity.

11. The method of claim 1, wherein: the first conjugate comprises the first GPCR conjugated to the marker molecule; the second conjugate comprises the second GPCR conjugated to the marker molecule; step (c) comprises detecting for translocation or localization of the first GPCR, a lack of translocation or localization being an indication that the composition has GPCR desensitization inhibitory activity; and step (f) comprises detecting for translocation or localization of the second GPCR, a lack of translocation or localization being an indication that the composition has GPCR desensitization inhibitory activity.

12. The method of claim 1, wherein: the first conjugate comprises the first GPCR conjugated to the marker molecule; the second conjugate comprises the second GPCR conjugated to the marker molecule; step (c) comprises detecting for translocation or localization of the first GPCR, a decrease in translocation or localization after exposure to the test composition being an indication that the composition has GPCR desensitization inhibitory activity; and step (f) comprises detecting for translocation or localization of the second GPCR, a decrease in translocation or localization after exposure to the test composition being an indication that the composition has GPCR desensitization inhibitory activity.

13. A method of screening a composition for non-receptor-specific G-protein coupled receptor (GPCR) desensitization inhibitory activity comprising the steps of:
(a) providing a first cell comprising a first GPCR that requires agonist for desensitization and a first conjugate of a marker molecule and a protein associated with the desensitization pathway of the first GPCR;
(b) exposing the first cell to a test composition and to an agonist for the first GPCR;
(c) determining whether or not the composition gives an indication of GPCR desensitization inhibitory activity with respect to the first GPCR by detecting for translocation or localization of the first conjugate, the following being an indication that the composition has GPCR desensitization inhibitory activity:
(1) a lack of translocation or localization;
(2) a decrease in translocation or localization after exposure to the test composition; or
(3) a decreased level of translocation or localization with respect to a predetermined level or with respect to a level determined in a control cell not exposed to the test composition, the control cell comprising the first GPCR and the first conjugate and being exposed to the agonist for the first GPCR;
(d) providing a second cell comprising a second GPCR that requires agonist for desensitization and is different from the first GPCR and a second conjugate of a marker molecule and a protein associated with the desensitization pathway of the second GPCR, the second conjugate being the same or different from the first conjugate;
(e) exposing the second cell to the test composition and to an agonist for the second GPCR;
(f) determining whether or not the composition gives an indication of GPCR desensitization inhibitory activity with respect to the second GPCR by detecting for translocation or localization of the second conjugate, the following being an indication that the composition has GPCR desensitization inhibitory activity:
(1) a lack of translocation or localization;
(2) a decrease in translocation or localization after exposure to the test composition; or
(3) a decreased level of translocation or localization with respect to a predetermined level or with respect to a level determined in a control cell not exposed to the test composition, the control cell comprising the second GPCR and the second conjugate and being exposed to the agonist for the second GPCR;
wherein an indication of GPCR desensitization inhibitory activity for the test composition in both step (c) and step (f) being an indication that the test composition has non-receptor-specific GPCR desensitization inhibitory activity.

14. The method of claim 13, wherein the protein in the first conjugate associated with the desensitization pathway of the first GPCR is selected from the group consisting of an arrestin protein and the first GPCR and wherein the protein in the second conjugate associated with the desensitization pathway of the second GPCR is selected from the group consisting of an arrestin protein and the second GPCR.

15. The method of claim 14, wherein the marker molecule of the first conjugate and the marker molecule of the second conjugate are independently selected from the group consisting of radioisotope, epitope tag, affinity label, enzyme, fluorescent group, and chemiluminescent group.

16. The method of claim 15, wherein: in the first conjugate, the protein associated with the desensitization pathway of the first GPCR comprises an arrestin protein and the marker molecule comprises a GFP; and in the second conjugate, the protein associated with the desensitization pathway of the second GPCR comprises an arrestin protein and the marker molecule comprises a GFP.

17. The method of claim 16, wherein, when there is an indication that the test composition has non-receptor-specific GPCR desensitization inhibitory activity, the method further comprises performing a kinase assay to determine whether the test composition is a kinase inhibitor.

18. The method of claim 17, wherein, when there is an indication that the test composition has non-receptor-specific GPCR desensitization inhibitory activity, the method further comprises performing a GPCR ligand binding assay to confirm that the GPCR desensitization inhibitory activity of the test composition is not receptor specific.

19. A method of screening a composition for non-receptor-specific G-protein coupled receptor (GPCR) desensitization inhibitory activity comprising the steps of:
 (a) providing a cell comprising:
  (1) a first GPCR that is a GPCR that requires agonist for desensitization;
  (2) a second GPCR that is different than the first GPCR, the second GPCR being a GPCR that requires agonist for desensitization;
  (3) a first conjugate of a marker molecule and a protein associated with the desensitization pathway of the first GPCR; and
  (4) a second conjugate of a marker molecule and a protein associated with the desensitization pathway of the second GPCR, the second conjugate being the same or different from the first conjugate;
 (b) exposing the cell to a test composition and to an agonist for the first GPCR;
 (c) determining whether or not the composition has GPCR desensitization inhibitory activity with respect to the first GPCR;
 (d) exposing the cell to an agonist for the second GPCR and optionally re-exposing the cell to the test composition; and
 (e) determining whether or not the composition has GPCR desensitization inhibitory activity with respect to the second GPCR; wherein an indication that the test composition has GPCR desensitization inhibitory activity with respect to both the first GPCR and the second GPCR being an indication that the test composition has non-receptor-specific GPCR desensitization inhibitory activity; and wherein the agonist for the first GPCR is not an agonist for the second GPCR and the agonist for the second GPCR is not an agonist for the first GPCR.

20. The method of claim 19, wherein the protein in the first conjugate associated with the desensitization pathway of the first GPCR is selected from the group consisting of an arrestin protein and the first GPCR and wherein the protein in the second conjugate associated with the desensitization pathway of the second GPCR is selected from the group consisting of an arrestin protein and the second GPCR.

21. The method of claim 19, wherein the marker molecule of the first conjugate and the marker molecule of the second conjugate are independently selected from the group consisting of radioisotope, epitope tag, affinity label, enzyme, fluorescent group, and chemiluminescent group.

22. The method of claim 20, wherein the marker molecule of the first conjugate and the marker molecule of the second conjugate are independently selected from the group consisting of radioisotope, epitope tag, affinity label, enzyme, fluorescent group, and chemiluminescent group.

23. The method of claim 19, wherein: step (c) comprises detecting for translocation or localization of the conjugate, a lack of translocation or localization being an indication that the composition has GPCR desensitization inhibitory activity with respect to the first GPCR; and step (e) comprises detecting for translocation or localization of the conjugate, a lack of translocation or localization being an indication that the composition has GPCR desensitization inhibitory activity with respect to the second GPCR.

24. The method of claim 19, wherein: step (c) comprises detecting for translocation or localization of the conjugate, a decrease in translocation or localization after exposure to the test composition being an indication that the composition has GPCR desensitization inhibitory activity with respect to the first GPCR; and step (e) comprises detecting for translocation or localization of the second conjugate, a decrease in translocation or localization after exposure to the test composition being an indication that the composition has GPCR desensitization inhibitory activity with respect to the second GPCR.

25. The method of claim 19, wherein: step (c) comprises detecting for translocation or localization of the conjugate, a decreased level of translocation or localization with respect to a level of translocation or localization determined in a control cell not exposed to the test composition being an indication that the composition has GPCR desensitization inhibitory activity with respect to the first GPCR, the control cell comprising the first GPCR and the conjugate and being exposed to agonist if the first GPCR requires agonist for desensitization; and step (e) comprises detecting for translocation or localization of the conjugate, a decreased level of translocation or localization with respect to a level of translocation or localization determined in a control cell not exposed to the test composition being an indication that the composition has GPCR desensitization inhibitory activity with respect to the second GPCR, the control cell comprising the second GPCR and the conjugate and being exposed to agonist if the second GPCR requires agonist for desensitization.

26. A method of screening a composition for non-receptor-specific G-protein coupled receptor (GPCR) desensitization inhibitory activity comprising the steps of:
 (a) providing a cell comprising:
  (1) a first GPCR that is a GPCR that requires agonist for desensitization or is a constitutively desensitized GPCR;
  (2) a second GPCR that is different than the first GPCR, the second GPCR being a GPCR that requires agonist for desensitization or being a constitutively desensitized GPCR;

(3) a first conjugate of a first marker molecule and a protein associated with the desensitization pathway of the first GPCR; and (4) a second conjugate of a second marker molecule and a protein associated with the desensitization pathway of the second GPCR, the second conjugate being different from the first conjugate; wherein the protein of the first conjugate is not included in the desensitization pathway of the second GPCR, the protein in the second conjugate is not included in the desensitization pathway of the first GPCR, and the first and second marker molecules are different from each other and are distinguishable from each other upon detection;

(b) exposing the cell
  (1) to a test composition,
  (2) when the first GPCR requires agonist for desensitization, to an agonist for the first GPCR, and
  (3) when the second GPCR requires agonist for desensitization, to an agonist for the second GPCR; and (c) determining whether or not the composition has GPCR desensitization inhibitory activity with respect to the first GPCR and with respect to the second GPCR, wherein an indication that the test composition has GPCR desensitization inhibitory activity with respect to both the first GPCR and the second GPCR being an indication that the test composition has non-receptor-specific GPCR desensitization inhibitory activity.

27. The method of claim 26, wherein: the first conjugate comprises the first GPCR conjugated to the first marker molecule; and the second conjugate comprises the second GPCR conjugated to the second marker molecule.

28. The method of claim 26, wherein the marker molecule of the first conjugate and the marker molecule of the second conjugate are independently selected from the group consisting of radioisotope, epitope tag, affinity label, enzyme, fluorescent group, and chemiluminescent group.

29. The method of claim 27, wherein the marker molecule of the first conjugate and the marker molecule of the second conjugate are independently selected from the group consisting of radioisotope, epitope tag, affinity label, enzyme, fluorescent group, and chemiluminescent group.

30. The method of claim 26, wherein step (c) comprises: (1) detecting for translocation or localization of the first conjugate, a lack of translocation or localization being an indication that the composition has GPCR desensitization inhibitory activity with respect to the first GPCR; and (2) detecting for translocation or localization of the second conjugate, a lack of translocation or localization being an indication that the composition has GPCR desensitization inhibitory activity with respect to the second GPCR.

31. The method of claim 26, wherein step (c) comprises: (1) detecting for translocation or localization of the first conjugate, a decrease in translocation or localization after exposure to the test composition being an indication that the composition has GPCR desensitization inhibitory activity with respect to the first GPCR; and (2) detecting for translocation or localization of the second conjugate, a decrease in translocation or localization after exposure to the test composition being an indication that the composition has GPCR desensitization inhibitory activity with respect to the second GPCR.

32. The method of claim 26, wherein step (c) comprises: (1) detecting for translocation or localization of the first conjugate, a decreased level of translocation or localization with respect to a level of translocation or localization determined in a control cell not exposed to the test composition being an indication that the composition has GPCR desensitization inhibitory activity with respect to the first GPCR, the control cell comprising the first GPCR and the first conjugate and being exposed to agonist if the first GPCR requires agonist for desensitization; and (2) detecting for translocation or localization of the second conjugate, a decreased level of translocation or localization with respect to a level of translocation or localization determined in a control cell not exposed to the test composition being an indication that the composition has GPCR desensitization inhibitory activity with respect to the second GPCR, the control cell comprising the second GPCR and the second conjugate and being exposed to agonist if the second GPCR requires agonist for desensitization.

33. The method of claim 26, wherein: the first GPCR is a GPCR that requires agonist for desensitization; the second GPCR is a GPCR that requires agonist for desensitization; and in step (b), the cell is exposed to the test composition before the cell is exposed to the agonist for the first GPCR or to the agonist for the second GPCR.

34. The method of claim 26, wherein: the first conjugate comprises the first GPCR conjugated to the first marker molecule; the second conjugate comprises the second GPCR conjugated to the second marker molecule; and step (c) comprises: (1) detecting for translocation or localization of the first conjugate, a lack of translocation or localization being an indication that the composition has GPCR desensitization inhibitory activity with respect to the first GPCR; and (2) detecting for translocation or localization of the second conjugate, a lack of translocation or localization being an indication that the composition has GPCR desensitization inhibitory activity with respect to the second GPCR.

35. The method of claim 26, wherein: the first conjugate comprises the first GPCR conjugated to the first marker molecule; the second conjugate comprises the second GPCR conjugated to the second marker molecule; and step (c) comprises: (1) detecting for translocation or localization of the first conjugate, a decrease in translocation or localization after exposure to the test composition being an indication that the composition has GPCR desensitization inhibitory activity with respect to the first GPCR; and (2) detecting for translocation or localization of the second conjugate, a decrease in translocation or localization after exposure to the test composition being an indication that the composition has GPCR desensitization inhibitory activity with respect to the second GPCR.

* * * * *